United States Patent
Chen et al.

(10) Patent No.: US 12,195,735 B2
(45) Date of Patent: Jan. 14, 2025

(54) SOYBEAN PROMOTERS AND USES THEREOF

(71) Applicant: SYNGENTA CROP PROTECTION AG, Basel (CH)

(72) Inventors: Zhongying Chen, Research Triangle Park, NC (US); Nan Zhou, Research Triangle Park, NC (US); Joseph Dallas Clarke, V, Research Triangle Park, NC (US); Qiudeng Que, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 34 days.

(21) Appl. No.: 17/908,579

(22) PCT Filed: Apr. 21, 2021

(86) PCT No.: PCT/US2021/028283
§ 371 (c)(1),
(2) Date: Sep. 1, 2022

(87) PCT Pub. No.: WO2021/216630
PCT Pub. Date: Oct. 28, 2021

(65) Prior Publication Data
US 2023/0340508 A1    Oct. 26, 2023

Related U.S. Application Data

(60) Provisional application No. 63/014,232, filed on Apr. 23, 2020.

(51) Int. Cl.
*C12N 15/82*    (2006.01)

(52) U.S. Cl.
CPC ..... *C12N 15/8205* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 9,719,100 B2 * | 8/2017 | Li | C12N 15/8216 800/278 |
| 2004/0031072 A1 | 2/2004 | La Rosa et al. | |
| 2011/0296552 A1 | 12/2011 | Pinot et al. | |
| 2015/0184174 A1 * | 7/2015 | Li | C12N 15/8216 800/278 |

OTHER PUBLICATIONS

Yang et al., An efficient Agrobacterium-mediated soybean transformation method using green fluorescent protein as a selectable marker, 2019, Plant Signaling and Behavior, vol. 14(7), pp. 1-7. (Year: 2019).*
International Search Report for International Application No. PCT/US2021/028283 mailed Oct. 4, 2021.

* cited by examiner

Primary Examiner — Amjad Abraham
Assistant Examiner — Christina L Meadows
(74) Attorney, Agent, or Firm — Dale Skalla

(57) ABSTRACT

Provided herein are promoters and related compositions and methods of use. Such promoters are useful for expression cassettes for plants, such as soybean. Such expression cassettes are useful, e.g., to drive expression of trait genes in plants, such as soybean. In some aspects, the disclosure provides an expression cassette comprising a promoter, a 5' UTR, and an intron.

19 Claims, 7 Drawing Sheets

Specification includes a Sequence Listing.

SOYBEAN PROMOTERS AND USES THEREOF

RELATED APPLICATIONS

This application is a 371 of International Application No. PCT/US2021/028283, filed Apr. 21, 2021 which claims priority to U.S. provisional application No. 63/014,232 filed Apr. 23, 2021, the contents of which are incorporated by reference in their entirety herein.

FIELD OF THE INVENTION

The present invention relates to promoters that are useful for expression cassettes in plants, such as soybean.

SEQUENCE LISTING

This application is accompanied by a sequence listing entitled 82117-WO_sequence_listing.txt, created Apr. 20, 2021, which is approximately 148 kb in size. This sequence listing is incorporated herein by reference in its entirety. This sequence listing is submitted herewith via EFS-Web, and is in compliance with 37 C.F.R. § 1.824(a)(2)-(6) and (b).

BACKGROUND

Genetically modified plants are an important source of desirable traits, such as insect resistance and herbicide tolerance. In general, to create such traits, one or more nucleic acids are introduced into a plant containing expression cassettes that express one or more coding sequences for one or more traits. Such expression cassettes generally contain a promoter to control expression of each coding sequence. For certain traits, such as insect resistance and herbicide tolerance, it may be desirable to use promoters with medium to high level constitutive expression. The choices for such promoters remain limited. There remains a need for additional sequences for promoters that drive gene expression for robust protein production, ideally in all or most soybean tissues.

SUMMARY

Provided herein are regulatory elements, such as promoters and terminators, obtained or derived from *Glycine* species, e.g., *Glycine max*. Such regulatory elements are useful for constructing expression cassettes for expression of a coding sequence of interest, such as expression of a coding sequence for a trait of interest in a plant. As described herein, several promoter sequences were tested and shown to be capable of expressing proteins in one or more tissues of interest in soybean. Accordingly, aspects of the disclosure relate to such promoters, and their use in expression cassettes, vectors, and transgenic plant and plant cells.

In some aspects, the disclosure provides an expression cassette comprising a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-57, wherein the nucleotide sequence is operably linked to a heterologous nucleotide sequence. In some aspects, the disclosure provides an expression cassette comprising a nucleotide sequence comprising one or more of SEQ ID NOs: 1-57, or a biologically active fragment thereof (e.g., a fragment of at least 100, at least 200, at least 300, at least 400, at least 500, at least 600, at least 700, at least 800, at least 900 or at least 1000 contiguous nucleotides of one or more of SEQ ID NOs: 1-57), wherein the nucleotide sequence is operably linked to a heterologous nucleotide sequence. In some embodiments, the nucleotide sequence comprises any one of SEQ ID NOs: 1-57. In some embodiments, the heterologous nucleotide sequence is a nucleic acid of interest that encodes an RNA or protein of interest. In some embodiments, the RNA or protein of interest is capable of conferring upon a plant a desired characteristic such as antibiotic resistance, virus resistance, insect resistance, disease resistance, resistance to other pests, herbicide tolerance, improved nutritional value, improved performance in an industrial process or altered reproductive capability. In some embodiments, the heterologous nucleotide sequence encodes a selectable marker or wherein expression cassette further comprises a selectable marker.

Other aspects of the disclosure provide a vector comprising the expression cassette of any one of the above-mentioned embodiments or any other embodiments provided herein. In some embodiments, the vector is a plasmid, virus, or *Agrobacterium* cell.

Other aspects of the disclosure provide plant cell comprising the expression cassette or vector of any one of the above-mentioned embodiments or any other embodiments provided herein. In some embodiments, the plant cell is a dicot cell. In some embodiments, the plant cell is a *Glycine max* cell.

Other aspects of the disclosure provide a transgenic plant comprising the plant cell of any one of the above-mentioned embodiments or any other embodiments provided herein. In some embodiments, the plant is a dicot. In some embodiments, the plant is a *Glycine max* plant.

Other aspects of the disclosure provide a seed from the transgenic plant of any one of the above-mentioned embodiments or any other embodiments provided herein.

Yet other aspects of the disclosure provide a method, comprising introducing the expression cassette or vector of any one of the above-mentioned embodiments or any other embodiments provided herein into a plant or plant cell. In some embodiments, the method further comprises placing the plant or plant cell under conditions whereby an RNA or protein of interest and/or a selectable marker is expressed from the expression cassette or vector. In some embodiments, the method further comprises crossing the plant to a second plant or self-crossing the plant to produce a progeny plant. In some embodiments, the disclosure provides a transgenic plant, or a plant part thereof, produced by the method of any one of the above-mentioned embodiments or any other embodiments provided herein. In some embodiments, the plant is a dicot. In some embodiments, the plant is a *Glycine max* plant.

BRIEF DESCRIPTION OF THE SEQUENCES IN THE SEQUENCE LISTING

Figure 1:
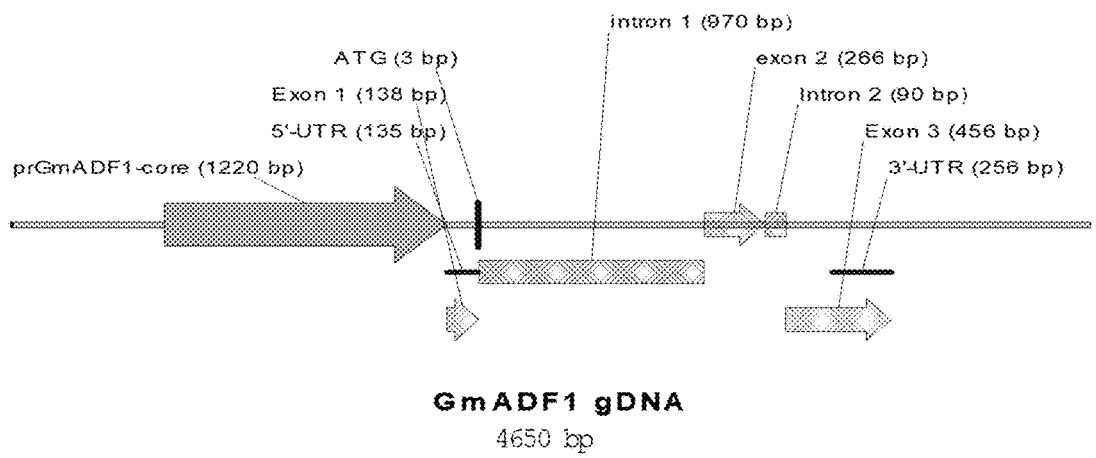
FIG. 1 is a schematic of the gene structure of the highly expressed GmADF family member (Glyma09g02240).

SEQ ID NO: 1 is GmADF1 regulatory sequences comprising GmADF promoter sequences, 5'-untranslated region (5'-UTR) and the 1st intron.

SEQ ID NO: 2 is GmADF1 regulatory sequences comprising GmADF promoter sequences, and 5'-untranslated region (5'-UTR) and the 1st intron.

SEQ ID NO: 3 is GmADF1 regulatory sequences comprising GmADF promoter sequences, and 5'-untranslated region (5'-UTR).

SEQ ID NO: 4 is GmADF1 regulatory sequences comprising GmADF promoter sequences, and 5'-untranslated region (5'-UTR).

SEQ ID NO: 5 is GmADF1 regulatory sequences comprising GmADF promoter sequences, and 5'-untranslated region (5'-UTR) and the 1st intron that have been modified as described in Example 3.

SEQ ID NO: 6 is a p01 promoter sequence.
SEQ ID NO: 7 is a p10 promoter sequence.
SEQ ID NO: 8 is a p11 promoter sequence.
SEQ ID NO: 9 is a p12 promoter sequence.
SEQ ID NO: 10 is a p14 promoter sequence.
SEQ ID NO: 11 is a p28 promoter sequence.
SEQ ID NO: 12 is a p30 promoter sequence.
SEQ ID NO: 13 is a p31 promoter sequence.
SEQ ID NO: 14 is a p32 promoter sequence.
SEQ ID NO: 15 is a p33 promoter sequence.
SEQ ID NO: 16 is a p35 promoter sequence.
SEQ ID NO: 17 is a p36 promoter sequence.
SEQ ID NO: 18 is a p37 promoter sequence.
SEQ ID NO: 19 is a p01 version 2 promoter sequence.
SEQ ID NO: 20 is a p10 version 2 promoter sequence.
SEQ ID NO: 21 is a p10 version 3 promoter sequence.
SEQ ID NO: 22 is a p10 version 4 promoter sequence.
SEQ ID NO: 23 is a p11 version 2 promoter sequence.
SEQ ID NO: 24 is a p11 version 3 promoter sequence.
SEQ ID NO: 25 is a p12 version 2 promoter sequence.
SEQ ID NO: 26 is a p12 version 3 promoter sequence.
SEQ ID NO: 27 is a p14 version 2 promoter sequence.
SEQ ID NO: 28 is a p31 version 2 promoter sequence.
SEQ ID NO: 29 is a p31 version 3 promoter sequence.
SEQ ID NO: 30 is a p32 version 2 promoter sequence.
SEQ ID NO: 31 is a p33 version 2 promoter sequence.
SEQ ID NO: 32 is a p33 version 3 promoter sequence.
SEQ ID NO: 33 is a p33 version 4 promoter sequence.
SEQ ID NO: 34 is a p35 version 2 promoter sequence.
SEQ ID NO: 35 is a p35 version 3 promoter sequence.
SEQ ID NO: 36 is a p35 version 4 promoter sequence.
SEQ ID NO: 37 is a p36 version 2 promoter sequence.
SEQ ID NO: 38 is a p36 version 3 promoter sequence.
SEQ ID NO: 39 is a p36 version 4 promoter sequence.
SEQ ID NO: 40 is a p37 version 2 promoter sequence.
SEQ ID NO: 41 is a p37 version 3 promoter sequence.
SEQ ID NO: 42 is a p01 version 3 promoter sequence.
SEQ ID NO: 43 is a prGmPIP-02 promoter sequence.
SEQ ID NO: 44 is a prGmADF-02 promoter sequence.
SEQ ID NO: 45 is a prGmADF-03 promoter sequence.
SEQ ID NO: 46 is a prGmADF-04 promoter sequence.
SEQ ID NO: 47 is a prGmCyn-02 promoter sequence.
SEQ ID NO: 48 is a prGmCypCMP-01 promoter sequence.
SEQ ID NO: 49 is a prGmCypCMP-02 promoter sequence.
SEQ ID NO: 50 is a prGmCypCMP-03 promoter sequence.
SEQ ID NO: 51 is a p28 version 2 promoter sequence.
SEQ ID NO: 52 is a p28 version 3 promoter sequence.
SEQ ID NO: 53 is a prGmSAMS-02 promoter sequence.
SEQ ID NO: 54 is a prGmSAMS-03 promoter sequence.
SEQ ID NO: 55 is a prGmGAPDH2-01 promoter sequence.
SEQ ID NO: 56 is a prGmGAPDH3-01 promoter sequence.
SEQ ID NO: 57 is a prGmGSK3-01 promoter sequence.

DEFINITIONS

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications referenced herein are incorporated by reference in their entireties for the teachings relevant to the sentence or paragraph in which the reference is presented. In case of a conflict in terminology, the present specification is controlling.

As used herein, the terms "a" or "an" or "the" may refer to one or more than one, unless the context clearly and unequivocally indicates otherwise. For example, "an" endogenous nucleic acid can mean one endogenous nucleic acid or a plurality of endogenous nucleic acids.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means ±1° C., preferably ±0.5° C. Where the term "about" is used in the context of this invention (e.g., in combinations with temperature or molecular weight values) the exact value (i.e., without "about") is preferred.

As used herein, a "biologically active fragment" refers to a fragment of a reference sequence that has activity that is substantially equivalent to (e.g., at least 90% equivalent to) or greater than the activity of a reference sequence. For example, a biologically active fragment of a reference promoter would be a fragment that is capable of driving expression of a coding sequence at a substantially equivalent or higher level compared to the reference promoter.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

An "enhancer" is a nucleotide sequence that can stimulate promoter activity and can be an innate element of the promoter or a heterologous element inserted to enhance the level or tissue specificity of a promoter. The primary sequence can be present on either strand of a double-stranded DNA molecule, and is capable of functioning even when placed either upstream or downstream from the promoter.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g., if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

"Expression cassette" as used herein means a nucleic acid molecule capable of directing expression of a particular polynucleotide or polynucleotides in an appropriate host cell, comprising a promoter operably linked to the polynucleotide or polynucleotides of interest which is/are operably linked to termination signals. It also typically comprises polynucleotides required for proper translation of the polynucleotide or polynucleotides of interest. The expression cassette may also comprise polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the particular polynucleotide of the expression cassette does not occur naturally in the host cell and must have been introduced into the host cell or an ancestor of the host cell by a transformation process known in the art. The expression of the polynucleotide(s) in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

"Gene of interest" or 'nucleic acid of interest (NOI)" refers to any gene or NOI which, when transferred to a plant, confers upon the plant a desired characteristic such as antibiotic resistance, virus resistance, insect resistance, disease resistance, resistance to other pests, herbicide tolerance, improved nutritional value, improved performance in an industrial process or altered reproductive capability. The "gene of interest" or NOI may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element and/or coding sequences that do not naturally occur in association with that particular promoter, i.e., they are heterologous to the promoter.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a translation start site or transcription start site of a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

The terms "percent sequence identity" or "percent identity" are used interchangeably herein emboss.open-bio.org/html/adm/ch01s01 and is used herein refers to the percentage of identical nucleotides or amino acids in a linear polynucleotide or amino acid sequence of a reference ("query") sequence (or its complementary strand) as compared to a test ("subject") sequence (or its complementary strand) when the two sequences are optimally aligned. Optimal alignment of sequences for aligning a comparison window are known to those skilled in the art and may be conducted using known methods, e.g., using known software or computer programs such as the Smith and Waterman algorithm implemented in the EMBOSS-6.6.0 water tool using default matrix files EBLOSUM62 for protein, EDNAFULL for DNA with default gap penalties. EMBOSS-6.6.0 is available, e.g., from the following Bio-soft and Open-Bio such as at the following websites: en.bio-soft.net/format/emboss or emboss.open-bio.org/html/adm/ch01s01.

The terms "nucleic acid" or "polynucleotide" are used interchangeably herein and refer to any physical string of monomer units that can be corresponded to a string of nucleotides, including a polymer of nucleotides (e.g., a typical DNA polymer or polydeoxyribonucleotide or RNA polymer or polyribonucleotide), modified oligonucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated. The nucleic acid can be present in a vector, such as in a cell, virus or plasmid.

"Operably linked" refers to the association of polynucleotides on a single nucleic acid fragment so that the function of one affects the function of the other. For example, a promoter is operably linked with a coding polynucleotide when it is capable of affecting the expression of that coding polynucleotide (i.e., that the coding polynucleotide is under the transcriptional control of the promoter). Coding polynucleotide in sense or antisense orientation can be operably linked to regulatory polynucleotides.

The term "plant" refers to any plant, particularly to agronomically useful plants (e.g. seed plants), and "plant cell" is a structural and physiological unit of the plant, which comprises a cell wall but may also refer to a protoplast. The plant cell may be in form of an isolated single cell or a cultured cell, or as a part of higher organized units such as for example, a plant tissue, or a plant organ differentiated into a structure that is present at any stage of a plant's development. A plant may be a monocotyledonous or dicotyledonous plant species.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

"Plant tissue" as used herein means a group of plant cells organized into a structural and functional unit. Any tissue of a plant in planta or in culture is included. This term includes, but is not limited to, whole plants, plant organs, plant seeds, tissue culture and any group of plant cells organized into structural and/or functional units. The use of this term in conjunction with, or in the absence of, any specific type of plant tissue as listed above or otherwise embraced by this definition is not intended to be exclusive of any other type of plant tissue.

The term "promoter," as used herein, refers to a polynucleotide, usually upstream (5') of the translation start site of a coding sequence, which controls the expression of the coding sequence by providing the recognition for RNA polymerase and other factors required for proper transcription. For example, a promoter may contain a region containing basal promoter elements recognized by RNA polymerase, a region containing the 5' untranslated region (UTR) of a coding sequence, and optionally an intron.

"Regulatory elements" and "regulatory sequences" are used interchangeably herein and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translational enhancer sequences, introns, terminators, and polyadenylation signal sequences. They include natural and synthetic sequences as well as sequences which may be a combination of synthetic and natural sequences. Regulatory sequences may determine expression level, the spatial and temporal pattern of expression and, for a subset of promoters, expression under inductive conditions (regulation by external factors such as light, temperature, chemicals and hormones). Regulatory sequences may be short regions of DNA sequence 6-100 base pairs that define the binding sites for trans-acting factors, such as transcription factors. Regulatory sequences may also be enhancers, longer regions of DNA sequence that can act from a distance from the core promoter region, sometimes over several kilobases from the core region. Regulatory sequence activity may be influenced by trans-acting factors including general transcription machinery, transcription factors and chromatin assembly factors.

A "terminator" is responsible for the termination of transcription beyond the coding region and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Nontransformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as Pseudomonas HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone,); and genes conferring resistance to dicamba, such as dicamba monoxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example the maize homeobox gene knl, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107: 193-232; incorporated by reference).

In some embodiments of the disclosure, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140: 184-195) and a P106S mutation in goosegrass EPSPS (Baerson et al 2002, Plant Physiol 129: 1265-1275). Other sources of EPSPS which are not plant derived and can be used to confer glyphosate tolerance include but are not limited to an EPSPS P101S mutant from *Salmonella typhimurium* (Comai et al 1985, Nature 317: 741-744) and a mutated version of CP4 EPSPS from *Agrobacterium* sp. Strain CP4 (Funke et al 2006, PNAS 103: 13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83: 6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

The term "transformation" as used herein refers to the transfer of a nucleic acid into a host cell, preferably resulting in genetically stable integration, which includes integration into a chromosome and heritable extrachromosomal events. In some particular embodiments, the introduction into a plant, plant part and/or plant cell is via bacterial-mediated transformation, particle bombardment transformation (also called biolistic particle transformation), calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of a nucleic acid into the plant, plant part and/or cell thereof, or a combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in *Plant Molecular Biology and Biotechnology*, Glick, B. R. and Thompson, J. E., Eds. (CRC Press, Inc., Boca Raton, 1993), pages 67-88) and Rakowoczy-Trojanowska (Cell Mol Biol Lett 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

A "transgenic plant" is a plant having one or more plant cells that contain a heterologous DNA sequence.

As used herein, "vector" includes reference to a nucleic acid used in transfection of a host cell and into which can be inserted a polynucleotide. Vectors are often replicons. Expression vectors permit transcription of a nucleic acid inserted therein. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

DETAILED DESCRIPTION

Aspects of the disclosure relate to regulatory elements, such as promoters and terminators, useful for expression of heterologous sequences in plants, such as soybean.

In some aspects, the disclosure provides a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-57. In some embodiments, the nucleotide sequence comprises one or more of SEQ ID NOs: SEQ ID NOs: 1-57. In some embodiments, the nucleotide sequence comprises one of SEQ ID Nos: SEQ ID NOs: 1-57. In some embodiments, the disclosure provides a nucleotide sequence comprising a fragment, e.g., a biologically active fragment, of one or more of SEQ ID NOs: SEQ ID NOs: 1-57 (e.g., a fragment of at least 100, at least 200, at least 300, at least 400, at least 500, at least 600, at least 700, at least 800, at least 900 or at least 1000 contiguous nucleotides of one or more of SEQ ID NOs: 1-57). In some embodiments, the disclosure provides a nucleotide sequence comprising a fragment, e.g., a biologically active fragment, of one or more of SEQ ID NOs: 1-57 (e.g., a fragment of at least 100, at least 200, at least 300, at least 400, at least 500, at least 600, at least 700, at least 800, at least 900 or at least 1000 contiguous nucleotides of one or more of SEQ ID NOs: 1-57).

In some aspects, the disclosure provides an expression cassette. In some embodiments, the expression cassette comprises a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-57, wherein the nucleotide sequence is operably linked to a heterologous nucleotide sequence. In some embodiments, the expression cassette comprises a nucleotide sequence comprising one or more of SEQ ID NOs: SEQ ID NOs: 1-57. In some embodiments, the expression cassette comprises a nucleotide sequence comprising one of SEQ ID NOs: SEQ ID NOs: 1-57. In some embodiments, the expression cassette comprises a nucleotide sequence comprising a fragment, e.g., a biologically active fragment, of one or more of SEQ ID NOs: SEQ ID NOs: 1-57 (e.g., a fragment of at least 100, at least 200, at least 300, at least 400, at least 500, at least 600, at least 700, at least 800, at least 900 or at least 1000 contiguous nucleotides of one or more of SEQ ID NOs: SEQ ID NOs: 1-57). In some embodiments, the expression cassette further comprises a selectable marker.

In some embodiments, the heterologous sequence is a nucleic acid of interest that encodes an RNA or protein of interest. In some embodiments, the RNA or protein of interest is capable of conferring upon a plant a desired characteristic such as antibiotic resistance, virus resistance, insect resistance, disease resistance, resistance to other pests, herbicide tolerance, improved nutritional value, improved performance in an industrial process or altered reproductive capability. In some embodiments, the RNA or protein of interest comprises a genome editing agent, e.g., a CRISPR/Cas agent (such as a Cas protein and/or guide RNA), a TALEN, a DNA-guided nuclease, a meganuclease, a recombinase, or a zinc finger nuclease. In some embodiments, the heterologous nucleotide sequence encodes a selectable marker.

In some embodiments, the expression cassette is comprised within a vector, such as a plasmid, virus, or *Agrobacterium*. In some embodiments, the expression cassette is comprised within a plant cell. In some embodiments, the plant cell is a dicot cell. In some embodiments, the plant cell is a *Glycine max* cell. In some embodiments, the *Glycine max* cell is an elite *Glycine max* cell.

In some embodiments, the expression cassette is comprised within a transgenic plant. In some embodiments, the plant is a dicot. In some embodiments, the plant is a *Glycine max* plant. In some embodiments, the *Glycine max* plant is an elite *Glycine max* plant.

In some embodiments, the disclosure provides a seed from a transgenic plant, e.g., a seed comprising the expression cassette.

In some embodiments, the disclosure provides a commodity product produced from a transgenic plant or part thereof, e.g., a commodity product comprising the expression casssette. In some embodiments, the commodity product is selected from the group consisting of whole or processed seeds, flour, protein isolates, concentrates, liquids, syrups, pastes, sauces or other food or product.

Other aspects of the disclosure relate to a method, e.g., a transformation method, comprising introducing an expression cassette or vector as described herein into a plant or plant cell. In some embodiments, the introducing comprises *Agrobacterium*-mediated transformation. In some embodiments, the introducing comprises particle bombardment. In some embodiments of the method, the method further comprises placing the plant or plant cell under conditions whereby an RNA or protein of interest and/or a selectable marker is expressed from the expression cassette or vector. In some embodiments, the conditions are appropriate growth or maintenance conditions for the plant or plant cell. In some embodiments of the method, the method further comprises crossing the plant to a second plant to produce a progeny plant. In some embodiments of the method, the method further comprises self-crossing the plant to produce a progeny plant. In some embodiments, the plant or plant cell is a dicot plant or plant cell. In some embodiments, the plant or plant cell is a *Glycine max* plant or plant cell. In some embodiments, the plant or plant cell is an elite *Glycine max* plant or plant cell. In some embodiments, the second plant is an elite *Glycine max* plant.

Hereinafter, the present invention will be described in detail by the following examples. However, the following examples are illustrative of the present invention, and the scope of the present invention is not limited by the following examples.

EXAMPLES

Example 1: Identification of GmADF1 Candidate Promoter Sequences

Gene expression analysis was carried out using Affymetrix microarray dataset from the Syngenta Soy Gene Atlas (>50 tissue types) and from published expression profiling experiments using expression software, Genevestigator™. It was found that dozens of soybean genes are highly expressed throughout the different development stages and in all tested tissues. One of the highly expressed genes encodes Glyma09g02240, showing high homology with the ADF1 (ACTIN DEPOLYMERIZING FACTOR 1) family members which are functional in controlling actin-based cellular processes (see, e.g., Staiger et al., 1997, Profilin and actin-depolymerizing factor: modulators of actin organization in plants. Trends in plant Sciences 2:275-281; Bernstein and Bamburg, 2000, ADF/Cofilin: a functional node in cell biology. Trends in Cell Biology 20:187-195). The ADFs were first identified in plants and only share 28-35% identity with vertebrate ADF protein sequences. Typically, higher plants have a small family of ADF genes. For example, maize has one constitutive and 2 pollen-specific ADF genes (Lopez et al., PNAS, 93:7415-7420). The gene sequences corresponding to the identified highly expressed GmADF gene were retrieved from soybean variety Williams 82 genome. The predicted gene structure of GmADF1 (prADF1) is shown schematically in FIG. 1.

Example 2: Identification of Active Regulatory Sequences from GmADF1 Promoter by Transient Expression In order to identify the active GmADF1 promoter region from Glyma09g02240, different lengths of the GmADF1 upstream regulatory sequences, 5'-UTR region and the 1st intron sequences (prGmADF-01, SEQ ID NO: 1-4) were amplified from the soybean genomic DNA of Williams 82 variety. PCR products were purified and digested with HindIII and BamHI and cloned into a construct to form prGmADF1-ZsGreen-tNOS expression vectors.

Figure 2:
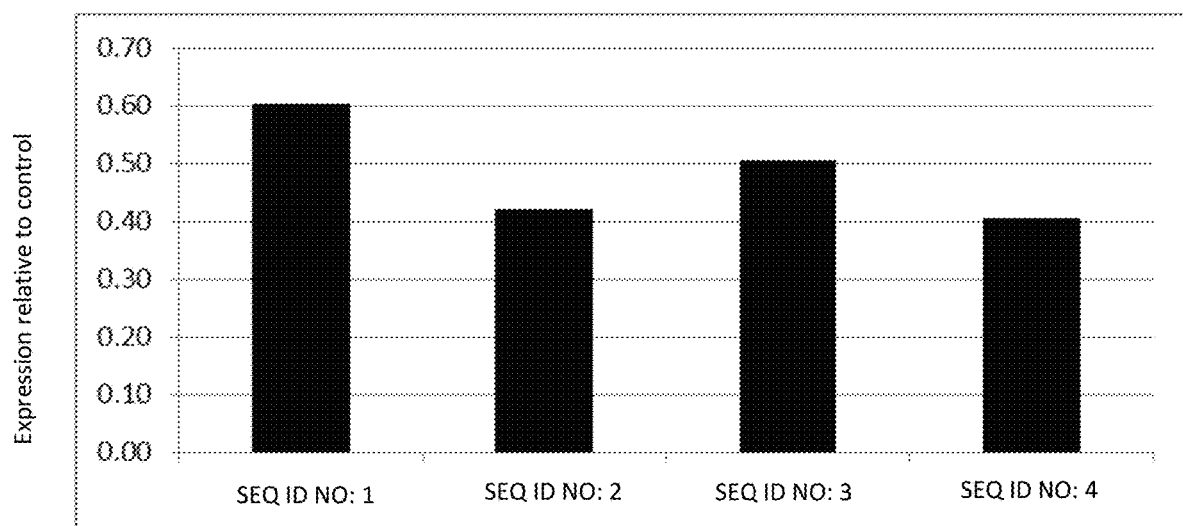
FIG. 2 is a graph showing the relative expression level of promoter activity of different GmADF sequences vs CMP promoter activity in bombarded immature cotyledons (CMP promoter activity is normalized to 1.00).

To assess the promoter activity of the different prGmADF sequences (SEQ ID NO: 1-4) in vivo, the different prGmADF promoter-ZsGreen-tNOS expression cassettes were released from vectors harboring these cassettes by restriction digestion. These prGmADF-ZsGreen-tNOS fragments were then purified and used for bombarding developing soybean cotyledons, which were isolated from soybean seeds of early R7 stage. For each bombardment (using the Bio-Rad™ PDS-1000/He Biolistic Particle Delivery System), 100 ng of the prCMP-AmCyan-tNOS cassette fragment was used as the loading control on 1um gold particles. The negative control of the experiment used gold particles loaded only with the control DNA lacking fluorescent protein gene. For GmADF promoter, the amount of prGmADF-ZsGreen-tNOS cassette fragment used was at the equal molar of 200 ng of a prCMP-ZsGreen-tNOS cassette fragment. prCMP-ZsGreen-tNOS cassette serves as the positive control and its fluorescence signal intensity is treated as 100% of activity. Two days after bombardment, CCD images were obtained using Olympus™ OV100 imaging system for GFP and CFP channels, and the intensity of GFP and CFP signals from transformed cotyledon cells was collected after background subtraction. The intensity of GFP signals on bombarded soybean cotyledons was used as the indicator for GmADF promoter activity. GFP or CFP intensity from 10 most bright cells in each image frame was collected. The average intensity of GFP signals was first normalized by the average intensity of CFP signals from the same experiment, and then compared with the data from prCMP-ZsGreen-tNOS positive control (FIG. 2). Transient expression shows that prGmADF sequences confer excellent promoter activity which is about 40%-60% of the positive control prCMP, which is a strong promoter, in the immature soybean cotyledon tissue (FIG. 2). The 1st intron seems to enhance the promoter activity since the intron-containing sequences SEQ ID NO: 1 and SEQ ID NO: 2 have somewhat higher activity compared to their respective intron-less counterpart SEQ ID NO: 3 and SEQ ID NO: 4.

Example 3: A Modified GmADF Promoter Sequence, prGmADF-02

Figure 3:
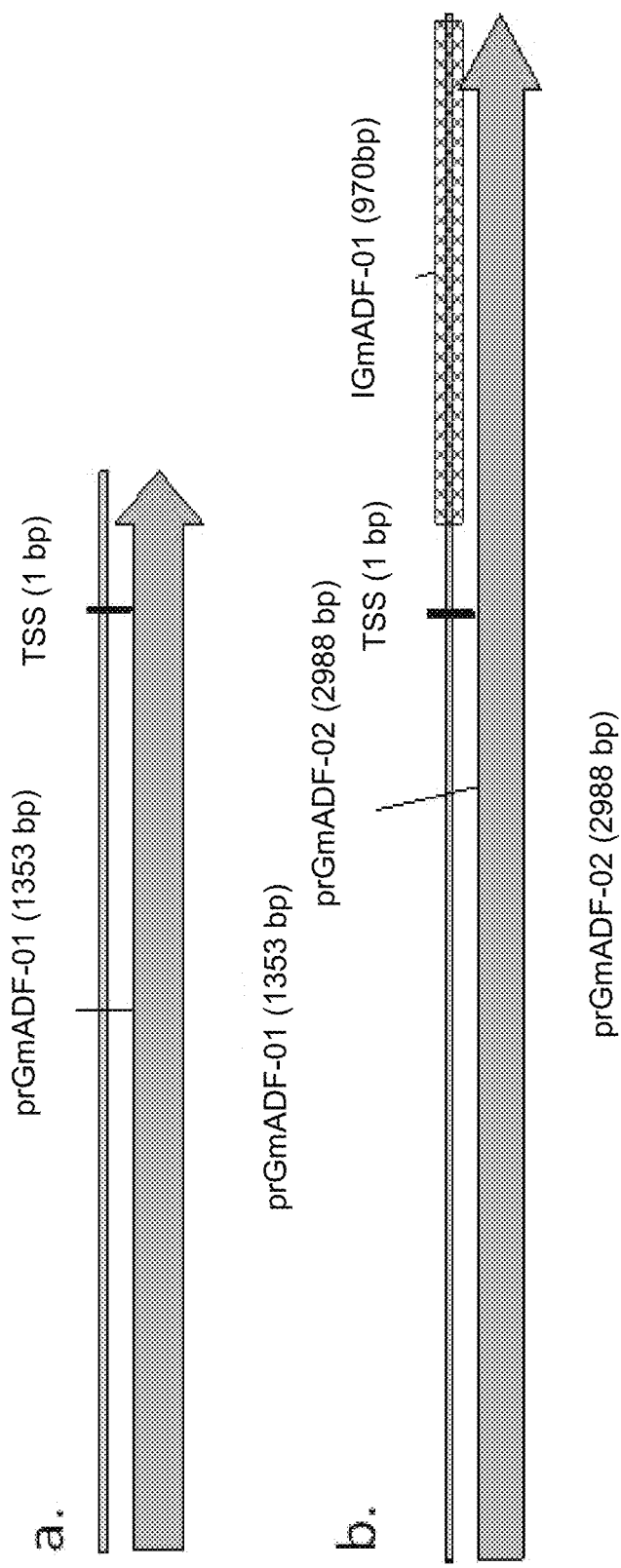
FIG. 3 is a schematic of the gene structure of the highly expressed prGmADF-01 (SEQ ID NO: 1) and prGmADF-02 (SEQ ID NO: 5) promoter sequences.

There is a long intron right after the start codon which is present in the exon 1. As discussed above it is believed that the 1st intron is helpful for higher level of gene expression. In order to include this intron as part of the promoter regulatory sequences, an ATG was mutated to a CTG sequence thus removing the start codon. The resulting regulatory sequence pGmADF-02 (SEQ ID NO: 5) is shown schematically in FIG. 3.

prGmADF-02 contains 2 kb upstream of the translation start site plus sequences of exon1, intron1 and 15 bp of exon2. For cloning purpose, prGmADF-02 was divided into two parts: P1 and P2 fragments. The BsmBI (compatible with AscI)/BsmBI ("A" in 2001 location was mutated into "C") P1 and the BsmBI (compatible with P1 3' sticky end)/BsmBI (compatible with SpeI) P2 were amplified from soybean (Williams 82) genomic DNA with primers introducing BsmBI in both end, respectively. The P1 and P2 fragments were cut out by BsmBI and purified, then these two fragments were cloned into a backbone (AscI/SpeI digested, and then purified the 9207 bp fragment) to form binary vector which contains the prGmADF-02-GUS-tNOS expression cassette and prCMP-PAT-tNOS selectable marker cassette.

Example 4: Use of Regulatory Sequences from GmADF1 Promoter for Driving Expression of Gene of Interest in Stable Transgenic Tobacco and Soybean Plants Through site-directed mutagenesis, a SpeI site was introduced into the construct between the KpnI and EcoRI sites after the NOS-terminator. The AmCyan-tNOS fragment was then cut from the resulting plasmid between AgeI and SpeI sites. The second fragment, prGmADF-01 (SEQ ID NO: 4), was cut from a construct using AscI and AgeI. Both fragments, after gel-purification, were cloned into a construct between AscI and SpeI sites by three-fragment ligation to form a binary vector for tobacco and soybean transformation, which contains prGmADF-01-AmCya-tNOS and a hygromycin selectable marker. A binary vector with prADF-02-GUS expression cassette and PAT selectable marker was created as described in Example 3 for tobacco and soybean transformation. The binary vectors were introduced into *Agrobacterium* strain LBA4404 and EHA101 by electroporation. The resulting strains were used for *Agrobacterium*-mediated transformation of tobacco and soybean, respectively. Stable transgenic tobacco and soybean were generated using glufosinate or hygromycin selection as described (see Chilton and Que 2003, Plant Physiol 133: 956-965, Hwang et al WO08112044, Que et al WO08112267). Transgenic plants were assayed for reporter gene expression and were found to drive high level expression of AmCyan and GUS expression.

Example 5: Use of GmADF Promoter in Driving Herbicide Tolerance Gene in Transgenic Soybean Plants The prGmADF-01 promoter sequence was PCR amplified from a plasmid with primers introducing BsmBI (compatible with KasI) at 5'-end and BsmBI (compatible with BglII) at 3'-end, then digested by BsmBI, and cloned to another backbone (KasI/BglII digested). The positive clones were verified by KasI/BglII digestion. The PCR fragment and both cloning junctions were confirmed by sequencing. The resulting binary vector contained prGmADF-01 driving EPSPS (5-enolpyruvylshikimate-3-phosphate synthase) and was transformed into *Agrobacterium* strain EHA101 and the resulting strain was used to transform soybean variety Jack using glyphosate as selection. Transgenic events were generated from the binary vector using imbibed dry seeds as target tissue as described (Khan US2004034889). Transgenic plants were analyzed by Taqman assay to determine transgene copy number. Table 1 shows that prGmADF-01 promoter driving EPSPS expression resulted in high transformation frequency, similar to a control in which a very strong viral promoter prCMP was used to drive expression of EPSPS gene. This result is surprising considering that in transient expression studies, expression of ZsGreen driven by prGmADF is only 40% to 60% of that by prCMP. Without wishing to be bound by theory, it is possible that prGmADF is more active than prCMP in certain stages of development where prCMP is not very active, such as meristematic tissues where glyphosate is particularly damaging.

TABLE 1

Soybean Transformation Efficiency of different promoters driving EPSPS gene using glyphosate selection

| EPSPS Selectable Marker Cassette | Transformation Frequency |
| --- | --- |
| eFMV-prCMP-cmEPSPSpt-tPsE9 | 19.0% |
| eFMV-prGmADF-01-cmEPSPSpt-tPsE9 | 22.19% |

In summary, the above results described in Examples 1-5 indicate that use of soybean ADF regulatory sequences (SEQ ID NO: 1-5) can drive high levels of expression of a gene of interest. The prGmADF promoter also allows for recovery of high transformation efficiency when an herbicide is used as a selection agent indicating a high level of herbicide tolerance.

Example 6: Cloning and Evaluation of Soybean Promoter Candidates Using Soybean Cotyledon Transient Assay and Digital Imaging System Introduction In the past, limited options were available to influence the choice of good constitutive promoters for use in generating soybean transgenic events. The main tools available for driving expression of selectable marker and trait genes were Cestrum Leaf Yellow Curling Virus (CmYLCV) promoter (aka. CMP promoter) and several viral enhancers, such as the Cauliflower Mosaic Virus 35S enhancer (e35S), and an enhancer from Figwort Mosaic Virus (FMV). As a consequence, the practice of generating soybean GM products was constrained during the design of binary vectors for transformation. As a result, candidate promoters were identified and tested as described below to identify new promoters that provide constitutive activity.

Methods

Candidate promoter sequences were amplified from Williams 82 genomic DNA using high fidelity Phusion enzyme (New England Biolabs™). The PCR products were digested with BstXI or HindIII at the 5' side, and with AgeI or BamHI at the 3' side before cloned into a cloning vector to swap out prCMP with each candidate promoter. In the resulting constructs, the promoter fragments drove the expression of the ZsGreen gene, making new promoter-ZsGreen-tNOS cassettes for promoter activity tests. All promoter sequences were verified by sequencing before testing.

For the transient assay, the soybean cotyledons were used from seeds of early R7 reproductive stage. Soybean cotyledons were separated from seed pods and placed in a circle on ½ Murashige and Skoog's (MS) medium with the flat side facing up under sterile conditions. A Bio-Rad PDS-1000/He Biolistic Particle Delivery System was used for bombardment. For each experiment, 100 ng of the prCMP-AmCyan-tNOS cassette fragment from a control construct was used as the DNA loading control on 1 μm gold particles. The negative control of the experiment used gold beads loaded with the prCMP-AmCyan-tNOS cassette fragment only. The positive control of the experiment used gold beads loaded with 100 ng of the prCMP-AmCyan-tNOS cassette fragment plus 200 ng of the prCMP-ZsGreen-tNOS cassette fragment from a second control construct. For each promoter, in addition to 100 ng of the prCMP-AmCyan-tNOS cassette fragment, the amount of promoter-ZsGreen-tNOS cassette fragment was loaded at equal molar concentration as 200 ng prCMP-ZsGreen-tNOS cassette fragment. Bombardment was carried out using standard procedures.

Soybean cotyledon pictures were taken and processed as stated in the results (Transient Assay Development section). For quantification, GFP or CFP intensity readings were collected from the 15-20 brightest cells in each picture frame. After elimination of the outliers in the subset detected by the Grubb's test (Grubbs, (1969) Procedures for detecting outlying observations in samples. Technometrics, 11, 1-21.), measurements from the top ten cells were used to calculate the expression level of each promoter candidate. The average intensity of the GFP signal was normalized by the average intensity of CFP signal from the same picture. The resulted value was then used to compare with the value from the treatment using control prCMP-ZsGreen-tNOS.

Tobacco and soybean transformation experiments were conducted following standard *Agrobacterium*-mediated transformation protocols (see Chilton and Que 2003, Plant Physiol 133:956-965, Hwang et al WO08112044, Que et al WO08112267).

Results
Candidate Gene Selection

Figure 4:
FIG. 4 is a graph showing the average gene expression of candidate promoters. Errors bars represent standard deviation.

Two searches for strong and constitutive promoter candidates were performed by studying whole genome-based soybean transcriptome dataset generated with Affymetrics Microarray Genechip using soybean plant samples from major organ types across developmental stages. Data was first analyzed from a total of 167 chips covering all tissues and at all stages of soybean development and selected a set of 66 probesets (group 1) that showed a pattern of constitutive expression (average signal greater than 2000 and variance filter 0.02). When plotting Average Gene Expression signal against Standard Deviations (STD) for each candidate, it appeared that although these candidates were expressed at similar levels across all tissues and at all developmental stages, the average gene expression levels of most of the candidates were below 12,000 reads. Since promoters that confer strong expression of a selectable marker gene in younger tissues are more likely to be useful for transformation practice, 66 chips that covered non-root tissues and at early soybean developmental stages were picked out from the 167 chips and used for performing a second search using the same statistical criteria as the first search. From the second search, a subset of 105 probesets (group 2) were identified by 2D-hierarchical clustering analysis that showed a pattern of high constitutive expression (average expression value greater than 12000 reads). Twenty-two genes appeared in both candidate groups. From these groups, three group 1 promoter candidates, eight group 2 promoter candidates, and eleven candidates shared by both groups, were cloned and tested (FIG. 4, Table 2).

TABLE 2

List of tested promoter candidates and their corresponding genes

| Promoter code | SEQ ID NO | Corresponding Gene |
|---|---|---|
| p01 | 6 | Putative plasma membrane intrinsic protein (PIP1) aquaporin. |
| p10 | 7 | Actin depolymerizing factor 1 (ADF1) |
| p11 | 8 | Cyclophilin (Cyp) |
| p12 | 9 | Subi-1 gene for ubiquitin |
| p14 | 10 | No apparent homology |
| p28 | 11 | Glycogen synthase kinase (GSK-3) |
| p30 | 12 | Homologous to elongation factor (EF1) |
| p31 | 13 | Chloroplast photosystem II PsbR |
| p32 | 14 | Glyceraldehyde-3-phosphate dehydrogenase (GAPC) |
| p33 | 15 | Ubiquitin-conjugating enzyme |
| p35 | 16 | Homologous to putative DNA binding protein |
| p36 | 17 | Ubiquitin-conjugation enzyme |
| P37 | 18 | S-adenosylmethionine synthetase (SAMS) |

Transient Assay Development and Results

A DNA bombardment method was used to deliver test constructs into cotyledons isolated from soybean immature seeds. For the bombardment experiments, a prCMP-AmCyan-tNOS cassette fragment was used as the gene delivery control. The negative control of the experiment used gold beads only loaded with the prCMP-AmCyan-tNOS cassette fragment. The positive control of the experiment used gold beads loaded with prCMP-ZsGreen-tNOS cassette fragment, as the treatment having 100% activity, additional to the prCMP-AmCyan-tNOS cassette fragment.

For all promoter candidates, the promoter fragments were amplified by PCR from genomic DNA of soybean variety Williams 82. The fragments were cloned to drive the expression of a ZsGreen reporter gene. For intron-free candidates, the promoters were ~2 kb fragments upstream of the predicted start codon. For candidate genes having one or multiple introns, the corresponding promoter fragments contained ~2 kb fragment upstream of the predicted start codon or the first intron, plus components covering the first exon, intron, and 16-18 base pairs of the second exon. Base pairs of the second exon were determined to ensure in-frame fusion of the partial candidate gene product with the reporter ZsGreen gene. Because the fusion proteins contained a six amino acid-linker sequence (Asp-Pro-Pro-Val-Ala-Thr), the activity of the ZsGreen protein was not expected to be significantly affected. All promoter sequences were verified by sequencing before testing. In the tests, the amount of each promoter-ZsGreen-tNOS cassette fragment was loaded at equal molar concentration as the prCMP-ZsGreen-tNOS positive control.

For each promoter candidate, six soybean cotyledons were placed in a circle on ½ Murashige and Skoog's (MS) medium with the flat side facing up for bombardment and imaging. Pictures were taken using Olympus™ OV100 imaging system two days post bombardment, making sure that each picture included both the soybean cotyledon surface area, and a blank space in the picture as background. For each bombardment experiment, pictures having the most CFP (product of AmCyan expression) spots were chosen for analysis. Background subtraction was applied before choosing spots for quantification. Overlay of CFP and GFP (product of ZsGreen expression) signals suggested that different cotyledon cells received different amounts of AmCyan and ZsGreen reporter genes during bombardment, and therefore could be quantified independently. For quantification, GFP or CFP intensity readings were collected from the 15-20 brightest cells in each picture frame. Measurements from the top ten cells were used to calculate the expression level of each promoter candidate. The average intensity of the GFP signal was normalized by the average intensity of CFP signal from the same picture. The resulting value was then compared to the value from the positive control treatment using prCMP-ZsGreen-tNOS.

Figure 5:
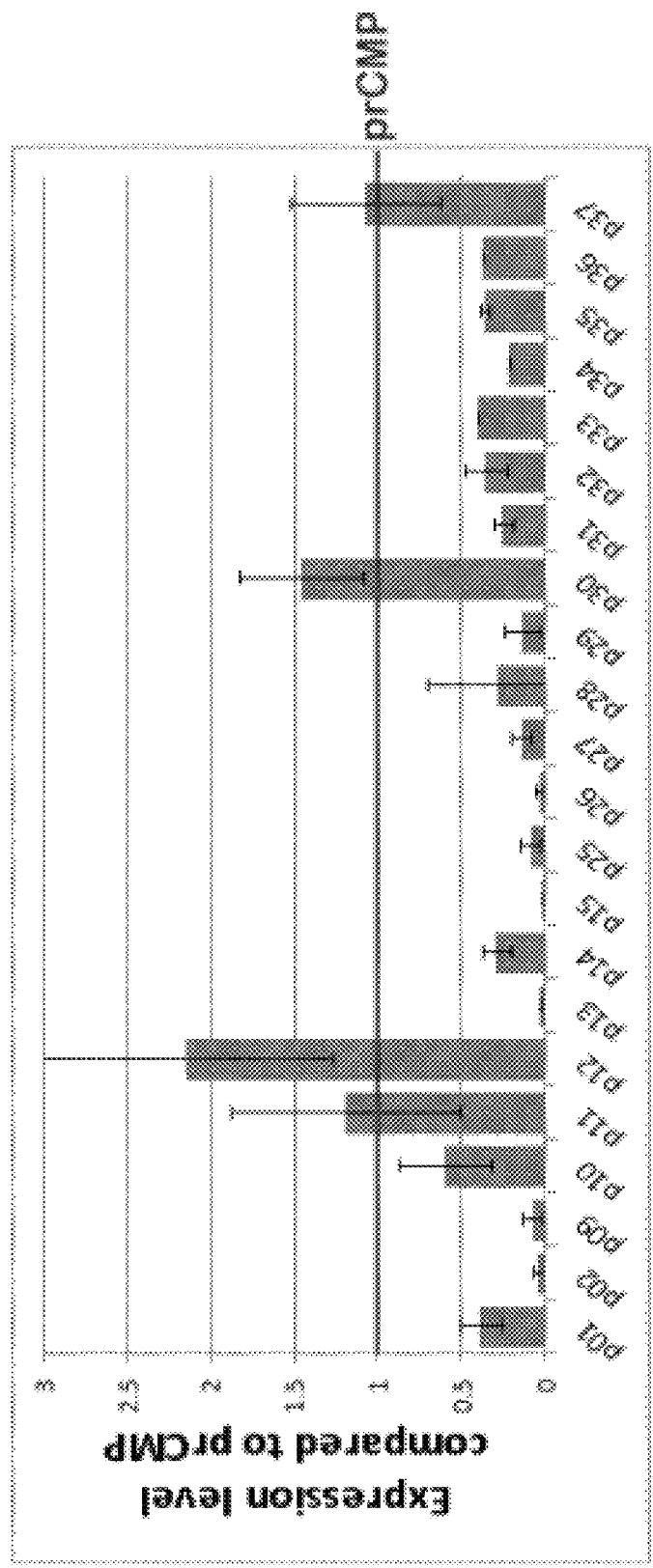
FIG. 5 is a graph showing the relative promoter activities compared to control promoter prCMP. The error bars represent the standard deviation for p01, 09, 10, 11, 12, 14, 28, 29, 31, and 37, but represent distance from the mean for p02, 25, 26, 27, 30, 32, and 35. Experiments for p13, 15, 33, 34, and 36 were not repeated, but similar results were observed when testing alternate variants.

A total of 22 promoter candidates were tested in separate experiments, some were tested three times, and some were tested only once or twice. Because all experiments used prCMP-ZsGreen-tNOS as 100% activity control, results from all these experiments were compiled and presented in one graph (FIG. 5). The promoters p10, p11, p12, p30 and p37 have moderate to strong activity in soybean cotyledons relative to prCMP. The promoters p01, p14, p31, p32, p33, p35, and p36 have lower but reproducibly detectable levels of activities in soybean cotyledons. Table 2 presents genes in the soybean genome driven by these functional promoter candidates. The promoters p2, p9, p13, p15, p26, p27, p28, p29, and p34 did not exhibit detectable, or reproducibly detectable activities, in these transient experiments.

Figure 6:
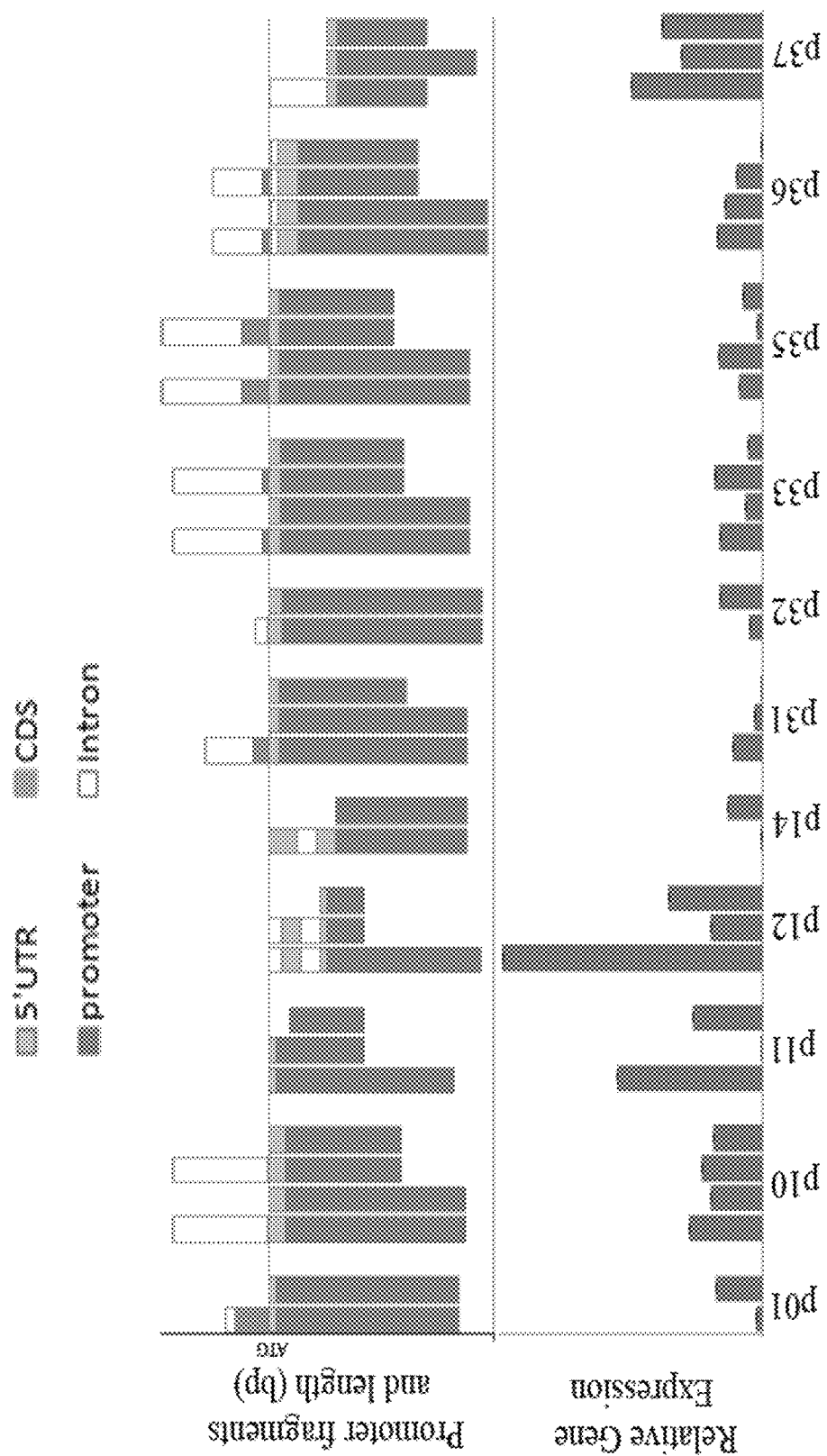
FIG. 6 is a graph showing relative activity of promoter variants. The upper panel shows the length and nature (promoter, 5'UTR, CDS, and intron) of covered region for each promoter variant. The lower panel shows relative promoter activities for each variant in the assay.

Shorter variants for some of these promoters were also tested using the assay (FIG. 6 and Table 3, the promoter order in Table 3 as read top to bottom is the same as the promoter order in FIG. 6 as read left to right). A correlation between specific introns in promoters and ZsGreen intensity was observed. For instance, introns in promoters p10, p31, p33, p36, and p37 have a positive effect on ZsGreen intensity, whereas introns of p01, p12, p14, p32, and p35 have a negative effect on ZsGreen intensity. These results suggested roles of introns in these promoters in regulating gene expression levels, and helped defining optimal fragment for each promoter to drive the expression of genes of interest.

TABLE 3

Promoter sequences and shorter variants

| Promoter code | SEQ ID NO | Description |
|---|---|---|
| p01 | 6 | Full length |
| p01v2 | 19 | Truncated form with part of 3' sequence removed |
| p01v3 | 42 | Truncated form with part of 5' sequence removed |
| p10 | 7 | Full length |
| p10v2 | 20 | Truncated form with part of 3' sequence removed |
| p10v3 | 21 | Truncated form with part of 5' sequence removed |
| p10v4 | 22 | Truncated form with part of 5' sequence removed and part of 3' sequence removed |
| p11 | 8 | Full length |
| p11v2 | 23 | Truncated form with part of 5' sequence removed |
| p11v3 | 24 | Truncated form with part of 5' sequence removed and part of 3' sequence removed |
| p12 | 9 | Full length |
| p12v2 | 25 | Truncated form with part of 5' sequence removed |
| p12v3 | 26 | Truncated form with part of 5' sequence removed and part of 3' sequence removed |
| p14 | 10 | Full length |
| p14v2 | 27 | Truncated form with part of 3' sequence removed |
| p28 | 11 | Full length |
| p28v2 | 51 | Truncated form with part of 3' sequence removed |
| p28v3 | 52 | Truncated form with part of 5' sequence removed and part of 3' sequence removed |
| p31 | 13 | Full length |
| p31v2 | 28 | Truncated form with part of 3' sequence removed |
| p31v3 | 29 | Truncated form with part of 5' sequence removed and part of 3' sequence removed |
| p32 | 14 | Full length |
| p32v2 | 30 | Truncated form with part of 3' sequence removed |
| p33 | 15 | Full length |
| p33v2 | 31 | Truncated form with part of 3' sequence removed |
| p33v3 | 32 | Truncated form with part of 5' sequence removed |
| p33v4 | 33 | Truncated form with part of 5' sequence removed and part of 3' sequence removed |
| p35 | 16 | Full length |
| p35v2 | 34 | Truncated form with part of 3' sequence removed |
| p35v3 | 35 | Truncated form with part of 5' sequence removed |
| p35v4 | 36 | Truncated form with part of 5' sequence removed and part of 3' sequence removed |
| p36 | 17 | Full length |
| p36v2 | 37 | Truncated form with part of 3' sequence removed |
| p36v3 | 38 | Truncated form with part of 5' sequence removed |
| p36v4 | 39 | Truncated form with part of 5' sequence removed and part of 3' sequence removed |
| P37 | 18 | Full length |
| p37v2 | 40 | Truncated form with part of 3' sequence removed and additional 5' sequence |
| p37v3 | 41 | Truncated form with part of 3' sequence removed |

Stable Transformation Tests and Results

Several of these promoters were put into binary vectors to drive the expression of selectable marker genes and were tested in stable transformation experiments. The selectable marker genes and expression elements in these constructs are shown in Table 4.

TABLE 4

Binary vectors with expression elements for testing in stable transformation experiments

| Construct | Enhancers | Promoter | Selectable Marker Gene | Terminator |
|---|---|---|---|---|
| 19363 | eFMV, e35S, | prCMP | cmEPSPSpt | tNOS |
| 19437 | eFMV, e35S | prGmSAMS | cmEPSPSpt | tNOS |
| 19502 | eNOS, eFMV, | prGmEPSPS | cmEPSPSpt | tGmEPSPS |
| 19501 | eFMV, e35S | prGmEF (p30) | cmEPSPSpt | tGmEPSPS |
| 19583 | eFMV | prAtEF1aA1 | cCP4EPSPSCTP2 | tPsE9 |
| 19800 | eFMV, eNtADH | prCMP | cCP4EPSPSCTP2 | tPsE9 |
| 19809 | | prGmUbi1 | cCP4EPSPSCTP2 | tPsE9 |
| 19646 | eFMV | prGmSAMS | cCP4EPSPSCTP2 | tPsE9 |
| 19647 | eFMV | prGmADF | cCP4EPSPSCTP2 | tPsE9 |
| 19744 | eFMV | prGmEF (p30) | cCP4EPSPSCTP2 | tPsE9 |
| 19763 | eFMV | prGmEPSPS | cCP4EPSPSCTP2 | tPSE9 |

Key
eFMV    Enhancer from Figwort mosaic virus (FMV)
e35S    Enhancer from Cauliflower mosaic virus (CMV)
eNOS    Putative enhancer sequence
eTMV    Enhancer from Tobacco mosaic virus (TMV)
eNtADH    Enhancer, 5'UTR of tobacco alcohol dehydrogenase gene (ADH).
prCMP    Promoter from Cestrium Yellow Leaf Curling Virus
prGmEPSPS    Promoter from Soybean native EPSPS gene
prAtEF1aA1    Promoter from *A. thaliana* EF-1 (for elongation factor alpha) A1 gene (prAtTsf1)
cmEPSPSpt    Plastid targeted soybean codon optimized class 2 *A. tumafaciens* EPSPS
cCP4EPSPSCTP2    *Arabidopsis* CTP2 (Chloroplast transit peptide) and CP4EPSPS (Roundup Ready, RR2) fusion.
tNOS    Synthetic Nopaline synthetase terminator
tPsE9    3'-UTR of the pea (*Pisum sativum*) rib-1,5-bisphosphate carboxylase (rbcS2) small subunit E9.
tGmEPSPS    An EPSPS terminator from *Glycine max*

Figure 7A:
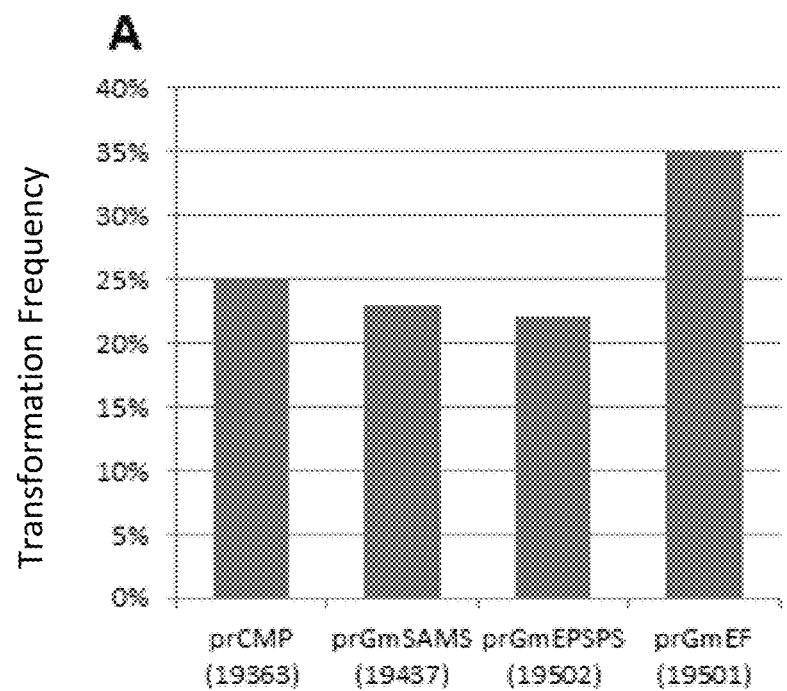
FIGS. 7A-7C are graphs showing promoter activities in driving selectable marker gene expression for stable transformation in tobacco and soybean. Promoter activities were reflected by the transformation frequency (TF) in tobacco (FIG. 7A) and soybean (FIGS. 7B and 7C) Numbers in parentheses are construct numbers from Table 4.

To survive the selection and regeneration processes, selectable marker gene need to be expressed at levels above certain thresh hood in transgenic plants. Therefore, transformation frequency (TF, number of transgenic events/number of explants) in these experiments reflected promoter activities. Constructs 19363, 19437, 19502, and 19501 were tested in tobacco transformation (FIG. 7A). The promoter prGmSAMS (p37 in FIG. 5) exhibited activities comparable to prCMP with an extra enhancer when driving expression of the selectable marker gene EPSPS. The promoter prGmEF (p30 in FIG. 5) exhibited activities higher than that of native EPSPS promoter (prGmEPSPS) with extra enhancers.

Figure 7B:
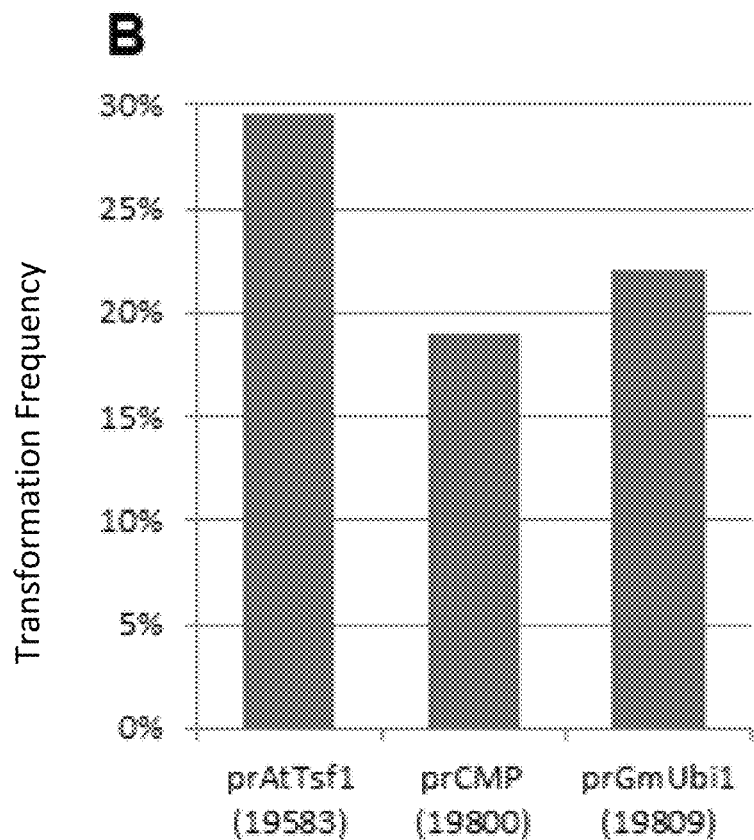
Figure 7C:
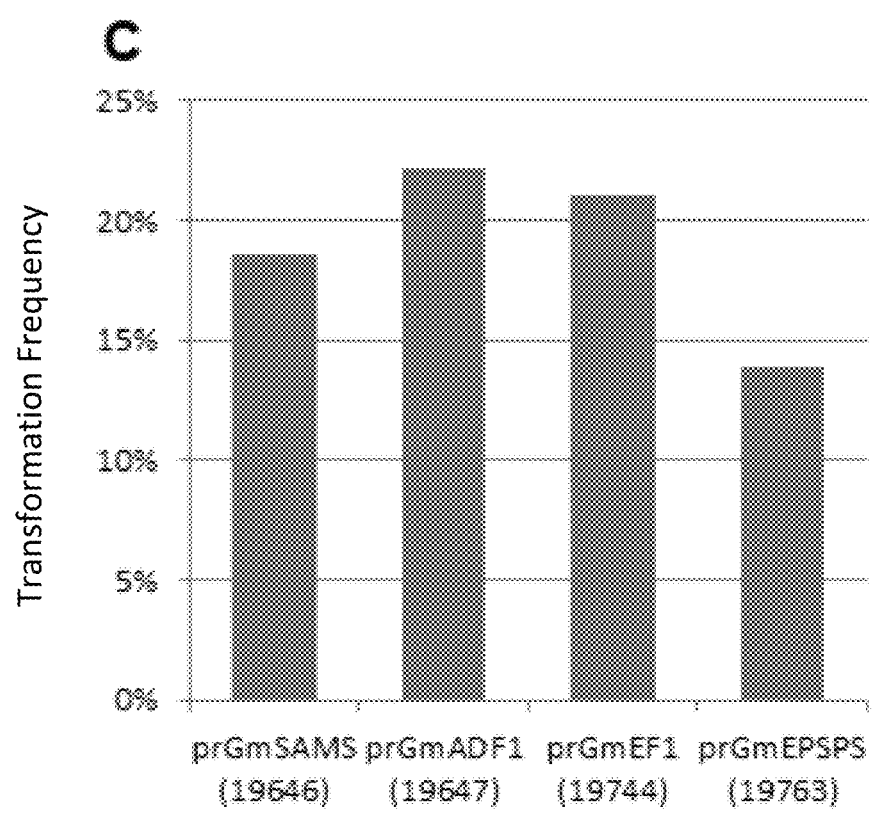

Constructs 19583, 19800, 19809, 19646, 19647, 19744, and 19763 were tested in soybean transformation (FIG. 7B-C). In the absence of enhancer elements, prGmUbi1 (p12 in FIG. 5) did not perform as well as the elongation factor 1-alpha promoter from Arabidopsis thaliana (prAtEF1aA1 aka. prAtTsf1), but was better than prCMP with an extra enhancer, when driving expression of the selectable marker gene CP4EPSPSCTP2 (aka. RR2 for Roundup Ready 2, FIG. 7B). In FIG. 7C, promoters prGmADF1 (p10 in FIG. 5), prGmEF1, and prGmSAMS all exhibited activities higher than prGmEPSPS, when driving the expression of the selectable marker for soybean transformation.

These data from transformation experiments support the transient results, indicating that promoters prGmSAMS, prGmEF, prGmUbi1, and prGmADF are active and strong, efficient in driving selectable marker genes for transformation. Therefore, these promoters are new options that can be used in generating soybean transgenic plants to drive the expression of selectable marker genes and potential trait genes. The other promoters described in this example may also be used to drive expression of selectable marker genes and potential trait genes.

Example 7: Additional Promoter Sequences

Additional promoter sequences were developed and are shown in Table 5. These promoters have also been used to drive expression of reporter, selectable marker, or trait genes in stably transformed plants and have been shown to have various levels of expression appropriate for expression of the applicable type of transgene. The strongest performing promoters from Table 5 included prGmADF-03, prGmADF-04, prGmCypCMP-03, and prGmSAMS-03. Accordingly, the promoters in Table 5 may be used to drive expression of, e.g., selectable marker genes and potential trait genes.

TABLE 5

Additional promoter sequences

| Promoter Name | SEQ ID NO |
| --- | --- |
| prGmPIP-02 | 43 |
| prGmADF-02 | 44 |
| prGmADF-03 | 45 |
| prGmADF-04 | 46 |
| prGmCyn-02 | 47 |
| prGmCypCMP-01 | 48 |
| prGmCypCMP-02 | 49 |
| prGmCypCMP-03 | 50 |
| prGmSAMS-02 | 53 |
| prGmSAMS-03 | 54 |
| prGmGAPDH2-01 | 55 |
| prGmGAPDH3-01 | 56 |
| prGmGSK3-01 | 57 |

REFERENCES

US20160237445
WO2007107516
CN103667296B
U.S. Pat. No. 6,204,373

What is claimed is:

1. An expression cassette comprising a nucleotide sequence having at least 95% identity with one or more of SEQ ID NOs: 1, 5, 7, 44 and 45, wherein the nucleotide sequence is operably linked to a heterologous nucleotide sequence.

2. The expression cassette of claim 1, wherein the nucleotide sequence comprises any one of SEQ ID NOs: 1, 5, 7, 44 and 45.

3. The expression cassette of claim 1, wherein the heterologous nucleotide sequence is a nucleic acid of interest that encodes an RNA or protein of interest.

4. The expression cassette of claim 3, wherein the RNA or protein of interest is capable of conferring upon a plant a desired characteristic selected from the group consisting of antibiotic resistance, virus resistance, insect resistance, disease resistance, resistance to other pests, herbicide tolerance, improved nutritional value, improved performance in an industrial process and altered reproductive capability.

5. The expression cassette of claim 1, wherein the heterologous nucleotide sequence encodes a selectable marker or wherein the expression cassette further comprises a selectable marker.

6. A vector comprising the expression cassette of claim 1.

7. The vector of claim 6, wherein the vector is a plasmid, virus, or *Agrobacterium* cell.

8. A plant cell comprising the expression cassette of claim 1.

9. The plant cell of claim 8, wherein the plant cell is a dicot cell.

10. The plant cell of claim 9, wherein the plant cell is a *Glycine max* cell.

11. A transgenic plant comprising the plant cell of claim 9.

12. The transgenic plant of claim 11, wherein the plant is a dicot.

13. The transgenic plant of claim 12, wherein the plant is a *Glycine max* plant.

14. A seed from the transgenic plant of claim 11, comprising the expression cassette of claim 1.

15. A method, comprising introducing the expression cassette of claim 1 into a plant or plant cell.

16. The method of claim 15, further comprising placing the plant or plant cell under conditions whereby an RNA or protein of interest and/or a selectable marker is expressed from the expression cassette.

17. The method of claim 15, further comprising crossing the plant to a second plant or self-crossing the plant to produce a progeny plant.

18. A transgenic plant produced by the method of claim 15, or a plant part thereof.

19. The transgenic plant, or part thereof, of claim 18, wherein the plant is a *Glycine max* plant.

* * * * *

SEQUENCE LISTING

```
<160> NUMBER OF SEQ ID NOS: 57

<210> SEQ ID NO 1
<211> LENGTH: 2999
<212> TYPE: DNA
<213> ORGANISM: Artificial Sequence
<220> FEATURE:
<223> OTHER INFORMATION: Synthetic polynucleotide

<400> SEQUENCE: 1
gtgaatataa agggcaccgc tcgttgttga tgagaacacg aaatctcctc tccacaatgc      60
aacgtcaaga tgtcatagac aggtatggaa aggaaaaata aataaataaa taaatggatt     120
ttatgctcca cccagtttgc ccttcctgaa tgctaacaaa actcaacatg tttttgaata     180
gggtaataat cggggttggt ttttgttgt tctcccttgc tgttctttat gttgtttcca     240
agcgaattgg actacttacg ttgcaaagaa aggttactga ggccataaaa gctggtatgg     300
tgggacaggc agagctaagg ccccaagctg ttgcagatga cgtgaatctt catcaagtca     360
gaggcaatcg tgttcctaat aatgcagagg ctcctttaga acaaagaatc catgatgaac     420
tatgatgcat ttctaagcaa tactatcatg ttatgtgtgt ttataacaca actcttctaa     480
ttcctttaaa agtaacgaaa gtaaaaagta ttttgctatc ttgagagttc gaaaagcatt     540
taatactacc tttttgagaa ttattggctg atctgttata atgaattaaa aattctttct     600
gtagttgttt ttgtctacgc tacaggcctt tcaacatgag caagctaata attgttgacg     660
```

```
agctgtctct ggctgctttt tcattgtacc aatgcttgtc tcctacacat caactgtatt    720
taagatctga agctgacatg agattttaca aagcattata taattacatt ggcgccacaa    780
taatttcgag atatttatca aaataaataa agttgcaaat gcaatggag ttcacatgca    840 atgaatccct tgtcataaac tccaaaatca tgattgcaac ataaacaaat gttttagaaa    900
aattaaaatc tgtggcttac gccctcatgc acatgttttg cgtgatgatt aacagttgtt    960
acagctccct ctttctgagt cgtggtaatt tgaggtaaat ttgcgtgatg aactagtaag    1020
ttttattttc cagtgaagca actgctacag gcttgggtgt tggagaaatt taccattgag    1080
ttatgcaata gttacctgga ttatccttac tttttataat agaaaaataa tccttttaat    1140
aaactcgttt agattctgtt tatacaaatt tggtagatta aacaaattat cacgtgacac    1200
aaatatttct atgattgctt aaaatagaat aaaagaatt tagttgaaat tgttttttat    1260
actgttgatt ttgaatagaa taatatggta aaatggtcaa ttcttattgg atatttatgt    1320
aagaatattt tgcattgaaa ttgtctagaa tattttaga catataatat gatgggtaaa    1380
taatggtgtc cttcgaagtg tatgataaaa gattcatttc ttagactcat gtatagtaaa    1440
aaaaaaaaag gagtgattag cccttaaata aatcttgata tcttgaagaa ttaatatttt    1500
acttttgact gaagaatgtg ttggataaat ttctatttat taatatgata tggcgtggtt    1560
gtaaagtaaa tttctactag aaatttgtgt aaaaactgaa gtcttttgt gtaagaatgt    1620 gtaaatagtt gattaatttta atccatatag taatgtgtat ggacaaagta tagtatctgg    1680
gaccctgaga ttataatgtt tggtaaaatt tgggaggtgg aacgaggtca ggggacgaca    1740
catttggtcg ggagaccgtg aaatttacgg tacgggacaa cacaattggg ccctcaagcc    1800
ccaattcagc ccaatgggct atcgaaaaga aagaaagaaa gtttgtgcgc tgcggatatt    1860
aataattttg tgacgctcca ccacatttcc ccattcccaa atttctcatt ctcccatttc    1920
ctctcagaac cctcgatcac tcccacgcgc tcctatatcc tctccttcac cgtcgctctc    1980
tccaacgatc acaacaacat cgtcatccca tggtcggttt ttttctctaa tttctctctt    2040
ccttttttcg ttatccgatt tgttctcacg catcaataac taaatccgcg aatttctagc    2100 gtttttttt ttgttgaatt tagtggcgtc gaaattctg agctggattc gtatttgatc    2160
tgatcgttta acttgaacgg tgcttttttt attttttgtt taaaataaag gaataaatcg    2220
tggcgatttc agatctgatt tcggtgcttc ggttgagttt ttcccaaatt catagcttat    2280
tatgatattt ttattgcgga tttcagttta caacagcttg tgatgtgtga tgtgtttgat    2340
ctgcgcagaa atcggttgtg atctgacatg tggattgatt ccatttatt tattttattc    2400 taattttaat tttatgagca tgttgattta acttctttta tgtgataatt atgcgtggaa    2460
atttcaatta aagcatatat tcttgtcttt ttttttgttt ttggttgcat atattcttat    2520
tctttcatta gatttatttt aatgatgttt ctatattaga tttattaatg aataaatatg    2580 atttatttt gggactgaag acacgacaaa cgtaacacgg ttttcttaat ttttattgat    2640
gtttacttgt tttggcacta atcactgtct gcttctatcc ccttgatttg gaagataccg    2700
tgtttgtgga agtattattt acttatttag ttggtcgcat attcctataa tatttcattg    2760
ttatcaatct acgaatttag tcttttttttt tggtaagca atttgattta ctttatggca    2820
tatttcaacc caattatgtt aacaagttaa caacccttg tttttttttct ttcccggagt    2880 aacaattta atgggaaaaa aaaagatta acaacatatt tgtgcacaat tacttggtat    2940
tgatgaccat ggtggtgtgt gtctgcaact gcaattctat aggcaaacgc cgcatctgg    2999
```

```
<210> SEQ ID NO 2
<211> LENGTH: 2345
<212> TYPE: DNA
<213> ORGANISM: Artificial Sequence
<220> FEATURE:
<223> OTHER INFORMATION: Synthetic polynucleotide

<400> SEQUENCE: 2
ttgacgagct gtctctggct gcttttcat tgtaccaatg cttgtctcct acacatcaac      60
tgtatttaag atctgaagct gacatgagat tttacaaagc attatataat tacattggcg     120
ccacaataat ttcgagatat ttatcaaaat aaataaagtt gcaaatgcaa atggagttca     180
catgcaatga atcccttgtc ataaactcca aaatcatgat tgcaacataa acaaatgttt     240
tagaaaaatt aaaatctgtg gcttacgccc tcatgcacat gttttgcgtg atgattaaca     300
gttgttacag ctccctcttt ctgagtcgtg gtaatttgag gtaaatttgc gtgatgaact     360
agtaagtttt attttccagt gaagcaactg ctacaggctt gggtgttgga gaaatttacc     420
attgagttat gcaatagtta cctggattat ccttactttt tataatagaa aaataatcct     480
tttaataaac tcgtttagat tctgtttata caaatttggt agattaaaca aattatcacg     540
tgacacaaat atttctatga ttgcttaaaa tagaataaaa agaatttagt tgaaattgtt     600
ttttatactg ttgatttga atagaataat atggtaaaat ggtcaattct tattggatat      660
ttatgtaaga atattttgca ttgaaattgt ctagaatatt tttagacata taatatgatg     720
ggtaaataat ggtgtccttc gaagtgtatg ataaaagatt catttcttag actcatgtat     780
agtaaaaaaa aaaaggagt gattagccct taaataaatc ttgatatctt gaagaattaa      840
tattttactt ttgactgaag aatgtgttgg ataaatttct atttattaat atgatatggc     900
gtggttgtaa agtaaatttc tactagaaat tgtgtaaaa actgaagtct ttttgtgtaa      960
gaatgtgtaa atagttgatt aatttaatcc atatagtaat gtgtatggac aaagtatagt    1020
atctgggacc ctgagattat aatgtttggt aaaatttggg aggtggaacg aggtcagggg    1080
acgacacatt tggtcgggag accgtgaaat ttacggtacg ggacaacaca attgggccct    1140
caagccccaa ttcagcccaa tgggctatcg aaaagaaaga aagaaagttt gtgcgctgcg    1200
gatattaata attttgtgac gctccaccac atttccccat tcccaaattt ctcattctcc    1260
catttcctct cagaaccctc gatcactccc acgcgctcct atatcctctc cttcaccgtc    1320
gctctctcca acgatcacaa caacatcgtc atcccatggt cggttttttt ctctaatttc    1380
tctcttcctt tttcgttat ccgatttgtt ctcacgcatc aataactaaa tccgcgaatt     1440
tctagcgttt tttttttgt tgaatttagt ggcgtcgaaa tttctgagct ggattcgtat    1500
ttgatctgat cgtttaactt gaacggtgct tttttattt tttgtttaaa ataaaggaat    1560
aaatcgtggc gatttcagat ctgatttcgg tgcttcggtt gagttttcc caaattcata    1620 gcttattatg atattttat tgcggatttc agtttacaac agcttgtgat gtgtgatgtg    1680
tttgatctgc gcagaaatcg gttgtgatct gacatgtgga ttgattccat tttatttatt    1740
ttattctaat tttaatttta tgagcatgtt gatttaactt cttttatgtg ataattatgc    1800
gtggaaattt caattaaagc atatattctt gtctttttt ttgttttggg ttgcatatat    1860
tcttattctt tcattagatt tattttaatg atgtttctat attagattta ttaatgaata    1920
aatatgattt tattttggga ctgaagacac gacaaacgta acacggtttt cttaatttt     1980 attgatgttt acttgttttg gcactaatca ctgtctgctt ctatcccctt gatttggaag    2040
ataccgtgtt tgtggaagta ttatttactt atttagttgg tcgcatattc ctataatatt    2100
```

-continued

| | |
|---|---|
| tcattgttat caatctacga atttagtctt ttttttttgg taagcaattt gatttactttt | 2160 |
| atggcatatt tcaacccaat tatgttaaca agtaacaac cctttgtttt ttttctttcc | 2220 |
| cggagtaaca atttaaatgg gaaaaaaaaa agattaacaa catatttgtg cacaattact | 2280 |
| tggtattgat gaccatggtg gtgtgtgtct gcaactgcaa ttctataggc aaacgccgca | 2340 |
| tctgg | 2345 |

<210> SEQ ID NO 3
<211> LENGTH: 2009
<212> TYPE: DNA
<213> ORGANISM: Artificial Sequence
<220> FEATURE:
<223> OTHER INFORMATION: Synthetic polynucleotide

<400> SEQUENCE: 3

| | |
|---|---|
| gtgaatataa agggcaccgc tcgttgttga tgagaacacg aaatctcctc tccacaatgc | 60 |
| aacgtcaaga tgtcatagac aggtatggaa aggaaaaata aataaataaa taaatggatt | 120 |
| ttatgctcca cccagtttgc ccttcctgaa tgctaacaaa actcaacatg tttttgaata | 180 |
| gggtaataat cggggttggt ttttgttgt tctcccttgc tgttctttat gttgtttcca | 240 |
| agcgaattgg actacttacg ttgcaaagaa aggttactga ggccataaaa gctggtatgg | 300 |
| tgggacaggc agagctaagg ccccaagctg ttgcagatga cgtgaatctt catcaagtca | 360 |
| gaggcaatcg tgttcctaat aatgcagagg ctcctttaga acaaagaatc catgatgaac | 420 |
| tatgatgcat ttctaagcaa tactatcatg ttatgtgtgt ttataacaca actcttctaa | 480 |
| ttcctttaaa agtaacgaaa gtaaaaagta ttttgctatc ttgagagttc gaaaagcatt | 540 |
| taatactacc ttttgagaa ttattggctg atctgttata atgaattaaa aattctttct | 600 |
| gtagttgttt ttgtctacgc tacaggcctt tcaacatgag caagctaata attgttgacg | 660 |
| agctgtctct ggctgctttt tcattgtacc aatgcttgtc tcctacacat caactgtatt | 720 |
| taagatctga agctgacatg agatttaca aagcattata taattacatt ggcgccacaa | 780 |
| taatttcgag atatttatca aaataaataa agttgcaaat gcaatggag ttcacatgca | 840 |
| atgaatccct tgtcataaac tccaaaatca tgattgcaac ataaacaaat gttttagaaa | 900 |
| aattaaaatc tgtggcttac gccctcatgc acatgttttg cgtgatgatt aacagttgtt | 960 |
| acagctccct ctttctgagt cgtggtaatt tgaggtaaat ttgcgtgatg aactagtaag | 1020 |
| ttttatttc cagtgaagca actgctacag gcttgggtgt tggagaaatt taccattgag | 1080 |
| ttatgcaata gttacctgga ttatccttac tttttataat agaaaaataa tccttttaat | 1140 |
| aaactcgttt agattctgtt tatacaaatt tggtagatta acaaattat cacgtgacac | 1200 |
| aaatatttct atgattgctt aaaatagaat aaaaagaatt tagttgaaat tgtttttttat | 1260 |
| actgttgatt ttgaatagaa taatatggta aaatggtcaa ttcttattgg atatttatgt | 1320 |
| aagaatattt tgcattgaaa ttgtctagaa tattttaga catataatat gatgggtaaa | 1380 |
| taatggtgtc cttcgaagtg tatgataaaa gattcatttc ttagactcat gtatagtaaa | 1440 |
| aaaaaaaaag gagtgattag ccctaaata atcttgata tcttgaagaa ttaatatttt | 1500 |
| acttttgact gaagaatgtg ttggataaat ttctatttat taatatgata tggcgtggtt | 1560 |
| gtaaagtaaa tttctactag aaatttgtgt aaaaactgaa gtcttttgt gtaagaatgt | 1620 |
| gtaaatagtt gattaattta atccatatag taatgtgtat ggacaaagta tagtatctgg | 1680 |
| gacccctgaga ttaatgtt tggtaaaatt tgggaggtgg aacgaggtca ggggacgaca | 1740 |
| catttggtcg ggagaccgtg aaatttacgg tacgggacaa cacaattggg ccctcaagcc | 1800 |

```
ccaattcagc ccaatgggct atcgaaaaga agaaagaaa gtttgtgcgc tgcggatatt    1860
aataattttg tgacgctcca ccacatttcc ccattcccaa atttctcatt ctcccatttc    1920
ctctcagaac cctcgatcac tcccacgcgc tcctatatcc tctccttcac cgtcgctctc    1980
tccaacgatc acaacaacat cgtcatccc                                      2009
```

<210> SEQ ID NO 4
<211> LENGTH: 1353
<212> TYPE: DNA
<213> ORGANISM: Artificial Sequence
<220> FEATURE:
<223> OTHER INFORMATION: Synthetic polynucleotide

<400> SEQUENCE: 4

```
gacgagctgt ctctggctgc tttttcattg taccaatgct tgtctcctac acatcaactg      60
tatttaagat ctgaagctga catgagattt acaaagcat tatataatta cattggcgcc     120
acaataattt cgagatattt atcaaaataa ataaagttgc aaatgcaaat ggagttcaca     180
tgcaatgaat cccttgtcat aaactccaaa atcatgattg caacataaac aaatgtttta     240
gaaaaattaa aatctgtggc ttacgccctc atgcacatgt tttgcgtgat gattaacagt     300
tgttacagct ccctcttcct gagtcgtggt aatttgaggt aaatttgcgt gatgaactag     360
taagttttat tttccagtga agcaactgct acaggcttgg gtgttggaga aatttaccat     420
tgagttatgc aatagttacc tggattatcc ttacttttta taatagaaaa ataatccttt     480
taataaactc gtttagattc tgtttataca aatttggtag attaaacaaa ttatcacgtg     540
acacaaatat ttctatgatt gcttaaaata gaataaaaag aatttagttg aaattgtttt     600
ttatactgtt gattttgaat agaataatat ggtaaaatgg tcaattctta ttggatattt     660
atgtaagaat attttgcatt gaaattgtct agaatatttt tagacatata atatgatggg     720
taaataatgg tgtccttcga agtgtatgat aaaagattca tttcttagac tcatgtatag     780
taaaaaaaaa aaaggagtga ttagccctta aataaatctt gatatcttga agaattaata     840
ttttactttt gactgaagaa tgtgttggat aaatttctat ttattaatat gatatggcgt     900
ggttgtaaag taaatttcta ctagaaattt gtgtaaaaac tgaagtcttt ttgtgtaaga     960
atgtgtaaat agttgattaa tttaatccat atagtaatgt gtatggacaa agtatagtat    1020
ctgggaccct gagattataa tgtttggtaa aatttgggag gtggaacgag gtcagggac    1080 gacacatttg gtcgggagac cgtgaaattt acggtacggg acaacacaat tgggccctca    1140
agccccaatt cagcccaatg ggctatcgaa agaaagaaa gaaagtttgt gcgctgcgga    1200
tattaataat tttgtgacgc tccaccacat ttccccattc ccaaatttct cattctccca    1260
tttcctctca gaaccctcga tcactcccac gcgctcctat atcctctcct tcaccgtcgc    1320
tctctccaac gatcacaaca acatcgtcat ccc                                1353
```

<210> SEQ ID NO 5
<211> LENGTH: 2988
<212> TYPE: DNA
<213> ORGANISM: Artificial Sequence
<220> FEATURE:
<223> OTHER INFORMATION: Synthetic polynucleotide

<400> SEQUENCE: 5

```
aagggcaccg ctcgttgttg atgagaacac gaaatctcct ctccacaatg caacgtcaag      60
atgtcataga caggtatgga aaggaaaaat aaataaataa ataaatggat tttatgctcc     120
```

```
acccagtttg cccttcctga atgctaacaa aactcaacat gttttttgaat agggtaataa      180 tcggggttgg ttttttgttg ttctcccttg ctgttcttta tgttgtttcc aagcgaattg      240
gactacttac gttgcaaaga aaggttactg aggccataaa agctggtatg gtgggacagg      300
cagagctaag gccccaagct gttgcagatg acgtgaatct tcatcaagtc agaggcaatc      360
gtgttcctaa taatgcagag gctcctttag aacaaagaat ccatgatgaa ctatgatgca      420
tttctaagca atactatcat gttatgtgtg tttataacac aactcttcta attccttttaa     480 aagtaacgaa agtaaaaagt attttgctat cttgagagtt cgaaaagcat ttaatactac      540 cttttttgaga attattggct gatctgttat aatgaattaa aaattctttc tgtagttgtt     600
tttgtctacg ctacaggcct tcaacatga gcaagctaat aattgttgac gagctgtctc       660
tggctgcttt ttcattgtac caatgcttgt ctcctacaca tcaactgtat ttaagatctg      720
aagctgacat gagattttac aaagcattat ataattacat tggcgccaca ataatttcga      780
gatatttatc aaaataaata aagttgcaaa tgcaaatgga gttcacatgc aatgaatccc      840
ttgtcataaa ctccaaaatc atgattgcaa cataaacaaa tgttttagaa aaattaaaat     900
ctgtggctta cgccctcatg cacatgtttt gcgtgatgat taacagttgt tacagctccc     960
tctttctgag tcgtggtaat ttgaggtaaa tttgcgtgat gaactagtaa gttttatttt    1020
ccagtgaagc aactgctaca ggcttgggtg ttggagaaat ttaccattga gttatgcaat    1080
agttacctgg attatcctta cttttttataa tagaaaaata atccttttaa taaactcgtt    1140
tagattctgt ttatacaaat ttggtagatt aaacaaatta tcacgtgaca caaatatttc    1200
tatgattgct taaaatagaa taaaaagaat ttagttgaaa ttgtttttta tactgttgat    1260
tttgaataga ataatatggt aaaatggtca attcttattg gatatttatg taagaatatt    1320
ttgcattgaa attgtctaga atattttttag acatataata tgatgggtaa ataatggtgt    1380
ccttcgaagt gtatgataaa agattcattt cttagactca tgtatagtaa aaaaaaaaaa    1440
ggagtgatta gcccttaaat aaatcttgat atcttgaaga attaatatttt tacttttgac   1500 tgaagaatgt gttggataaa tttctattta ttaatatgat atggcgtggt tgtaaagtaa    1560
atttctacta gaaatttgtg taaaaactga agtcttttttg tgtaagaatg tgtaaatagt   1620 tgattaatttt aatccatata gtaatgtgta tggacaaagt atagtatctg ggaccctgag   1680
attataatgt ttggtaaaat ttgggaggtg gaacgaggtc aggggacgac acatttggtc    1740
gggagaccgt gaaatttacg gtacgggaca acacaattgg gccctcaagc cccaattcag    1800
cccaatgggc tatcgaaaag aaagaaagaa agtttgtgcg ctgcggatat taataatttt    1860
gtgacgctcc accacatttc cccattccca aatttctcat tctcccatttt cctctcagaa   1920 ccctcgatca ctcccacgcg ctcctatatc ctctccttca ccgtcgctct ctccaacgat    1980
cacaacaaca tcgtcatccc ctggtcggtt ttttttctcta atttctctct ttccttttttc  2040 gttatccgat ttgttctcac gcatcaataa ctaaatccgc gaatttctag cgttttttttt   2100 tttgttgaat ttagtggcgt cgaaatttct gagctggatt cgtatttgat ctgatcgttt    2160
aacttgaacg gtgcttttttt tattttttgt ttaaaataaa ggaataaatc gtggcgattt   2220
cagatctgat ttcggtgctt cggttgagtt ttttcccaaat tcatagctta ttatgatatt   2280
tttattgcgg atttcagttt acaacagctt gtgatgtgtg atgtgtttga tctgcgcaga    2340
aatcggttgt gatctgacat gtggattgat tccatttttat ttatttttattt ctaattttaa 2400 ttttatgagc atgttgattt aacttctttt atgtgataat tatgcgtgga aatttcaatt    2460
aaagcatata ttcttgtctt ttttttttgtt tttggttgca tatattctta ttctttcatt   2520
```

```
agatttattt taatgatgtt tctatattag atttattaat gaataaatat gattttattt    2580
tgggactgaa gacacgacaa acgtaacacg gttttcttaa ttttttattga tgtttacttg    2640 ttttggcact aatcactgtc tgcttctatc cccttgattt ggaagatacc gtgtttgtgg    2700
aagtattatt tacttattta gttggtcgca tattcctata atatttcatt gttatcaatc    2760
tacgaattta gtcttttttt tttggtaagc aatttgattt acttatggc atatttcaac    2820 ccaattatgt taacaagtta acaacccttt gttttttttc tttcccggag taacaattta    2880
aatgggaaaa aaaaaagatt aacaacatat ttgtgcacaa ttacttggta ttgatgacca    2940
tggtggtgtg tgtctgcaac tgcaattcta taggcaaacg ccgcatct              2988
```

<210> SEQ ID NO 6
<211> LENGTH: 2474
<212> TYPE: DNA
<213> ORGANISM: Artificial Sequence
<220> FEATURE:
<223> OTHER INFORMATION: Synthetic polynucleotide

<400> SEQUENCE: 6

```
gcttttcttc tactttttcg gttttctatc gtgtccaaat aaaatttcta aaaaaacaat      60
taatgagaca tagaaaacca aacttgtatg gggaagtgaa ctagctgtta aaacaatgag    120
tggactcgtg atccctcact caaacagaaa gcataatgcg aattgctaaa aggggtccag    180
aactgccttg gctatttttt acgtgtgttt cttaattagg agccacgaga caaagatata    240
aaggttagtg taggaccctg ccacccaaaa tctgcctgga tattatgcat gcgtccctaa    300
ccttgttgct tgtggctttt gccagagtag aatgacgaag aaaattttca aaagattcct    360 aatgttttttg gctcacaact caaaaactca aactgatcaa gaaccgttca ttttattaac    420
gttatcctta caagtcactc aggctaatcg agctggtact aaactaatgc atattaggta    480
atgcaaataa ataataacgc tcccaagaat attcaaatgg tttctttgc ttttgctta     540 acgactttg tatctctacg tattacttga gaaaaaagc tgctattatt atccaactaa    600
acaaatgaaa gctacagtta aggacatggc ctattaacaa tattacgtag acttgatcat    660
tgtctcatcc acgagataga aacaaatat ataaagggc tcattatgct tatttagttc      720
atcaagaagc taggaaaatg agtacgtaga atgaacattt aataatggac gtgagagaag    780
ttaatcgctg acagccatgt gccgaccatg ttttttataa atgaaaagaa agaaatgttc    840
gtatataata attaacggac acaagaacct tgttaataat tatcattatc ttttttttt     900 tgttttatt ttccgaaaaa cttgtttctc caatcattga tgtgtatttc tattctctct    960
ccatttccaa ctcctgactg agaagtggat ttcatatcaa cattagcaat tagtagaata   1020
ctatcatctt tcacgctaca aaacattggt actttggtag gtaaagattt gcaaacacga   1080
ataagtaatt aagaaaggtt catacacatt caatgattct ggattcctac cttacgttat   1140
ttgtttcgaa atacctagat gagagcatct tgttatttat tactacatat taattttccc   1200
tgtgtacctt gtcgtagttt aaatttatta tttttttcaat cataaataaa tataagaaat   1260 attttttttct taatataatt ttatttata tttaaaaata aatcataatt tgaaagagct   1320
acaaatttat accacatgtg ggaagtattg ttggtttctc caaccatact tattgagaat   1380
aacttgaatt tatattcaac gtattaattg cttcacctttt aacgtgccaa ataataata   1440 ataaaaaact taaactact gtattaatcg cgtgtggttg aatggaggca aattctattc   1500
taaaaaagaa aagcattaac aaaaggagaa agaaaaaact gttgacacct gacagcagta   1560
```

```
acagggaact gggaagtagc agtaggagta tttgcgtgtt ggtttccaac tctggaatcc    1620
accgtgccaa actgcgaatg caggagaaat cgacacgtgt ccatttgcag gcgcgagttg    1680
aacgtgacaa tgcaccaccg cccagcatcg aacgcagcca aggaccacgt cgaaaccaca    1740
gtaatccacg ttccagtgct gcgcggaaca tggtcggtct ttctaggagt ggttggaatc    1800
acgccagcta ggacaaaccc catcaatcat tggtcattat caaacaaaac atttcaaaaa    1860
ttcaacatat tacgcctcgg gacccacctc ccactacacc tcaccctcac ttctattaac    1920
tcgaacacat tcgggttata aatccgcaac cctccttctc actcactcac tcactcactc    1980
actcactcgc aagcaaaaag aaagaatccc aggcgaggag aaagatggag gggaaggagc    2040
aggatgtgtc gttgggagcg aacaagttcc ccgagagaca gccaattggg acggcggcgc    2100
agagccaaga cgacggcaag gactaccagg agccggcgcc ggcgccgctg gttgacccga    2160
cggagtttac gtcatggtcg ttttacagag cagggatagc agagtttgtg gccactttc     2220 tgtttctcta catcactgtc ttaaccgtta tgggagtcgc cggggctaag tctaagtgta    2280
gtaccgttgg gattcaagga atcgcttggg ccttcggtgg catgatcttc gccctcgttt    2340
actgcaccgc tggcatctca ggtccgcttt tttttttctt cttttcttaa tttctcaaaa    2400
gctagaaaaa aaaattaat gtaaagttga caacgttgt ttgtttgtat gtgtaggggg      2460
acacataaac ccgg                                                      2474
```

<210> SEQ ID NO 7
<211> LENGTH: 2999
<212> TYPE: DNA
<213> ORGANISM: Artificial Sequence
<220> FEATURE:
<223> OTHER INFORMATION: Synthetic polynucleotide

<400> SEQUENCE: 7

```
gtgaatataa agggcaccgc tcgttgttga tgagaacacg aaatctcctc tccacaatgc      60
aacgtcaaga tgtcatagac aggtatggaa aggaaaaata aataaataaa taatggatt     120 ttatgctcca cccagttttgc ccttcctgaa tgctaacaaa actcaacatg ttttttgaata    180 gggtaataat cggggttggt ttttttgttgt tctcccttgc tgttctttat gttgtttcca    240
agcgaattgg actacttacg ttgcaaagaa aggttactga ggccataaaa gctggtatgg    300
tgggacaggc agagctaagg ccccaagctg ttgcagatga cgtgaatctt catcaagtca    360
gaggcaatcg tgttcctaat aatgcagagg ctcctttaga acaaagaatc catgatgaac    420
tatgatgcat ttctaagcaa tactatcatg ttatgtgtgt ttataacaca actcttctaa    480 ttccttttaaa agtaacgaaa gtaaaaagta ttttgctatc ttgagagttc gaaaagcatt    540
taatactacc tttttgagaa ttattggctg atctgttata atgaattaaa aattctttct    600
gtagttgttt ttgtctacgc tacaggcctt tcaacatgag caagctaata attgttgacg    660
agctgtctct ggctgctttt tcattgtacc aatgcttgtc tcctacacat caactgtatt    720
taagatctga agctgacatg agatttttaca aagcattata taattacatt ggcgccacaa    780
taatttcgag atatttatca aaataaataa agttgcaaat gcaatggag ttcacatgca      840 atgaatccct tgtcataaac tccaaaatca tgattgcaac ataaacaaat gttttagaaa    900
aattaaaatc tgtggcttac gccctcatgc acatgttttg cgtgatgatt aacagttgtt    960 acagctcct ctttctgagt cgtggtaatt tgaggtaaat ttgcgtgatg aactagtaag    1020 tttttattttc cagtgaagca actgctacag gcttgggtgt tggagaaatt taccattgag    1080
ttatgcaata gttacctgga ttatccttac ttttttataat agaaaaataa tcctttttaat    1140
```

-continued

```
aaactcgttt agattctgtt tatacaaatt tggtagatta acaaattat cacgtgacac    1200 aaatatttct atgattgctt aaaatagaat aaaagaatt tagttgaaat tgttttttat    1260
actgttgatt ttgaatagaa taatatggta aaatggtcaa ttcttattgg atatttatgt    1320
aagaatattt tgcattgaaa ttgtctagaa tatttttaga catataatat gatgggtaaa    1380
taatggtgtc cttcgaagtg tatgataaaa gattcatttc ttagactcat gtatagtaaa    1440 aaaaaaaag gagtgattag cccttaaata aatcttgata tcttgaagaa ttaatatttt    1500
acttttgact gaagaatgtg ttggataaat ttctatttat taatatgata tggcgtggtt    1560
gtaaagtaaa tttctactag aaatttgtgt aaaaactgaa gtcttttttgt gtaagaatgt    1620 gtaaatagtt gattaattta atccatatag taatgtgtat ggacaaagta tagtatctgg    1680
gaccctgaga ttataatgtt tggtaaaatt tgggaggtgg aacgaggtca ggggacgaca    1740
catttggtcg ggagaccgtg aaatttacgg tacgggacaa cacaattggg ccctcaagcc    1800
ccaattcagc ccaatgggct atcgaaaaga aagaaagaaa gttgtgcgc tgcggatatt    1860 aataattttg tgacgctcca ccacatttcc ccattcccaa atttctcatt ctcccatttc    1920
ctctcagaac cctcgatcac tcccacgcgc tcctatatcc tctccttcac cgtcgctctc    1980
tccaacgatc acaacaacat cgtcatccca tggtcggttt ttttctctaa tttctctctt    2040 cctttttcg ttatccgatt tgttctcacg catcaataac taaatccgcg aatttctagc    2100
gttttttttt ttgttgaatt tagtggcgtc gaaatttctg agctggattc gtatttgatc    2160
tgatcgttta acttgaacgg tgcttttttt atttttgtt taaaataaag gaataaatcg    2220
tggcgatttc agatctgatt tcggtgcttc ggttgagttt ttcccaaatt catagcttat    2280
tatgatattt ttattgcgga tttcagttta caacagcttg tgatgtgtga tgtgtttgat    2340
ctgcgcagaa atcggttgtg atctgacatg tggattgatt ccattttatt tattttattc    2400
taattttaat tttatgagca tgttgattta acttcttta tgtgataatt atgcgtggaa    2460
atttcaatta aagcatatat tcttgtcttt ttttttgttt ttggttgcat atattcttat    2520
tctttcatta gatttatttt aatgatgttt ctatattaga tttattaatg aataaatatg    2580
attttatttt gggactgaag acacgacaaa cgtaacacgg ttttcttaat ttttattgat    2640
gtttacttgt tttggcacta atcactgtct gcttctatcc ccttgatttg gaagataccg    2700
tgtttgtgga agtattattt acttatttag ttggtcgcat attcctataa tatttcattg    2760
ttatcaatct acgaatttag tcttttttt ttggtaagca aatttgattta ctttatggca    2820 tatttcaacc caattatgtt aacaagttaa caaccctttg tttttttct ttcccggagt    2880 aacaatttaa atgggaaaaa aaaagatta acaacatatt tgtgcacaat tacttggtat    2940
tgatgaccat ggtggtgtgt gtctgcaact gcaattctat aggcaaacgc cgcatctgg    2999
```

<210> SEQ ID NO 8
<211> LENGTH: 1894
<212> TYPE: DNA
<213> ORGANISM: Artificial Sequence
<220> FEATURE:
<223> OTHER INFORMATION: Synthetic polynucleotide

<400> SEQUENCE: 8

```
ttggagtccg tgtagtccac ggtagagatc aggtagcagt attctgccgc atcattggaa      60
ttaaaatcaa taataattag ataatgtagt tgtttaatta aatcaatagt taaaatttaa     120
tgagatttca atcatctaag attttaacc attaatgaga ttggaattta agaaataatt     180
```

-continued

| | |
|---|---|
| gggatgaagt taaaattaaa aaattctatt tacaagacac aatttgaaat aggttttaag | 240 |
| aaaaggtgta caatccatta ttgttattaa ttatttttcat tgattttttt tttctcacca | 300 |
| tctagttata gtctatgtga taatggcata agtattattg aggaggcatc cgtgaaatga | 360 |
| aatacttttc acacctctac ttgtactcac acaccacaaa atatcacttt accttcttca | 420 |
| taatctttgc cttttccatt tattttcatg tagttttat ttatttgttt tttttttcttc | 480 |
| taggatcaaa gatatatcta aagaacgaaa aaataagata tatctggcta tttatttgat | 540 |
| ttgacaacga ataaactttt actctatcct ttattctttg ggtttacaag tattttttat | 600 |
| attctaagat ttttttacttt aatatttatt tttatttcaa tcaactactt tataaagtca | 660 |
| tttattttta tgataaaatt aaggtaaata acattttggc taaattagaa attaaagtag | 720 |
| aataaattaa aagattgaac aacttaaatt attattatta gtattattat tcaacttaaa | 780 |
| tgcccagatc cctctatctt atactttatc atttcaggaa ttgattgact tgacacaata | 840 |
| atgcatgtgc ctgaccagct acgtctaaga tgttaataag atagtacttt ttaatgtaat | 900 |
| atttttttatt attattgatt aagcttttttc tagatataaa ataatgcggg tttcagtttt | 960 |
| caattgataa attaatagtt aatattttta taaaaattaa aatatacaaa ataaagtga | 1020 |
| taaaaattaa taaattttct atcctttttg agttttttgct ataaaaatct aaggagaagt | 1080 |
| tccctggttc ggaactgacg tagaccaatt ttgtaagaat cgacaatgac gggtcttttc | 1140 |
| cgatccaaat ggtccctcca cagtcctag atcaatcctt gtccacattc acttggcccc | 1200 |
| atctccatgt tttctcacat caactaattc tcaagcaaaa aaataaaata ggttctttga | 1260 |
| aggaatgata cagtgaccaa tttaattttt aaatatgtaa aaattatgat aaattaattc | 1320 |
| tattaaattt gtgaatttat tttattatta agttataata tttaatgact aatttgataa | 1380 |
| tatattatat ttttaagatt aatttgatat taaaggataa aatttatgat caattttttt | 1440 |
| attaaattat atgttaaaat taatttattg tatttttttat atatttggag attaaatttt | 1500 |
| tttttctgtt cacactttgt cagcactttt gttgtttttt ttttcaaaaa gagaaaaaga | 1560 |
| gaatataaat ttaaatttaa agcagaagag aacgaagcgg cgtcgtttgt tgcggcctga | 1620 |
| aaaaagtcca cactcgtgaa agtcattggc ataatgacga gcatatccgt gagtgacctc | 1680 |
| ggatccgctc cactaacccct agtcaactcc aaactcaacc atagttactt tacttcactc | 1740 |
| acaccccgcc acgtgttcca atcgaacggt cacttctgca tcacgcgcca ctataaaatat | 1800 |
| ctctctctcg tcatccgcaa ccccaagcaa aaccctaatc cctctttctt cctcttcctc | 1860 |
| agtagtgcga ttttcgattc tcttctctgc aact | 1894 |

<210> SEQ ID NO 9
<211> LENGTH: 2166
<212> TYPE: DNA
<213> ORGANISM: Artificial Sequence
<220> FEATURE:
<223> OTHER INFORMATION: Synthetic polynucleotide

<400> SEQUENCE: 9

| | |
|---|---|
| ttggttctcc agtaagtttt ttaattgggc tcaagaactt taggatttag atgaggatca | 60 |
| ataaaaattg atatattgcg cttgcttgtt tttttttttt cattaaattt acgcaaaaat | 120 |
| gaaagaaaaa ggtattcacg ctcttaaaat aaattaataa gcagaaattc caaaattttc | 180 |
| agttagtcct tactaattat taaattatag tattaatcca atgtgattgc ggttacatca | 240 |
| tgtacgaaa aataattcta atccttgatt taaatttgat cttgactatt tatttattct | 300 |
| ttatttcatt ttgtaaatca ttttatgtat ctcctggcaa gcaatttttat ccaccttgca | 360 |

```
ccaacacctt cgggttccat aatcaaacca ccttaacttc acaccatgct gtaactcaca      420
ccgcccagca tctccaatgt gaagaagct aaaatttaat aaacaatcat acgaagcagt       480
gacaaaatac cagatggtat taatgctttg ataaaattaa ttggaaagta taaaatggta      540
gaaaataata aattataatt aatttaaata agataaaaaa taattaaaaa ctaaaatgtt      600
aaaattttaa aaaattatt ttaaataata tttaaaaaca ttaaaaatca ttttaaaaaa       660
tttatttata gaacaattaa ataaatattt cagctaataa aaaacaaaag cttacctagc     720
cttagaagac aacttgtcca acaattagat gatacccatt gcccttacgt tttctttaac     780
atcaattatt gttttttgtca acaagctatc ttttagtttt attttattgg taaaaaatat    840
gtcgccttca agttgcatca tttaacacat ctcgtcatta gaaaaataaa actcttccct     900
aaacgattag tagaaaaaat cattcgataa taaataagaa agaaaaatta gaaaaaaata     960
acttcatttt aaaaaaatca ttaaggctat attttttaaa tgactaattt tatatagact   1020
gtaactaaaa gtatacaatt tattatgcta tgtatcttaa agaattactt ataaaaatct   1080
acggaagaat atcttacaaa gtgaaaaaca aatgagaaag aatttagtgg gatgattatg   1140
attttatttg aaaattgaaa aaataattat taaagacttt agtggagtaa gaaagctttc   1200
ctattagtct tttcttatcc ataaaaaaaa aaaaaaaaat ctagcgtgac agcttttcca   1260
tagattttaa taatgtaaaa tactggtagc agccgaccgt tcaggtaatg gacactgtgg   1320
tcctaacttg caacgggtgc gggcccaatt taataacgcc gtggtaacgg ataaagccaa   1380
gcgtgaagcg gtgaaggtac atctctgact ccgtcaagat tacgaaaccg tcaactacga   1440
aggactcccc gaaatatcat ctgtgtcata aacaccaagt cacaccatac atgggcacgc   1500
gtcacaatat gattggagaa cggttccacc gcatatgcta taaaatgccc ccacacccct   1560
cgaccctaat cgcacttcaa ttgcaatcaa attagttcat tctctttgcg cagttcccta   1620
cctctccttt caaggttcgt agatttcttc tgttttttttt tcttcttctt tattgtttgt  1680
tctacatcag catgatgttg atttgattgt gttttctatc gtttcatcga ttataaattt   1740
tcataatcag aagattcagc ttttattaat gcaagaacgt ccttaattga tgattttata   1800
accgtaaatt aggtctaatt agagtttttt tcataaagat tttcagatcc gtttacaaca   1860
agccttaatt gttgattctg tagtcgtaga ttaaggtttt tttcatgaac tacttcagat   1920
ccgttaaaca acagccttat ttgttgatac ttcagtcgtt tttcaagaaa ttgttcagat   1980
ccgttgataa aagccttatt cgttgattct gtatggtatt tcaagagata ttgctcaggt   2040
cctttagcaa ctaccttatt tgttgattct gtggccatag attaggatt ttttttcacga   2100 aattgcttct tgaaattacg tgatggattt tgattctgat ttatcttgtg attgttgact   2160
ctacag                                                                2166
```

<210> SEQ ID NO 10
<211> LENGTH: 2024
<212> TYPE: DNA
<213> ORGANISM: Artificial Sequence
<220> FEATURE:
<223> OTHER INFORMATION: Synthetic polynucleotide

<400> SEQUENCE: 10

```
taagccatag ttgcatatca tatctctatc tcaaatattg aacatgtaat ttatttattt     60
tttcttttaa aatatattct ttaatttaaa ttttgaactt gatttgattt aacaattaat    120
ccaaaaattg attttcagtt acgtcaaatt atttcaatta cctcaaatca cttttctttt    180
```

| | |
|---|---|
| gtctttattt gtctaattat ttttttaact actaatcttg tcttaaaatt aattttaata | 240 |
| tttttaaaa aatgatcagt agttaaaatt aattttatat cacaatacaa attatttatc | 300 |
| taacaaaaca gataactaat attcaaatac aattatctct acgattaaaa agtataaaaa | 360 |
| gggaagcaaa atatttatct aaaaaaatat tattatcttt ttaatgaaaa aaataaaagg | 420 |
| ataacaaaat attttgttaa aaagtaaaaa aaaagtaaac actaaaatat tattatctct | 480 |
| aaagtcttat tccaccaaat aaaaaaatca ccataacgtt aaaatattat ttatgctaaa | 540 |
| aattctaaaa agccagtggg ccaatgcctc cacccttaa aatagtttca cttccactcc | 600 |
| cgaaaagggt tcaatttaaa aaaaaattaa aagaagtct aaaaacttga ttaaataata | 660 |
| tcaaatagtt ttttaagga aaataatatc aaatagttta gaaacctacg aggaatttaa | 720 |
| tcttattttt atttatttta tctttactaa ttacacatat attcatcttt caatatatga | 780 |
| ctatatttaa aagaaaaaca ataacctact attgcttata atggctaaaa atacaatcta | 840 |
| tatataagct cacacatttc taatttcaaa tgcagagaga tattgagtac agttattcca | 900 |
| caaggtggga taattttatt attcttcttt tataaagtat aaaatattga ccaacaaaat | 960 |
| ctctcgacca agtcagtcaa ccatatatat ttgatattta ttttgtaaca aaaaacattt | 1020 |
| atatttattt aggacgtaca gataacgcaa tgcgacgcga ctttgtgcgt aaggaccacg | 1080 |
| caacgtttaa ttgttggcag ccagcgcgtc attgccgccc ttgtaccaag ccgccaatac | 1140 |
| gctactctta ttttaccaaa ataccctct attattgtaa agaaacagat aacaaatagt | 1200 |
| tttttcccac ccataaacga gccgcaccta atgttacacg tcaccaaatc ctcaccgtca | 1260 |
| acacaagcaa tctcaaccgt ccatgttccc aaaaacccaa tataaaataa agcatagggt | 1320 |
| tcccttctat ctctcattca gcgcctcctc gtcttcaatc ctttcgttat tctcttattc | 1380 |
| atccttctct tctgaataat ccagatctct ttctgccctt ttctccgtca cgcttttcgt | 1440 |
| gaccggatct gtatggattt gatccagatc tacacgccga tggtggtttt ggccgggtac | 1500 |
| gacaaacctt cgatcgtatt ttgctttata taggttcgat ccatcgttat tagcgttttg | 1560 |
| attttgttat ttaaattaat cttgtaggtc tttcatagat ctggtgcgta gaggctcaga | 1620 |
| tctacggtac cgaggtgtgt gattcatgtt cgtcttgctt ttggaatctg tttcgtagaa | 1680 |
| agtcgtttgg tcttgcatat ggcatggctc ttgaggtatt tttttgcagg tacaacagag | 1740 |
| aatcgatgac aagaacgcag atccgacggt agatccagcc gattccgctt gttcgatcgc | 1800 |
| tacagacccc tgtatcggat cattaagcag cgtgtctcgc gcgttctaca cgtgttgccg | 1860 |
| atctcggatg ttgtaaaatt agtttatgat gtgaagctat ggagtggaaa atatgtggat | 1920 |
| gtaggagatt tcgggatgaa tggcctcaaa acgctttgtc gtttgtggtt attgagtcct | 1980 |
| gagtgatctt gtcatccgac ctttgccatg acaggtgcgc ttgc | 2024 |

<210> SEQ ID NO 11
<211> LENGTH: 2257
<212> TYPE: DNA
<213> ORGANISM: Artificial Sequence
<220> FEATURE:
<223> OTHER INFORMATION: Synthetic polynucleotide

<400> SEQUENCE: 11

| | |
|---|---|
| gaacattaaa tcaagttaga atgaccccat aatccaaatt tatctttaaa aaagttatca | 60 |
| aatatatcta agaaatgtta gaaatatatt ttctaacata tttctttaac acactcaaat | 120 |
| ttaactaaaa tttattaaaa attataaaat taagagaaaa acattaaata taatataaac | 180 |
| tccacaaaat tgaattattt ttaataaatt ttaatcaata aaaataagtt taataattat | 240 |

```
atactgacaa aagataaaat aattttgttg tatcatttaa ttataattta tcttagtaaa      300
ctaattatta taaaagttaa taaaattatt attatatatg tataggggggt gggatgtaag     360 atgatatatc ctcaaaatgt gttagagaac gtgctaaata tttatttttt ttttaagttt     420
cccagcattt ctcgatccat atttaaaacc taaagtcatc cagataaact caagtcggat     480
cacgccgggc atgttatgct taccccctaat tataacaaat ttaagtcaaa tttgaattta     540
ctctgaattg ttatcaatgt taaaatctta cactactaat acataaaaat tagtattttg     600
ttatttactg aatgtatttt acacaatggt caaaacgttg ttttttttgt tttgaatgcg     660
gtcaaaacgg tttttaaagc atcaaaatac atgccattgt caggtacgaa ggttttttttt    720 tttttttttcc tttctatcga gggagggata ataagaatat aaaatctcgt taaataacga    780
ataaaataaa tgataagaat tatgttaatt gtcattttat acgcataatt attgagcaca    840
ccgttatctt ctagctgtaa catgctaaac tcgagaacaa agaaaaaaa aaatgaagta     900 tatttagctg ttgtctattc atttgttagc cgttgtaatt ttttcacgtg tcattgtaat    960 tttttttatga aaaaaacgc ccatgaaaga aggcacaagc cactgtggcc aattaatagc    1020
tgttaccatt ttaatacact gagttttcaa ctttgaatgg tcaaaagcta agggacaaga   1080
aaaccaggtt acacttgcta gatttttcta tttttattta tttattttcc gaaaatacag   1140
aattattgaa gaaataaat aaatagttag aatgggttgg ttttcttctt tgactgtcac    1200
cagcgcatta tagcacacca cacaaaaaag caaagcagaa aacaactgtt acttacacac    1260
gccatgggta tgggtatggg tatgggtatg ggtatgtatg ccattatcat catcgatcta    1320
actctaactc tctctttctc ttccttctaa ccgccgcttc cgcatctcgc ttccttctct   1380
tccttctcta actatatata ttttcttttt ctctctgttt cttccttttt attttatgct   1440
tttttctccg atgtgactgg cgtttgtttg gtgtgtttt cgtgtgcgtc gaaccctctg     1500
cgttcgttaa ttttgttttg tgttttcgga tcgacttgtt tcgcgttcgg ttgcgggggat    1560 cttcggttta ggtttgttta gggattttttt gttttttgtt ttttttttct gttgttcatg   1620 agttttttcgt tggatttgtt gtgttctgtg agattgatgg gctttttttt taaaatttat    1680
attccttcaa tgttttttct ttttttggcaa aatgaatatt tatttatggg cggaatgtat   1740
ttgcgatttt tgtctcttaa attcatgttc gaacggtggt gtgactttcc tgtttggttc    1800
tgtttttatg aagcctgttg actgcaattt tgcttctgaa aaattaaaaa ggaaatatgt    1860
tactgtcatt tttctacgca tatctaatat atcttctttt tgtttttttat ttatttattt    1920 taattatggt ggaattgttc attctggcag gtaaatgagt ggtaaatgag tggttttttga   1980 gcagaagcag ttaaaagaga aagggattca gcgaagatga catcggttgg tgtggcacca   2040
acttcgggtt tgagagaagc cagtgggcat ggagcagcag gtgttgatag attgccagag   2100
gagatgaacg atatgaaaat tagggatgat agagtatgta atttgtaacc ccgctctttg   2160
atattttcgt ttttttcatg ttagttttat tttctctatg tccatgttgt tggttactta   2220
cagtttgctt cattttgtag gaaatggaag ccacagt                             2257
```

<210> SEQ ID NO 12
<211> LENGTH: 2064
<212> TYPE: DNA
<213> ORGANISM: Artificial Sequence
<220> FEATURE:
<223> OTHER INFORMATION: Synthetic polynucleotide

<400> SEQUENCE: 12

```
ccgagacact tgtgtgattg agagaaacac taatcttgtg aggactgaag tttggtgatt    60
atttcttgtg atctgtcgac aaaaatatca aatggggttt cttttacaaa ttatttacct   120
aaatgaatct gttttgaaaa tatttactcc atgggtctat ttttttatta caaagcgtct   180
ccctgaaggg cgcgttcccc gtgaaagtga cacgtggcag gacttgggac gtgccctgcg   240
tacaggcgcg atagttagtg ttgttacagc aggcgcatcg ggtcgtgttg gggaccaagg   300
tacgacaggt cgcgctgggg acccagacac gacccaattg ggtcgcactt tatttaatat   360
tttttatatt ttgtatattg ttttttattta atatattttt atattatttt atttaatttt   420
tttatatttt atataatagt ttctatatta aataaattct tagcattatg tatgatttta   480
aagtcataaa taatttttta tattgttttt atttactata tttttatat tttatttaat    540
atttatatat taaataaatc cttcatatta gaaaaaataa agaaaatatt aaataaaata   600
taaaatataa aaagtaaaa aatattaaat aaaaatatat aaaaaatatt ataaaaacaa    660
tataaaaaat ataaaaatat ttaataaaat aataaaaaaa atattatttt aaataaaatt   720
atttatgact ttaaactcta aagttgaatt ttaaaaaaat ataattttttt tacgatttta   780
gtaaaaaaaa aatacaagcc gcacaataca agtcgccttc tcaaacccct cctcacgaca   840
ttctcggacc ttatgacacc gtcaccaaaa caatgatcca cgcgatatta ggcgcgtgca   900
aatcactcta atccgaaact agtagacatg ggaagcacga gctatacgcg agcgtttcaa   960
ttgccgccac gaaagcagag aaggccagaa acggaaccac ggtaaaatgg taagggtatt  1020
ttcgtaaaca gaagaaaaga gttgtagcta taaataaacc ctctaaccca cggcgcacta  1080
tttctcttca ctccttcgtt cactcttctt ctcttgcggc tagggtttta gcgcagcttc  1140
ttctaggttc gttctcttcc gccgctctat ggatttttaaa ccttcgaatc atgtttattc  1200
cattgaatta tgttgcttgc agtttatatt ttctgaatct gtagtgttg tcttcaattt   1260
atcctatgct ttatagatca atcttttgtg tgtgtagtac gtaattttttg ttcttttttgc  1320
ttttcgttca agttgtttggg aataatcggg gtatcatgtt ttgatattgt ttgttttctt  1380
ttttgactgc ttaataattt ttaagttggt ttttggtttg gggtttatg tgcttgttat   1440
attcaaatct ttggatccag atcttacaaa agttttgggt ttaaggatgt ttttggctga  1500
tgatgaatag atctataaac tgttcctttt aatcgattca agcttaggat tttactaggc  1560
ttttgcgaat aaaatacgtga cagtaagcta attatgtcct ttttttgtct caatcatatc  1620
tgtctgggtg tgccataatt tgtgatatgt ctatctggta gaatcttgtg ttttatgctt  1680
tacgatttgg tatacctgtt tttgaacttg ttgtatgatg ggtatttaga tcaccctatc  1740
ttttttatgc ttctggaagt tttatgtaaa tgtcgaatat cttaatgttg ttgaacttat  1800
aatgttgtgt tgatgtatgt atgatggttt tgacaacttt tttcactggt tctgaaagtt  1860
ttatgtaaat tgcaaatatg ttaatgttgt tgaacttatt ttttttcctt cgatgttgtt  1920
ttgatgtatg tatgatggtt ttcaccgtag tttctatggc taatatctta atgttgttga  1980
gcttattttt ttccttatat gttgtgttga tgtatgtatg atggttttga caactttttt  2040
agtttctttg cagatttaag gaag                                         2064
```

<210> SEQ ID NO 13
<211> LENGTH: 2687
<212> TYPE: DNA
<213> ORGANISM: Artificial Sequence
<220> FEATURE:
<223> OTHER INFORMATION: Synthetic polynucleotide

<400> SEQUENCE: 13

-continued

```
gggggagtgc atttcctgct gctagtattg cccaagagga aaaatgtctt tgggacagaa      60
acaagagact agctatctgt ggagacttct gtgtcagtcc caatgttgaa ggtgccatag     120
acagtgcctt cgcagcagca ttaaggctta agatagtgt cagctcttta tagttggagc     180
attacaatct gtagttctcc aaaccttgca tgcctttatt tcagtttttt ctcctgggaa     240
aacgtgttca aaattctttt taagacattt ctgtattact aaacgcgaac aaatttccct     300
tctacgacga agccttgcac actacaaagt atgagaaaga ggtacagggt ggttgcactt     360
tgccgtgcca agtttgcagg aaaatggtga tgaaaccacc tttgaaatca acagtgttg     420 agtttagtct taacaacaaa aataaggta aacatatgtt aagtgcacta gatgatggcc     480
taatgtactg taattctgaa tttgtgatca tgttatttcc ttttagttat aactaaaata     540
catttcagaa agcaccatgg cttgacccaa caaatatcaa aatatcatca tcccacatgt     600
aatggttatt ttcaaataca gatatgtgcg tgtgtgctag gtttatttat ttcattggaa     660
taatgttatt tgatttaatt ttatctaaaa acagcttaat ttttatatgc ttgagaagtt     720
ggaattttcc tacagggtcc tgaattatat cataagttgg agaagttggt tttgctctaa     780
tggaggggac agagagacta tgttagtatt tccaatgcca tcccattaca atcaggacaa     840
aacaaccaca ccaataaatc cttcataagc ctgatttgca aaaactttt gcactcccac     900 tattgtttcc tgcacttccc ataattgcat tacaaaatga acttgccgga aaacaatgag     960
aagcgcagaa agcaacagcc tgatagctat catagcttga tgatggattg aactttcaga    1020
atttaggatc ctctatgaca aggagttaag ggacaagccc ttttaggttt tgttgccgaa    1080
ctaacatgta atacaaacca agtcaatcaa aagacatgga tggattttaa aatgtcaaag    1140
gaagtagagc taggatcatc ttagagttta aaataagttt ttatttata ttttagtttt    1200 taaatttaat tatttattgt tatttagtt ttaaaagtac gataatatta gtcatatgag    1260
tttttaaatt ctagactaaa gtgagttaca tattaaattt tcaagatatt tttaaattct    1320
ggactaatat atatgtacta cacatcaatt tttttatact aacaaaatta tttattgtca    1380
tgctagtcac tgtgttttt tattgtattg tttatgtatt cagcctatga ttatgaatga    1440
aataatgaga tctttcctta aaaaaccaaa attatttact aatattgata gtataacctt    1500
ataaattaaa atttatatta ataatttaat ttctattaaa aaatgttatg ttaacgaaag    1560
ctaagggaat aactaaccat tataactttt tatttattt catttctctt aattaagaat    1620
ttatttcgtc cattctcttt ttaactgcaa ttctacagta gttttcaact taaaacattg    1680
atatgttgga aacctcactt ttttttccac cagaaaaaaa taaataaaaa tccgttgtat    1740
ttttcgtgga aggaatatcc acgtttcttt catcaagatg gatgttgaag attttgtttg    1800
cacatccata ttcataaaaa aacaggtgaa aaattgatct cattgagata atgtttacat    1860
tatcatatcc tggcactcta ccacaaatgc catgccacgt gccaccaaag caatcacaaa    1920
tacgtggcca ctattattat tatcacttgt ttttgtttcc catagcatag aagaagcaga    1980
aagagaagca ttagcaaaag caagaagaac tagtctaagc agaaatggcc tcttcagtga    2040
tggcatctgt ggccctcaaa cctgcccctt tcactgttga aagtcctca gttagaggcc    2100 ttccctccct ctcaaggaac tcctcttcat tcagagttgt ggccagtggt ggcaagaaga    2160
tcaagactga caagccttat ggttagtata tatacaggat atgtcttttc agaaacttta    2220
ctttagccag ttcatcatc gtcgctgtat tttaaaataa ttatagttat aacttattca    2280
agtacttttg aaacatttaa atatgtatac agcaaaatga attggatggt taaaaaaaat    2340
```

| | |
|---|---|
| ctaaagttaa atcctttcaa ttgacaaaaa ccaaaaaatc taataattaa cattttctta | 2400 |
| taagaaaaac acacacacat atgtatatgg gatttgtata catacttgtt tatcacaaac | 2460 |
| cgtactacgt tagcaagtta catgattgtc ggcatttttt aaaatatttt tatttataac | 2520 |
| ttggtataat atttttttata taaaaaaaaa gatgaagtac gttagcaaat atatatatat | 2580 |
| atatatatat atgttgagtt ggggggttgt ggtgggtatg gattactctt tcacttgtta | 2640 |
| attttgttg cttttatgtg attttttgca ggaattaatg gtggcat | 2687 |

<210> SEQ ID NO 14
<211> LENGTH: 2191
<212> TYPE: DNA
<213> ORGANISM: Artificial Sequence
<220> FEATURE:
<223> OTHER INFORMATION: Synthetic polynucleotide

<400> SEQUENCE: 14

| | |
|---|---|
| caaaaaggaa gcactgagtg cggctattat gtcatgcact ggatgtccac catcatatta | 60 |
| ggaaatttca ggaataactg ggaagcagta cgtttatttc aaacaaattc gattttttta | 120 |
| taatttgtat tacattatta acttatcatt tatttcatca tgcagtattt taacgatcct | 180 |
| agaccattgg agttagagag attaaagacg cttcggatcc agtgggcata gtattatctc | 240 |
| cgagttagag atcagagcta gctaggattt agggacattg agtttaactt agtttacttt | 300 |
| ggttttacat ttttgtcatt tcctatgtta tttgaacatt aaattcattt gttgataggt | 360 |
| gttaataata aatcaattat tcattgttta ttgtgattaa aactgcttga aagcagaata | 420 |
| aaatgtttat ttactgtgaa ttgggtcaaa aattgtattt tacaggtaca atttgggtt | 480 |
| tattataaag aaagttata taaaaaaaac ttgaaaacaa catcggttat taataaaaac | 540 |
| cgatgttaat atagtaaaca acatcaatta tttagaaaaa tcgatgtcaa catacacctt | 600 |
| aacatcggtt tttcaataaa tcgatgttgg ttatttctaa taacatcggt tatttataca | 660 |
| taaccgatgt taatatacaa acgttaacat cggttattta aaataactg atgttatata | 720 |
| taactaacta caacaaataa gtgtatagat gatggacgtt cacattggtt atatataaaa | 780 |
| aaacgatgtt aatctattgg ttaacatcga ttttatatca aaaccgatgt caacgttcat | 840 |
| catgtataca cttattttgc tatagttctt tatatataac attgcttatt tagaaaaccg | 900 |
| atattaacat ttttatgtta acatcagttt ttaaaaatcg atattaacaa taatacattc | 960 |
| agcatcagta ctttcaacat cggttttaaa atcgatgtag aatgctgtaa ataaccgatg | 1020 |
| ttgaaagtat atttttctaat agtgtagagg tattcgagta tttgaccaag ctgagtactt | 1080 |
| gaatacttac tgtgttgaaa gatgcattta agaaataagg caagataggg gagtatctaa | 1140 |
| gtattcggca tgtccaaata tccgaatatt agtggacact ttgaagagtt cttgaatgtc | 1200 |
| aaggttgtta gcgtgcaagt attcagcatg actaaatacc caaacattgg tgaaagcttt | 1260 |
| gaagagttct tgaatgacaa ggttgtcagt gtgcggatat tcgacatggc taaatatttg | 1320 |
| aacactgatg gaagttttga agagttcttg aatgtcaagg ttattaatgt gtaggtattc | 1380 |
| gacggcatgg tcgaatacgg ggatatgaaa tctaaggagc acttaagtgt tcactcaagc | 1440 |
| cgaatgtcta agtatctttt atagaatata cttcaatgtc ctaaagattt tgttagagat | 1500 |
| atttttaaatg tttgattaga ccaaacactt atctaatata ctttaaaatt acattaaaag | 1560 |
| ttatttgatt tgtaacaaaa acattttaca ttaataatca tactcattaa actcatctta | 1620 |
| acatcatttt caacaaattt atccgtacaa aagttaattt tgatcataaa taattatcaa | 1680 |
| ttataaataa caattgatga ttgaaataat ctaatttta tatattgcaa taaaattta | 1740 |

| | |
|---|---|
| cacgcttaat taattaaaat tataataaat atgattttca agtcattatt ataaaaatgt | 1800 |
| agatatcagt ttattaagta aatatttaat gaatctttat aatattatct aatttataaat | 1860 |
| tatctcagat taaaaaaaat taatcataaa aaataagagt aagctcactt tttttcaaaa | 1920 |
| aattaaataa aatagaatcg cattgacgcg aggcagaaat cgcaaaaaat ggtatcacgg | 1980 |
| gtcatacgcc ggtcccgtag gtgtcacccg acccacctac ttcacttacc tttacctgtc | 2040 |
| atttttcgct cttctttttt tacccttctt tcaacccttta ttaaaaccct atctcactca | 2100 |
| ctctcaccca cacaccgttt gttctattct taactcaact tctgctaccc actctcttct | 2160 |
| tccaagtcca accacgcttt tctctacagt c | 2191 |

<210> SEQ ID NO 15
<211> LENGTH: 3044
<212> TYPE: DNA
<213> ORGANISM: Artificial Sequence
<220> FEATURE:
<223> OTHER INFORMATION: Synthetic polynucleotide

<400> SEQUENCE: 15

| | |
|---|---|
| gtcgaacatc aacatcatct cgcagaataa aagatgtgta catataacgt tgtcctgact | 60 |
| caaatatagg acatcgaagg tggagatgtt aaatatgttg ttgtggttca atgtttagtt | 120 |
| tttggtgaat aagttcaagc aattctgtaa aggttatgac cttgttgatc atgaaagttt | 180 |
| ttgtgttgtt actaacgaaa gtgatgtcct cattagtgtt gcagatttgg ccattatagt | 240 |
| aaacacaaac atatgcagtt gggtgataca ttgtggtagg gattgagatg aaaatttgaa | 300 |
| agtgttacga atatctttag ctgtagtggt atttgtagaa tttacttata gttgagtgag | 360 |
| tcactagtta actgtgcatt tagatgagca ggtaaatgaa cacttaagca tatttgcaag | 420 |
| agtccatgat gtgcaaattg caaagtgttg ctggtaagac atttaatttt ttagcaacgc | 480 |
| ctgcaaattg caaagtgtta tcaatttgga ctgtgattta tccctgataa ttgatggagc | 540 |
| aaaagtccat tataatttc agagtggaga aaaattctga gttatccatc ttatgttagt | 600 |
| tttattggtg caacatttat tttttttagag acgtatgtaa attgcatagt gtcacggatt | 660 |
| ttttttttt attctttgac gttcaaacca tggaaaaagt gtgtcacgaa tatcattaat | 720 |
| gtgttggaca taattttaaa aaaatgcaaa acatgaacac ttaagcataa ttgcaaaggt | 780 |
| tcaaatcata attttttcga tgccttagga accttttgct aggcactgct agttttttttt | 840 |
| ttgttgttttt tccttgtgtt tatattctga tgcataaaaa aaaatctcca acttcatatt | 900 |
| ttttagaaaa ctaaaaaata ttcttgtaaa aatgtcccct aaaagaattt aataaatatt | 960 |
| tgttgtcggt gtaaatgttt gtacattttg tacttattac aattatcaag aaaaatgaat | 1020 |
| gttatacaga tgttggaata ataaataaaa taaataatat aattaggaat ataaataaaa | 1080 |
| atattaatta tatttcttaa tttctatata ataaccttaa ataacaaaat aaaaagatga | 1140 |
| aagtagccta aaatgaagaa aaaatgatta aaataattta ccctaacaat agaaacacac | 1200 |
| acccaaaaat aaaataaaaa aagagtatgg ggtccatgtt ttgtcggctc aagatagtaa | 1260 |
| aaatggatag tgatttaaaa tttgtattgg atagaatata ttagtgtatg tttgatttga | 1320 |
| ccattttcta taaaaacaga aacaatgtta agaatatgtt tagttaaaat tttaaaaata | 1380 |
| tttaaaaaaa cagtgaaaat tcgaaaacgc gaaatactca ttctcatgga aacagaatcg | 1440 |
| gcctttagaa aacgcaatgg cataaaaatgt aaatattgtt attcttcttt tgagttcccc | 1500 |
| tattatcatg ctgtttgcca tatttcctca taactgaaca acccctttttt taataatctt | 1560 |

| | |
|---|---|
| gaaactaaat catatcttgt tgccgatcgt cttcaacgga atatatacct ttgctttctg | 1620 |
| aaaatctttt gttgaacaag ggtgagaata ttttaatctt tagatttggt attagtttat | 1680 |
| ttatttattt ttgtaaataa ataatacaat gattctaata attcttattg aggaaacata | 1740 |
| ttagacaaaa tttcattgaa aatcatttat aaaatttatg ctaaaattat ttcttgaggt | 1800 |
| tttttttttt aaaaaaaaaa tcaagccaac cacgtttctt aaactttaaa aattaaaatt | 1860 |
| gaaaattatt ttcccaaaat aaaaataaaa ataaaaaata ttttctcaaa ccaaacaaac | 1920 |
| cttcacgtct cttccatac agtcatttct gcaagttggg tttggttttc tcttcttcgt | 1980 |
| tcgtttcgtt gaaaagcgac ttttctctc tgcaactctc cctttcttc cttcgtagat | 2040 |
| cgaaagggaa tcttcttcca tggcctccaa gcggattctg aaggagctta aggacctcca | 2100 |
| gaaagaccct ccaacctctt gcagcgccgg tacaattttc ttcaccgaat ccttttctt | 2160 |
| tttacccct ttttgctctc tatctatccc aaacccttat taagcttcat atgttgctcg | 2220 |
| atctatgagt tttggaattt acacgtatgt gggtcgttgt gttttttttc cctcctcgtt | 2280 |
| tcctaggttt atttgggttt tgttatatgt gtttctagat gccgatttac gtacgttaat | 2340 |
| gtaataaatt gacaatcttt gaagaagcat gatgaggtgt ttgttctaag cttcatatcc | 2400 |
| caggttgtga cctcaaaaga ttatcgtcaa tatgatgttt tgtgagactt ttctggttat | 2460 |
| ccgaagaagc ttttcttggt taagagtgat aaccaacgat tcataagttt gttgtttaac | 2520 |
| tttgtttgct attaattggt atcaaatatc tttatttttt taaaatcaat tcctctctgt | 2580 |
| gttctttcta ctgaagttga aatcctgcat tcaaagtgtc gtgactgctt agaaattaga | 2640 |
| atctctctag tctctattgc cttctttat cagagatttt ctctaagtct gtgttttgga | 2700 |
| tttgtgacaa ctatcatgga ttgaagatag agagactatt gtgattatct ctgtcttgg | 2760 |
| ttgtagaatc cattggaaga taactcttac tttaagattg tatatggctg acattattat | 2820 |
| ctttctagat gtttattatg tatctgagtt gcatgaacat actcatcaaa caagcagata | 2880 |
| taactcataa gttgtgagtc tgtatatatt tgaaaattt gtttaaactg cattctttag | 2940 |
| tctgttacac attattcatt attttccgat accatattgg aaaccaatgt taagtttgtt | 3000 |
| attttctaat gattattaca tttcataggt cctgtagcgg aaga | 3044 |

```
<210> SEQ ID NO 16
<211> LENGTH: 3151
<212> TYPE: DNA
<213> ORGANISM: Artificial Sequence
<220> FEATURE:
<223> OTHER INFORMATION: Synthetic polynucleotide

<400> SEQUENCE: 16
```

| | |
|---|---|
| ttagaaggga acatcaaaga gtccacttca tatgtgaccc tcagaagctc aacattggga | 60 |
| gagtgaatgg tctccctaga ccctgtcatt ttcttagcat cattctctgt tctaaacatg | 120 |
| taaaatccaa catctccacc atcccctcca ataaactgaa cacatggaaa aggctgtttc | 180 |
| ttgccaggcc aatccgaatc tttcccaacc cggacgccaa acaagtgccc cggacgcagc | 240 |
| ctcttccacg gctcagttct atacaaagct gcagaagctt tgtatataga tttaataaaa | 300 |
| tttggagcaa tgccatccac tttcatcatg catgtcccag atccagggcc aagaccagga | 360 |
| ccagacccaa attgctcctg aaatctgtca acaaactct tcaaatgcaa atccattgtc | 420 |
| tccccaattc ctcagattct ttttctttct atgctcgcaa ttcactccag tgaaactaaa | 480 |
| tctgtccgct tcaacacttg aaattatgca ataactctga tctcacaaat tctcacaact | 540 |
| ctactccact tcaacaaccc aaattcccgc tatgaagtag cactagactt aacaaagcaa | 600 |

```
aatgccaaaa cgcatttggg tacatgagta cagcttatga aatcagcacc cactcaactt      660
tgttcatgca acagaaaaca gataataaaa caaaaactga tcggaccata agatcaattg      720
tttcaaattt tcaatcagaa agcaaaagaa aaaagttca aagcttttgg ttcgtaccag       780
cccgcaaaac agtgaccgag ttgtgctcca agacccaat tccgaaacgt ttcattttcg       840
gacataaatg gaattgacgg gtaaagtcat atcatgcggg cattcgtatt tgtgacctgt      900
gagctcggaa ttcccatcag gaaattgaag ccattgaagt aatcaacgat cagaaaacga     960
tttgctaaaa tataatcaac ggtcaaaaac ttattgcaag agttttcttt cctttttatg     1020
aattgaattt gcaagagttt atttacgaac tatttaaact tattgtacca cagatattca    1080
tgtaagtatt cgaaaaacat gtaaaagaa cttaacattt atatgaaaaa gtttatttct    1140
aaattttctt tgataataac aatattttca tataaatatt aaacaaatgt ttattcaata    1200
agttttttta attaatatca ctaaatttaa aattgattaa actgagtata aaaaatataa   1260
attttgttta tttagaaagg ggttttatat ttagttttaa aattaattta aactaagcta   1320
attcaaagtc gatttataaa atatatgaac tataattata attttaaagt tgatatcact    1380
ttcaaattaa gatatatgtc ttatcctaat taaatgtact aaatctttaa tttagttttt    1440
ttttcaaata tatcttttaa tttgattta aatttaattt aattatcatc taaacatttt    1500
ttaaaattat tttagacaac tctcattgta tcattatctg tatatttagt ttttttttaa   1560
ctgcgtatct ttatttttaa attaagtttt ttatctgtgt attagaaagc tgtcttttt    1620 acacaaaata aaaaaaaat caaattaact ttcaattttc tttgacagca atcaaatcaa    1680
ataattattc gcccaaaaaa aatgaagctc gaaatacata ggtttaagtg aaggaagaag    1740
aggacgtcaa tctctgacac gagtacagag aacatgcgtc gtttgcagca gcagccaatg    1800
agaatccccc acctaatcac ccaaacgata aaaatccaat caatctttta attaataaaa   1860
aataaaaaat aaaaaataaa aaaccatagt gcccatcacg cacgcacctt acttacctta   1920
ccaataccat cccctttta gggttagggt tgtgagtctt cctttaaagg ggcatcgaga     1980
ctcaatctct ttctctctct ttcttgccc tctcttctc tctctagaat tctcagattt     2040
gcggggcgag atgatgcagc agccaggacc cggcatggca cctcccacca tgggccagca   2100
gccgccgcaa cagtaccagc agcctccgcc gcagcagcag caaccctacg tcatgatgcc   2160
gccgcaggcc caggccccgc aggccatgtg gcccctcc gcccagcctc cgcctcagca    2220
gcagcccgcc agcgccgacg aggtccgaac cctctggatc ggggatctgc agtactggat   2280
ggacgagaac tatctctata cctgctttgc tcacaccggc gaggtataat aataattagt    2340
atcccttctc tttcctttat ttcaagttga tttgttttca ttagcctatt gaatagacct   2400
tttgttttct acgtgaattt tgatcacttt taggtttttt ttttaaatgt ttgtgctttt   2460
agtttgaata gggatttctg ctgtgttaat cgtggtttga atttggtatt gatttagacg   2520
tgcggctgtt ctgtcgttgt gatactgaag tgtcagtttt tggtgattg aaggtttaat    2580 ttttgtattg aattttggtg gtttgtattg ttagctgttt ttggctaaat tggttagggt    2640
tttctgcagc atgaaattag aaccttcta gattttgttt taaatgcccg tacttgttga    2700
tttatgctta ggtgtaagag tgttctgtta tgatactgag gtgtgggttt tgtagcattt    2760
taggttggat tttgtattca ttctttattt gtgttcgaca aagtcgaaga tggttctttg    2820
tccgttctag ttttgtattg agttagatgt tctgttgtga taataaatgt gttcgacaaa    2880
gttgaatctg gttttcggta tgtctgtttt aggtttttta aacacgtgca attgttagtt    2940
```

| | |
|---|---:|
| tgaattgtgt attgagttag acgcatgaat gctcggttgt ggtaataaat gtgttctaca | 3000 |
| aaggtgaata tggttttctg tttgtctgtt ctatgttttt ttaaacatat gtacttgtta | 3060 |
| gtttaaaact tgtattgagc tagacatgca aatgttctgt cgtgatacta aatgtttgtt | 3120 |
| ctgttttatt gtaggttaca tcggttaaag t | 3151 |

<210> SEQ ID NO 17
<211> LENGTH: 2814
<212> TYPE: DNA
<213> ORGANISM: Artificial Sequence
<220> FEATURE:
<223> OTHER INFORMATION: Synthetic polynucleotide

<400> SEQUENCE: 17

| | |
|---|---:|
| aataataggc ttctctgttt aggcgaaaat ttatcatctt ttcttgttta ttgttttgag | 60 |
| tttaattttt atatattgtt aatataaata gttttacatg gttgattagc tataaattct | 120 |
| aaatgtgact ttttaaaata attattcaaa aatttaatat ttttaccata aattattaat | 180 |
| attttttttg ctagtgatat gccagttaat ataaatatag ttttatattt tttattaatt | 240 |
| agaaattcta aatgcgacgc ccttattgta gaaatatgaa tattctctgc ttttatagta | 300 |
| tgtgcatgta tgacacaact cttcaaatgg ggaaattgag ttaaaatatt gttaggattt | 360 |
| tttataaaca aaggattta ttaataataa aaatgcttaa attgaacatg aatacataag | 420 |
| agtccaaaca cagcattgtt tcaatcaaaa gcccaaggaa ttgaagaaag ccaattacaa | 480 |
| gccattaaag ccacatgaca attaacccc aaacacgttg taatcccatg gaagctttca | 540 |
| atgataaaaa agaaatacgt acatgatcca cctttacgta gcatacattt gctttcaaag | 600 |
| ttgttcatgt ttcatgataa gttcatgtag aacatgccc tgcttttaat caaataagca | 660 |
| tgactgacat caaaatgagg attgattgat tgtcgtcaat aacattgtta ggaactgtca | 720 |
| tgtcctcaca ttaatgaatt ctctattttt atttttttt aatttagtag cacgtaagat | 780 |
| tataaaagtc acaaaaaact caagtgttat tattaggaga gtaaaaaatg atatacaaat | 840 |
| atcataaaaa taactaatta aaaaataatt actattatgt aaaatcatta aaaaaataaa | 900 |
| attactcgta agagatatat tacaaaaaat tattaattta acttatacag tatgaactta | 960 |
| attatgttca cctttattga tgaagtttat tcactgttat tgtcatttgt gtgataagag | 1020 |
| ggaagaagaa gagatgaatc aagttgagtc agaggcagca gatgaaacca ttcaaggggt | 1080 |
| agtaacagac acaacacagg tgcaagaaga agcagagaaa accaaaagag tagtgaggaa | 1140 |
| gcccacttac ttcaaggact ttgtctaaag ggtgaagtgt gtatttccat aacaaaatca | 1200 |
| tcaacaaaca aattctgtta ctaggattac tataaataca attgtaataa acaagcaaag | 1260 |
| atatgaatga atgaaatttc catatttctt acttttcttc tttggagggt tctggtcctc | 1320 |
| gaaaccaaat tcttagttct cttaccaatt tgtctctttt tggttggtta ttcagtgtaa | 1380 |
| caaaataaaa aaataagaa ttatgaatct aaataatggt atacatgaca aagagatata | 1440 |
| gctcacattg acaactaaaa attgaattac tgatcacttg cattttcatt tatcttttac | 1500 |
| accagcgaca accaaattga tcatacaaca tttgaaccaa cttttcatgt ttaattttct | 1560 |
| atgtgtaacc atatactgca tagaggacca tacatgtacc ttttgcatgg tgcatacacc | 1620 |
| tctaacttat attgtgaaaa caagtttagt ttctatttgc tagtgttgtt acacaatcaa | 1680 |
| atttgttctt atcattcttt ttttttgtgt gaaagttaca ttcttaaata agtattatgg | 1740 |
| aataagcttt catattactt aactttattt cttactcgtt atttcaaaag gtgaaaatta | 1800 |
| catttctacc cagacacaca ctaaatacag tacaaactcg aagcaaatga tttggattga | 1860 |

```
tttaaatcaa ttttaggttc acaagggcaa ggggtggaat ataaagaaga aagaaatgga    1920
taagggtgtc atttggtgtg ggcatatatc caaccaaaaa gggacatttt gcgggtattt    1980
gtgagtgtgt gagagagaga gcgagcagtt tcagacacag agagaggggt ttgggattgg    2040
agggattgac gctgcgtctc ttcctcttct ctttcgatcc atccctcatt cctaatcctc    2100
caatccaacc acctcagcct cacactcaca tatacacatg tctctctcta tttcccttt    2160 cactttcact ttcatttcta gggttccgtt ctgatggctc tttcccttc agatctgaac    2220 gcgtatcgtc cctcctatgg cttcaaagcg catcctcaag gagctcaagg acttgcagaa    2280
agacccacca acttcttgca gcgctggtac ccctttttctt ctccattcca ctcccccacc    2340 acgattttt tgtccgcact atttgggatg tgataaaaat ctattttttt cctgggttc    2400 tgtttgttct agggtaaat gaaataaatt taaataagcg caaattaggc tgtttctgcc    2460
acattttgta agctatgtac gtgtgattct atgtgtgcac tcttactaac cttgctgggg    2520
taaaataaaa ttatacaagt tcatgagaaa ataaatcata ggaaatatga taactgtctg    2580
tacaaggttt taaattgtgg tcccgttgtg ttccttgatg tcgcaggaaa ttgtgtttaa    2640
gtagatgttg caaccgaaat aatggttgcg gaccttttt aaaaccttgt gtgtgtttat    2700
gttgtgagtt tgagccatac atgttttatg ttgtgagttt gaaccataca tgttttgttt    2760
gtttgtagta tgtgcaaata caaatgttta ttttgtaggt ccagtagctg agga           2814

<210> SEQ ID NO 18
<211> LENGTH: 1614
<212> TYPE: DNA
<213> ORGANISM: Artificial Sequence
<220> FEATURE:
<223> OTHER INFORMATION: Synthetic polynucleotide

<400> SEQUENCE: 18
tccaccctca caaaaaaggt tattgcctaa ttaatagtag ggattgaaga agtatcaata      60
atcaataaga gggacatttg gattgacaca aactattagt ataaaaaaa aatgtaaaac     120 taaatggaca acaatctaag aaagcgagta tgtgttgtac tcggaaaaca taacataatg     180
tgattttgat tgtggaaact gaaaacaata acatttaagt tttattttatc tctttgccta    240 acaatttttt taattacttt ttttatagtt tttatgatga agataattaa tattttttac     300
aaatattata ttttccttt taccatcttt gaagataatt gcttttttt ccaatttaga      360 caaatatttg agtatcaatg atattccttt ttaatccatt attgcaattt aaaagaccat     420
caatgattac attttcaatc aaatgacttt attagtcttc actttacatc gatttaaatc     480
aaactaataa ttttgtatgg actaaatctc tgaacatttt tatatttaca acatattta      540 acatttatta ataattagt atttaatact attagtagaa taatgggagt agcaggaggg     600
aggcactgag agaatagaga tggcatggaa gtaagcaatc aagtcaaaat cagagttggc     660
caaccccaaa ggctgtagta ggtaagcatg gcccattta gttttacat tcatctctca      720 ttttcacctc aacggttcag attcaatctg actccccgat ctcagccgtg gattcaaatg     780
ccacctcagg cacatgcaat tccaaatgga tgaacctaac ccacaatcta atcttgttac     840
ttaggggctt ttccgtcatt aaatgacacc acctacccc ttctccctat aaatggcaac     900
tcaatgcccc ccttagaact cgcagcgctt gatttgaggc caggcaagcc ccactcaacc     960
accacacctc tcctcgttca cgctacccct ttctgctctt cttctacctt tcaaggtact    1020
cttctttccc tctgttgctg caaccttctc tttctttaag attgcctcaa tttcggatct    1080
```

-continued

```
tgcacctctg ggttgctttg cttttgcttt tcctctactg ggttgatttc tgtttcccta      1140
aaccggttta gacgaatgtg aacactactt cttttgttta attactctgg aatacgtgtt      1200
aggctttcag atctagttga aatcgtattg cacttttagg gggagtttgg atttctaata      1260
agaaattgac cttttgctga gaattggttc ggtgattaga gggtttccgt aaattttgta      1320
agttttacat gcttgtatct gtttattttt gtttctcaca tctattattg ttaggtgaag      1380
gaaattatgt attgagagtc tgtctgatac taaatataaa cacctcaata ggggctctaa      1440
cactgatttt atcatttgct gcttgtgtgt atggttaaag aaaggcaatt gtgtttttaat     1500 tttctgcaag ctttcgtttg ctgaattta tgcatatatt ttcctcccctt ttgtgaactt     1560 cctttttgta gttctaattc cattttggt gtctgcagtt ttaaaagtat aaag            1614
```

<210> SEQ ID NO 19
<211> LENGTH: 1951
<212> TYPE: DNA
<213> ORGANISM: Artificial Sequence
<220> FEATURE:
<223> OTHER INFORMATION: Synthetic polynucleotide

<400> SEQUENCE: 19

```
gcttcaaact tgtatgggga agtgaactag ctgttaaaac aatgagtgga ctcgtgatcc        60
ctcactcaaa cagaaagcat aatgcgaatt gctaaaaggg gtccagaact gccttggcta      120
ttttttacgt gtgtttctta attaggagcc acgagacaaa gatataaagg ttagtgtagg      180
accctgccac ccaaaatctg cctggatatt atgcatgcgt ccctaacctt gttgcttgtg      240
gcttttgcca gagtagaatg acgaagaaaa ttttcaaaag attcctaatg ttttttggctc     300 acaactcaaa aactcaaact gatcaagaac cgttcatttt attaacgtta tccttacaag      360
tcactcaggc taatcgagct ggtactaaac taatgcatat taggtaatgc aaataaataa      420
taacgctccc aagaatattc aaatggtttc ttttgctttt tgcttaacga cttttgtatc      480
tctacgtatt acttgagaaa aaaagctgct attattatcc aactaaacaa atgaaagcta      540
cagttaagga catggcctat taacaatatt acgtagactt gatcattgtc tcatccacga      600
gatagaaaca aaatatataa aagggctcat tatgcttatt tagttcatca agaagctagg      660
aaaatgagta cgtagaatga acatttaata atggacgtga gagaagttaa tcgctgacag      720
ccatgtgccg accatgtttt tataaatgaa aagaaagaa atgttcgtat ataataatta      780
acggacacaa gaaccttgtt aataattatc attatctttt ttttttttgtt tttattttcc    840 gaaaaacttg tttctccaat cattgatgtg tatttctatt ctctctccat ttccaactcc     900
tgactgagaa gtggatttca tatcaacatt agcaattagt agaatactat catctttcac     960
gctacaaaac attggtactt tggtaggtaa agatttgcaa acacgaataa gtaattaaga   1020
aaggttcata cacattcaat gattctggat tcctacctta cgttatttgt ttcgaaatac   1080
ctagatgaga gcatcttgtt atttattact acatatataat tttccctgtg taccttgtcg   1140
tagtttaaat ttattatttt ttcaatcata ataaatata agaaatattt ttttcttaat   1200
ataattttat tttatatttta aaaataaatc ataatttgaa agagctacaa atttataccca   1260 catgtgggaa gtattgttgg tttctccaac catactattat gagaataact tgaatttata   1320
ttcaacgtat taattgcttc acctttaacg tgccaaaata ataataataa aaaacttaaa   1380
actactgtat taatcgcgtg tggttgaatg gaggcaaatt ctattctaaa aaagaaaagc   1440
attaacaaaa ggagaaaaga aaaactgttg acacctgaca gcagtaacag ggaactgggaa   1500 agtagcagta ggagtatttg cgtgttggtt tccaactctg gaatccaccg tgccaaactg   1560
```

| | |
|---|---:|
| cgaatgcagg agaaatcgac acgtgtccat ttgcaggcgc gagttgaacg tgacaatgca | 1620 |
| ccaccgccca gcatcgaacg cagccaagga ccacgtcgaa accacagtaa tccacgttcc | 1680 |
| agtgctgcgc ggaacatggt cggtctttct aggagtggtt ggaatcacgc cagctaggac | 1740 |
| aaaccccatc aatcattggt cattatcaaa caaaacattt caaaaattca acatattacg | 1800 |
| cctcgggacc cacctcccac tacacctcac cctcacttct attaactcga acacattcgg | 1860 |
| gttataaatc cgcaaccctc cttctcactc actcactcac tcactcactc actcgcaagc | 1920 |
| aaaaagaaag aatcccaggc gaggagaaag g | 1951 |

<210> SEQ ID NO 20
<211> LENGTH: 2009
<212> TYPE: DNA
<213> ORGANISM: Artificial Sequence
<220> FEATURE:
<223> OTHER INFORMATION: Synthetic polynucleotide

<400> SEQUENCE: 20

| | |
|---|---:|
| gtgaatataa agggcaccgc tcgttgttga tgagaacacg aaatctcctc tccacaatgc | 60 |
| aacgtcaaga tgtcatagac aggtatggaa aggaaaaata aataaataaa taaatggatt | 120 |
| ttatgctcca cccagtttgc ccttcctgaa tgctaacaaa actcaacatg ttttgaata | 180 |
| gggtaataat cggggttggt ttttgttgt tctcccttgc tgttctttat gttgtttcca | 240 |
| agcgaattgg actacttacg ttgcaaagaa aggttactga ggccataaaa gctggtatgg | 300 |
| tgggacaggc agagctaagg ccccaagctg ttgcagatga cgtgaatctt catcaagtca | 360 |
| gaggcaatcg tgttcctaat aatgcagagg ctcctttaga acaaagaatc catgatgaac | 420 |
| tatgatgcat ttctaagcaa tactatcatg ttatgtgtgt ttataacaca actcttctaa | 480 |
| ttcctttaaa agtaacgaaa gtaaaaagta ttttgctatc ttgagagttc gaaaagcatt | 540 |
| taatactacc tttttgagaa ttattggctg atctgttata atgaattaaa aattctttct | 600 |
| gtagttgttt ttgtctacgc tacaggcctt tcaacatgag caagctaata attgttgacg | 660 |
| agctgtctct ggctgctttt tcattgtacc aatgcttgtc tcctacacat caactgtatt | 720 |
| taagatctga agctgacatg agattttaca aagcattata taattacatt ggcgccacaa | 780 |
| taatttcgag atatttatca aaataaataa agttgcaaat gcaatggag ttcacatgca | 840 |
| atgaatccct tgtcataaac tccaaaatca tgattgcaac ataaacaaat gttttagaaa | 900 |
| aattaaaatc tgtggcttac gccctcatgc acatgttttg cgtgatgatt aacagttgtt | 960 |
| acagctccct ctttctgagt cgtggtaatt tgaggtaaat ttgcgtgatg aactagtaag | 1020 |
| ttttatttc cagtgaagca actgctacag gcttgggtgt tggagaaatt taccattgag | 1080 |
| ttatgcaata gttacctgga ttatccttac tttttataat agaaaaataa tccttttaat | 1140 |
| aaactcgttt agattctgtt tatacaaatt tggtagatta aacaaattat cacgtgacac | 1200 |
| aaatatttct atgattgctt aaaatagaat aaaagaatt tagttgaaat tgttttttat | 1260 |
| actgttgatt ttgaatagaa taatatggta aaatggtcaa ttcttattgg atatttatgt | 1320 |
| aagaatattt tgcattgaaa ttgtctagaa tatttttaga catataatat gatgggtaaa | 1380 |
| taatggtgtc cttcgaagtg tatgataaaa gattcatttc ttagactcat gtatagtaaa | 1440 |
| aaaaaaaaag gagtgattag ccccttaaata aatcttgata tcttgaagaa ttaatatttt | 1500 |
| acttttgact gaagaatgtg ttggataaat ttctatttat taatatgata tggcgtggtt | 1560 |
| gtaaagtaaa tttctactag aaatttgtgt aaaaactgaa gtcttttgt gtaagaatgt | 1620 |

```
gtaaatagtt gattaattta atccatatag taatgtgtat ggacaaagta tagtatctgg    1680
gaccctgaga ttataatgtt tggtaaaatt tgggaggtgg aacgaggtca ggggacgaca    1740
catttggtcg ggagaccgtg aaatttacgg tacgggacaa cacaattggg ccctcaagcc    1800
ccaattcagc ccaatgggct atcgaaaaga aagaaagaaa gtttgtgcgc tgcggatatt    1860
aataattttg tgacgctcca ccacatttcc ccattcccaa atttctcatt ctcccatttc    1920
ctctcagaac cctcgatcac tcccacgcgc tcctatatcc tctccttcac cgtcgctctc    1980
tccaacgatc acaacaacat cgtcatccc                                     2009
```

<210> SEQ ID NO 21
<211> LENGTH: 2345
<212> TYPE: DNA
<213> ORGANISM: Artificial Sequence
<220> FEATURE:
<223> OTHER INFORMATION: Synthetic polynucleotide

<400> SEQUENCE: 21

```
ttgacgagct gtctctggct gcttttcat tgtaccaatg cttgtctcct acacatcaac      60
tgtatttaag atctgaagct gacatgagat tttacaaagc attatataat tacattggcg    120
ccacaataat ttcgagatat ttatcaaaat aaataaagtt gcaaatgcaa atggagttca    180
catgcaatga atcccttgtc ataaactcca aaatcatgat tgcaacataa acaaatgttt    240
tagaaaaatt aaaatctgtg gcttacgccc tcatgcacat gttttgcgtg atgattaaca    300
gttgttacag ctccctcttt ctgagtcgtg gtaatttgag gtaaatttgc gtgatgaact    360
agtaagtttt attttccagt gaagcaactg ctacaggctt gggtgttgga gaaatttacc    420
attgagttat gcaatagtta cctggattat ccttactttt tataatagaa aaataatcct    480
tttaataaac tcgtttagat tctgtttata caaatttggt agattaaaca aattatcacg    540
tgacacaaat atttctatga ttgcttaaaa tagaataaaa agaatttagt tgaaattgtt    600
ttttatactg ttgattttga atagaataat atggtaaaat ggtcaattct tattggatat    660
ttatgtaaga atattttgca ttgaaattgt ctagaatatt tttagacata taatatgatg    720
ggtaaataat ggtgtccttc gaagtgtatg ataaaagatt catttcttag actcatgtat    780
agtaaaaaaa aaaaggagt gattagccct taaataaatc ttgatatctt gaagaattaa    840
tattttactt ttgactgaag aatgtgttgg ataaatttct atttattaat atgatatggc    900
gtggttgtaa agtaaatttc tactagaaat ttgtgtaaaa actgaagtct ttttgtgtaa    960
gaatgtgtaa atagttgatt aatttaatcc atatagtaat gtgtatggac aaagtatagt   1020
atctgggacc ctgagattat aatgtttggt aaaatttggg aggtggaacg aggtcagggg   1080
acgacacatt tggtcgggag accgtgaaat ttacggtacg ggacaacaca attgggccct   1140
caagccccaa ttcagcccaa tgggctatcg aaaagaaaga aagaaagttt gtgcgctgcg   1200
gatattaata attttgtgac gctccaccac atttccccat cccaaatttt ctcattctcc   1260
catttcctct cagaaccctc gatcactccc acgcgctcct atatcctctc cttcaccgtc   1320
gctctctcca acgatcacaa caacatcgtc atcccatggt cggtttttt ctctaatttc   1380 tctcttcctt ttttcgttat ccgatttgtt ctcacgcatc aataactaaa tccgcgaatt   1440
tctagcgttt ttttttttgt tgaatttagt ggcgtcgaaa tttctgagct ggattcgtat   1500
ttgatctgat cgtttaactt gaacggtgct tttttatttt tttgttaaa ataaaggaat   1560 aaatcgtggc gatttcagat ctgatttcgg tgcttcggtt gagttttttcc caaattcata   1620 gcttattatg atattttat tgcggatttc agtttacaac agcttgtgat gtgtgatgtg   1680
```

-continued

```
tttgatctgc gcagaaatcg gttgtgatct gacatgtgga ttgattccat tttatttatt      1740
ttattctaat tttaatttta tgagcatgtt gatttaactt cttttatgtg ataattatgc      1800
gtggaaattt caattaaagc atatattctt gtcttttttt ttgttttttgg ttgcatatat    1860 tcttattctt tcattagatt tattttaatg atgtttctat attagattta ttaatgaata     1920
aatatgattt tattttggga ctgaagacac gacaaacgta acacggtttt cttaattttt     1980
attgatgttt acttgttttg gcactaatca ctgtctgctt ctatccccett gatttggaag    2040 ataccgtgtt tgtggaagta ttatttactt atttagttgg tcgcatattc ctataatatt   2100
tcattgttat caatctacga atttagtctt ttttttttgg taagcaattt gatttacttt    2160
atggcatatt tcaacccaat tatgttaaca agttaacaac cctttgtttt ttttctttcc    2220
cggagtaaca atttaaatgg gaaaaaaaaa agattaacaa catatttgtg cacaattact    2280
tggtattgat gaccatggtg gtgtgtgtct gcaactgcaa ttctataggc aaacgccgca    2340
tctgg                                                                2345
```

<210> SEQ ID NO 22
<211> LENGTH: 1353
<212> TYPE: DNA
<213> ORGANISM: Artificial Sequence
<220> FEATURE:
<223> OTHER INFORMATION: Synthetic polynucleotide

<400> SEQUENCE: 22

```
gacgagctgt ctctggctgc ttttcattg taccaatgct tgtctcctac acatcaactg       60
tatttaagat ctgaagctga catgagattt acaaagcat tatataatta cattggcgcc      120
acaataattt cgagatattt atcaaaataa ataaagttgc aaatgcaaat ggagttcaca     180
tgcaatgaat cccttgtcat aaactccaaa atcatgattg aacataaac aaatgtttta     240 gaaaaattaa aatctgtggc ttacgccctc atgcacatgt tttgcgtgat gattaacagt     300
tgttacagct ccctctttct gagtcgtggt aatttgaggt aaatttgcgt gatgaactag    360
taagttttat tttccagtga agcaactgct acaggcttgg gtgttggaga aatttaccat    420
tgagttatgc aatagttacc tggattatcc ttacttttta taatagaaaa ataatccttt     480
taataaactc gtttagattc tgtttataca aatttggtag attaaacaaa ttatcacgtg     540
acacaaatat ttctatgatt gcttaaaata gaataaaaag aatttagttg aaattgtttt     600
ttatactgtt gattttgaat agaataatat ggtaaaatgg tcaattctta ttggatattt    660
atgtaagaat attttgcatt gaaattgtct agaatatttt tagacatata atatgatggg   720
taaataatgg tgtccttcga agtgtatgat aaaagattca tttcttagac tcatgtatag     780
taaaaaaaaa aaaggagtga ttagcccctta ataaatcctt gatatcttga agaattaata    840
ttttactttt gactgaagaa tgtgttggat aaatttctat ttattaatat gatatggcgt     900
ggttgtaaag taaatttcta ctagaaattt gtgtaaaaac tgaagtctttt ttgtgtaaga   960 atgtgtaaat agttgattaa tttaatccat atagtaatgt gtatggacaa agtatagtat    1020
ctgggaccct gagattataa tgtttggtaa aatttgggag gtggaacgag gtcaggggac    1080
gacacatttg gtcgggagac cgtgaaattt acggtacggg acaacacaat tgggccctca    1140
agccccaatt cagcccaatg ggctatcgaa agaaagaaa gaagtttgt gcgctgcgga     1200 tattaataat tttgtgacgc tccaccacat ttccccattc ccaaatttct cattctccca    1260
tttcctctca gaaccctcga tcactcccac gcgctcctat atcctctcct tcaccgtcgc   1320
```

```
tctctccaac gatcacaaca acatcgtcat ccc                              1353
```

<210> SEQ ID NO 23
<211> LENGTH: 974
<212> TYPE: DNA
<213> ORGANISM: Artificial Sequence
<220> FEATURE:
<223> OTHER INFORMATION: Synthetic polynucleotide

<400> SEQUENCE: 23

```
aagcttttc  tagatataaa ataatgcggg tttcagtttt caattgataa attaatagtt    60
aatattttta taaaaattaa aatatacaaa aataaagtga taaaaattaa taaattttct   120
atccttttg  agttttgct  ataaaaatct aaggagaagt tccctggttc ggaactgacg   180
tagaccaatt ttgtaagaat cgacaatgac gggtctttc  cgatccaaat ggtccctcca   240
cagtccttag atcaatcctt gtccacattc acttggcccc atctccatgt tttctcacat   300
caactaattc tcaagcaaaa aaataaaata ggttctttga aggaatgata cagtgaccaa   360
tttaattttt aaatatgtaa aaattatgat aaattaattc tattaaattt gtgaatttat   420
tttattatta agttataata tttaatgact aatttgataa tatattatat ttttaagatt   480
aatttgatat taaaggataa aatttatgat caatttttt  attaaattat atgttaaaat   540
taatttattg tatttttat  atatttggag attaaatttt ttttctgtt  cacactttgt   600
cagcactttt gttgttttt  ttttcaaaaa gagaaaaaga gaatataaat ttaaatttaa   660
agcagaagag aacgaagcgg cgtcgtttgt tgcggcctga aaaagtcca  cactcgtgaa   720
agtcattggc ataatgacga gcatatccgt gagtgacctc ggatccgctc cactaaccct   780
agtcaactcc aaactcaacc atagttactt tacttcactc acacccgcc  acgtgttcca   840
atcgaacggt cacttctgca tcacgcgcca ctataaatat ctctctctcg tcatccgcaa   900
ccccaagcaa aaccctaatc cctctttctt cctcttcctc agtagtgcga ttttcgattc   960
tcttctctgc aact                                                    974
```

<210> SEQ ID NO 24
<211> LENGTH: 760
<212> TYPE: DNA
<213> ORGANISM: Artificial Sequence
<220> FEATURE:
<223> OTHER INFORMATION: Synthetic polynucleotide

<400> SEQUENCE: 24

```
aagcttttc  tagatataaa ataatgcggg tttcagtttt caattgataa attaatagtt    60
aatattttta taaaaattaa aatatacaaa aataaagtga taaaaattaa taaattttct   120
atccttttg  agttttgct  ataaaaatct aaggagaagt tccctggttc ggaactgacg   180
tagaccaatt ttgtaagaat cgacaatgac gggtctttc  cgatccaaat ggtccctcca   240
cagtccttag atcaatcctt gtccacattc acttggcccc atctccatgt tttctcacat   300
caactaattc tcaagcaaaa aaataaaata ggttctttga aggaatgata cagtgaccaa   360
tttaattttt aaatatgtaa aaattatgat aaattaattc tattaaattt gtgaatttat   420
tttattatta agttataata tttaatgact aatttgataa tatattatat ttttaagatt   480
aatttgatat taaaggataa aatttatgat caatttttt  attaaattat atgttaaaat   540
taatttattg tatttttat  atatttggag attaaatttt ttttctgtt  cacactttgt   600
cagcactttt gttgttttt  ttttcaaaaa gagaaaaaga gaatataaat ttaaatttaa   660
agcagaagag aacgaagcgg cgtcgtttgt tgcggcctga aaaagtcca  cactcgtgaa   720
```
agtcattggc ataatgacga gcatatccgt gagtgacctc            760

<210> SEQ ID NO 25
<211> LENGTH: 974
<212> TYPE: DNA
<213> ORGANISM: Artificial Sequence
<220> FEATURE:
<223> OTHER INFORMATION: Synthetic polynucleotide

<400> SEQUENCE: 25
aagctttcct attagtcttt tcttatccat aaaaaaaaaa aaaaaaatct agcgtgacag     60
cttttccata gatttaata atgtaaaata ctggtagcag ccgaccgttc aggtaatgga    120
cactgtggtc ctaacttgca acgggtgcgg gcccaattta ataacgccgt ggtaacggat    180
aaagccaagc gtgaagcggt gaaggtacat ctctgactcc gtcaagatta cgaaaccgtc    240
aactacgaag gactccccga aatatcatct gtgtcataaa caccaagtca caccatacat    300
gggcacgcgt cacaatatga ttggagaacg gttccaccgc atatgctata aaatgccccc    360
acacccctcg accctaatcg cacttcaatt gcaatcaaat tagttcattc tctttgcgca    420
gttccctacc tctcctttca aggttcgtag atttcttctg ttttttttc ttcttcttta    480
ttgtttgttc tacatcagca tgatgttgat ttgattgtgt tttctatcgt ttcatcgatt    540
ataaattttc ataatcagaa gattcagctt ttattaatgc aagaacgtcc ttaattgatg    600
attttataac cgtaaattag gtctaattag agttttttc ataaagattt tcagatccgt    660
ttacaacaag ccttaattgt tgattctgta gtcgtagatt aaggtttttt tcatgaacta    720
cttcagatcc gttaaacaac agccttattt gttgatactt cagtcgtttt tcaagaaatt    780
gttcagatcc gttgataaaa gccttattcg ttgattctgt atggtatttc aagagatatt    840
gctcaggtcc tttagcaact accttatttg ttgattctgt ggccatagat taggattttt    900
tttcacgaaa ttgcttcttg aaattacgtg atggattttg attctgattt atcttgtgat    960
tgttgactct acag                                                     974

<210> SEQ ID NO 26
<211> LENGTH: 442
<212> TYPE: DNA
<213> ORGANISM: Artificial Sequence
<220> FEATURE:
<223> OTHER INFORMATION: Synthetic polynucleotide

<400> SEQUENCE: 26
aagctttcct attagtcttt tcttatccat aaaaaaaaaa aaaaaaatct agcgtgacag     60
cttttccata gatttaata atgtaaaata ctggtagcag ccgaccgttc aggtaatgga    120
cactgtggtc ctaacttgca acgggtgcgg gcccaattta ataacgccgt ggtaacggat    180
aaagccaagc gtgaagcggt gaaggtacat ctctgactcc gtcaagatta cgaaaccgtc    240
aactacgaag gactccccga aatatcatct gtgtcataaa caccaagtca caccatacat    300
gggcacgcgt cacaatatga ttggagaacg gttccaccgc atatgctata aaatgccccc    360
acacccctcg accctaatcg cacttcaatt gcaatcaaat tagttcattc tctttgcgca    420
gttccctacc tctcctttca ag                                             442

<210> SEQ ID NO 27
<211> LENGTH: 1335
<212> TYPE: DNA
<213> ORGANISM: Artificial Sequence
<220> FEATURE:

<223> OTHER INFORMATION: Synthetic polynucleotide

<400> SEQUENCE: 27

| | | | | | |
|---|---|---|---|---|---|
| taagccatag | ttgcatatca | tatctctatc | tcaaatattg | aacatgtaat | ttatttattt | 60 |
| tttcttttaa | aatatattct | ttaatttaaa | ttttgaactt | gatttgattt | aacaattaat | 120 |
| ccaaaaattg | attttcagtt | acgtcaaatt | atttcaatta | cctcaaatca | cttttctttt | 180 |
| gtctttattt | gtctaattat | ttttttaact | actaatcttg | tcttaaaatt | aattttaata | 240 |
| tttttaaaa | aatgatcagt | agttaaaatt | aattttatat | cacaatacaa | attatttatc | 300 |
| taacaaaaca | gataactaat | attcaaatac | aattatctct | acgattaaaa | agtataaaaa | 360 |
| gggaagcaaa | atatttatct | aaaaaaatat | tattatcttt | ttaatgaaaa | aaataaaagg | 420 |
| ataacaaaat | attttgttaa | aaagtaaaaa | aaaagtaac | actaaaatat | tattatctct | 480 |
| aaagtcttat | tccaccaaat | aaaaaaatca | ccataacgtt | aaaatattat | ttatgctaaa | 540 |
| aattctaaaa | agccagtggg | ccaatgcctc | cacccttaa | aatagtttca | cttccactcc | 600 |
| cgaaaagggt | tcaatttaaa | aaaaaattaa | aaagaagtct | aaaaacttga | ttaaataata | 660 |
| tcaaatagtt | tttttaagga | aaataatatc | aaatagttta | gaaacctacg | aggaatttaa | 720 |
| tcttatttt | atttattta | tctttactaa | ttacacatat | attcatcttt | caatatga | 780 |
| ctatatttaa | aagaaaaca | ataacctact | attgcttata | atggctaaaa | atacaatcta | 840 |
| tatataagct | cacacatttc | taatttcaaa | tgcagagaga | tattgagtac | agttattcca | 900 |
| caaggtggga | taattttatt | attcttcttt | tataaagtat | aaaatattga | ccaacaaaat | 960 |
| ctctcgacca | agtcagtcaa | ccatatatat | ttgatattta | ttttgtaaca | aaaacattt | 1020 |
| atatttattt | aggacgtaca | gataacgcaa | tgcgacgcga | ctttgtgcgt | aaggaccacg | 1080 |
| caacgtttaa | ttgttggcag | ccagcgcgtc | attgccgccc | ttgtaccaag | ccgccaatac | 1140 |
| gctactctta | ttttaccaaa | ataccctct | attattgtaa | agaaacagat | aacaaatagt | 1200 |
| tttttcccac | ccataaacga | gccgcaccta | atgttacacg | tcaccaaatc | ctcaccgtca | 1260 |
| acacaagcaa | tctcaaccgt | ccatgttccc | aaaaacccaa | tataaaataa | agcataggt | 1320 |
| tcccttctat | ctctc | | | | | 1335 |

<210> SEQ ID NO 28
<211> LENGTH: 2024
<212> TYPE: DNA
<213> ORGANISM: Artificial Sequence
<220> FEATURE:
<223> OTHER INFORMATION: Synthetic polynucleotide

<400> SEQUENCE: 28

| | | | | | |
|---|---|---|---|---|---|
| ggggagtgc | atttcctgct | gctagtattg | cccaagagga | aaaatgtctt | tgggacagaa | 60 |
| acaagagact | agctatctgt | ggagacttct | gtgtcagtcc | caatgttgaa | ggtgccatag | 120 |
| acagtgcctt | cgcagcagca | ttaaggctta | agatagtgt | cagctcttta | tagttggagc | 180 |
| attacaatct | gtagttctcc | aaaccttgca | tgcctttatt | tcagtttttt | ctcctgggaa | 240 |
| aacgtgttca | aaatttcttt | taagacattt | ctgtattact | aaacgcgaac | aaatttccct | 300 |
| tctacgacga | agccttgcac | actacaaagt | atgagaaaga | ggtacagggt | ggttgcacttt | 360 |
| tgccgtgcca | agtttgcagg | aaaatggtga | tgaaaccacc | tttgaaatca | acagtgttg | 420 |
| agtttagtct | taacaacaaa | aaataaggta | aacatatgtt | aagtgcacta | gatgatggcc | 480 |
| taatgtactg | taattctgaa | tttgtgatca | tgttatttcc | ttttagtttat | aactaaaata | 540 |
| catttcagaa | agcaccatgg | cttgacccaa | caaatatcaa | aatatcatca | tcccacatgt | 600 |

```
aatggttatt ttcaaataca gatatgtgcg tgtgtgctag gtttatttat ttcattggaa    660
taatgttatt tgatttaatt ttatctaaaa acagcttaat ttttatatgc ttgagaagtt    720
ggaattttcc tacagggtcc tgaattatat cataagttgg agaagttggt tttgctctaa    780
tggaggggac agagagacta tgttagtatt tccaatgcca tcccattaca atcaggacaa    840
aacaaccaca ccaataaatc cttcataagc ctgatttgca aaaacttttt gcactcccac    900
tattgtttcc tgcacttccc ataattgcat tacaaaatga acttgccgga aaacaatgag    960
aagcgcagaa agcaacagcc tgatagctat catagcttga tgatggattg aactttcaga   1020
atttaggatc ctctatgaca aggagttaag ggacaagccc ttttaggttt tgttgccgaa   1080
ctaacatgta atacaaacca agtcaatcaa aagacatgga tggattttaa aatgtcaaag   1140
gaagtagagc taggatcatc ttagagttta aaataagttt ttattttata ttttagtttt   1200
taaatttaat tatttattgt tattttagtt ttaaaagtac gataatatta gtcatatgag   1260
tttttaaatt ctagactaaa gtgagttaca tattaaattt tcaagatatt tttaaattct   1320
ggactaatat atatgtacta cacatcaatt tttttatact aacaaaatta tttattgtca   1380
tgctagtcac tgtgtttttt tattgtattg tttatgtatt cagcctatga ttatgaatga   1440
aataatgaga tctttcctta aaaaaccaaa attatttact aatattgata gtataacctt   1500
ataaattaaa atttatatta ataatttaat ttctattaaa aaatgttatg ttaacgaaag   1560
ctaagggaat aactaaccat tataactttt tattttattt catttctctt aattaagaat   1620
ttatttcgtc cattctcttt ttaactgcaa ttctacagta gttttcaact taaaacattg   1680
atatgttgga aacctcactt tttttttccac cagaaaaaaa taaataaaaa tccgttgtat   1740
ttttcgtgga aggaatatcc acgtttcttt catcaagatg gatgttgaag attttgtttg   1800
cacatccata ttcataaaaa aacaggtgaa aaattgatct cattgagata atgtttacat   1860
tatcatatcc tggcactcta ccacaaatgc catgccacgt gccaccaaag caatcacaaa   1920
tacgtggcca ctattattat tatcacttgt ttttgtttcc catagcatag aagaagcaga   1980
aagagaagca ttagcaaaag caagaagaac tagtctaagc agaa                   2024
```

<210> SEQ ID NO 29
<211> LENGTH: 1414
<212> TYPE: DNA
<213> ORGANISM: Artificial Sequence
<220> FEATURE:
<223> OTHER INFORMATION: Synthetic polynucleotide

<400> SEQUENCE: 29

```
ggcaaataca gatatgtgcg tgtgtgctag gtttatttat ttcattggaa taatgttatt     60
tgatttaatt ttatctaaaa acagcttaat ttttatatgc ttgagaagtt ggaattttcc    120
tacagggtcc tgaattatat cataagttgg agaagttggt tttgctctaa tggaggggac    180
agagagacta tgttagtatt tccaatgcca tcccattaca atcaggacaa aacaaccaca    240
ccaataaatc cttcataagc ctgatttgca aaaacttttt gcactcccac tattgtttcc    300
tgcacttccc ataattgcat tacaaaatga acttgccgga aaacaatgag aagcgcagaa    360
agcaacagcc tgatagctat catagcttga tgatggattg aactttcaga atttaggatc    420
ctctatgaca aggagttaag ggacaagccc ttttaggttt tgttgccgaa ctaacatgta    480
atacaaacca agtcaatcaa aagacatgga tggattttaa aatgtcaaag gaagtagagc    540
taggatcatc ttagagttta aaataagttt ttattttata ttttagtttt taaatttaat    600
```

| | |
|---|---|
| tatttattgt tatttagtt ttaaaagtac gataatatta gtcatatgag ttttaaatt | 660 |
| ctagactaaa gtgagttaca tattaaattt tcaagatatt tttaaattct ggactaatat | 720 |
| atatgtacta cacatcaatt tttttatact aacaaaatta tttattgtca tgctagtcac | 780 |
| tgtgttttt tattgtattg tttatgtatt cagcctatga ttatgaatga aataatgaga | 840 |
| tctttcctta aaaaccaaa attatttact aatattgata gtataacctt ataaattaaa | 900 |
| atttatatta ataatttaat ttctattaaa aaatgttatg ttaacgaaag ctaagggaat | 960 |
| aactaaccat tataactttt tatttatt catttctctt aattaagaat ttatttcgtc | 1020 |
| cattctcttt ttaactgcaa ttctacagta gttttcaact taaaacattg atatgttgga | 1080 |
| aacctcactt tttttccac cagaaaaaaa taaataaaaa tccgttgtat ttttcgtgga | 1140 |
| aggaatatcc acgtttcttt catcaagatg gatgttgaag atttgtttg cacatccata | 1200 |
| ttcataaaaa aacaggtgaa aaattgatct cattgagata atgtttacat tatcatatcc | 1260 |
| tggcactcta ccacaaatgc catgccacgt gccaccaaag caatcacaaa tacgtggcca | 1320 |
| ctattattat tatcacttgt ttttgtttcc catagcatag aagaagcaga aagagaagca | 1380 |
| ttagcaaaag caagaagaac tagtctaagc agaa | 1414 |

<210> SEQ ID NO 30
<211> LENGTH: 2191
<212> TYPE: DNA
<213> ORGANISM: Artificial Sequence
<220> FEATURE:
<223> OTHER INFORMATION: Synthetic polynucleotide

<400> SEQUENCE: 30

| | |
|---|---|
| caaaaaggaa gcactgagtg cggctattat gtcatgcact ggatgtccac catcatatta | 60 |
| ggaaatttca ggaataactg ggaagcagta cgtttatttc aaacaaattc gattttttta | 120 |
| taatttgtat tacattatta acttatcatt tatttcatca tgcagtattt taacgatcct | 180 |
| agaccattgg agttagagag attaaagacg cttcggatcc agtgggcata gtattatctc | 240 |
| cgagttagag atcagagcta gctaggattt agggacattg agtttaactt agtttacttt | 300 |
| ggttttacat ttttgtcatt tcctatgtta tttgaacatt aaattcattt gttgataggt | 360 |
| gttaataata aatcaattat tcattgttta ttgtgattaa aactgcttga aagcagaata | 420 |
| aaatgttttat ttactgtgaa ttgggtcaaa aattgtattt tacaggtaca atttgggtt | 480 |
| tattataaag aaagtttata taaaaaaac ttgaaaacaa catcggttat taataaaaac | 540 |
| cgatgttaat atagtaaaca acatcaatta tttagaaaaa tcgatgtcaa catacacctt | 600 |
| aacatcggtt tttcaataaa tcgatgttgg ttatttctaa taacatcggt tatttataca | 660 |
| taaccgatgt taatatacaa acgttaacat cggttattta taaataactg atgttatata | 720 |
| taactaacta caacaaataa gtgtatagat gatggacgtt cacattggtt atatataaaa | 780 |
| aaacgatgtt aatctattgg ttaacatcga ttttatatca aaaccgatgt caacgttcat | 840 |
| catgtataca cttatttgc tatagttctt tatatataac attgcttatt tagaaaaccg | 900 |
| atattaacat ttttatgtta acatcagttt ttaaaaatcg atattaacaa taatacattc | 960 |
| agcatcagta ctttcaacat cggttttaaa atcgatgtag aatgctgtaa ataaccgatg | 1020 |
| ttgaaagtat atttctaat agtgtagagg tattcgagta tttgaccaag ctgagtactt | 1080 |
| gaatacttac tgtgttgaaa gatgcattta agaaataagg caagataggg gagtatctaa | 1140 |
| gtattcggca tgtccaaata tccgaatatt agtggacact tgaagagtt cttgaatgtc | 1200 |
| aaggttgtta gcgtgcaagt attcagcatg actaaatacc caaacattgg tgaaagctttt | 1260 |

```
gaagagttct tgaatgacaa ggttgtcagt gtgcggatat tcgacatggc taaatatttg    1320
aacactgatg gaagttttga agagttcttg aatgtcaagg ttattaatgt gtaggtattc    1380
gacggcatgg tcgaatacgg ggatatgaaa tctaaggagc acttaagtgt tcactcaagc    1440
cgaatgtcta agtatctttt atagaatata cttcaatgtc ctaaagattt tgttagagat    1500
attttaaatg tttgattaga ccaaacactt atctaatata ctttaaaatt acattaaaag    1560
ttatttgatt tgtaacaaaa acatttttaca ttaataatca tactcattaa actcatctta    1620
acatcatttt caacaaattt atccgtacaa aagttaattt tgatcataaa taattatcaa    1680
ttataaataa caattgatga ttgaaataat ctaattttta tatattgcaa taaaatttta    1740
cacgcttaat taattaaaat tataataaat atgattttca agtcattatt ataaaaatgt    1800
agatatcagt ttattaagta aatatttaat gaatctttat aatattatct aattataaat    1860
tatctcagat taaaaaaaat taatcataaa aaataagagt aagctcactt tttttcaaaa    1920
aattaaataa aatagaatcg cattgacgcg aggcagaaat cgcaaaaaat ggtatcacgg    1980
gtcatacgcc ggtcccgtag gtgtcacccg acccacctac ttcacttacc tttacctgtc    2040 attttttcgct cttcttttttt tacccttctt tcaaccttta ttaaaaccct atctcactca    2100
ctctcaccca cacccgtttt gttctattct taactcaact tctgctaccc actctcttct    2160
tccaagtcca accacgcttt tctctacagt c                                    2191

<210> SEQ ID NO 31
<211> LENGTH: 2059
<212> TYPE: DNA
<213> ORGANISM: Artificial Sequence
<220> FEATURE:
<223> OTHER INFORMATION: Synthetic polynucleotide

<400> SEQUENCE: 31
gtcgaacatc aacatcatct cgcagaataa aagatgtgta catataacgt tgtcctgact      60
caaatatagg acatcgaagg tggagatgtt aaatatgttg ttgtggttca atgtttagtt     120
tttggtgaat aagttcaagc aattctgtaa aggttatgac cttgttgatc atgaaagttt     180
ttgtgttgtt actaacgaaa gtgatgtcct cattagtgtt gcagatttgg ccattatagt     240
aaacacaaac atatgcagtt gggtgataca ttgtggtagg gattgagatg aaaatttgaa     300
agtgttacga atatctttag ctgtagtggt atttgtagaa tttacttata gttgagtgag     360
tcactagtta actgtgcatt tagatgagca ggtaaatgaa cacttaagca tatttgcaag     420
agtccatgat gtgcaaattg caaagtgttg ctggtaagca atttaatttt ttagcaacgc     480
ctgcaaattg caaagtgtta tcaatttgga ctgtgattta tccctgataa ttgatggagc     540
aaaagtccat tataatttttc agagtggaga aaaattctga gttatccatc ttatgttagt     600
tttattggtg caacatttat ttttttagag acgtatgtaa attgcatagt gtcacggatt     660
tttttttttt attctttgac gttcaaacca tggaaaaagt gtgtcacgaa tatcattaat     720
gtgttggaca taattttaaa aaaatgcaaa acatgaacac ttaagcataa ttgcaaaggt     780
tcaaatcata atttttttcga tgccttagga accttttgct aggcactgct agttttttttt    840 ttgttgtttt tccttgtgtt tatattctga tgcataaaaa aaaatctcca acttcatatt     900
ttttagaaaa ctaaaaaata ttcttgtaaa aatgtcccct aaaagaattt aataaatatt     960
tgttgtcggt gtaaatgttt gtacatttttg tacttattac aattatcaag aaaaatgaat    1020
gttatacaga tgttggaata ataaataaaa taaataatat aattaggaat ataaataaaa    1080
```

| | | | | |
|---|---|---|---|---|
| atattaatta | tatttcttaa | tttctatata | ataaccttaa | ataacaaaat aaaaagatga | 1140 |
| aagtagccta | aaatgaagaa | aaaatgatta | aaataattta | ccctaacaat agaaacacac | 1200 |
| acccaaaaat | aaaataaaaa | aagagtatgg | ggtccatgtt | ttgtcggctc aagatagtaa | 1260 |
| aaatggatag | tgatttaaaa | tttgtattgg | atagaatata | ttagtgtatg tttgatttga | 1320 |
| ccattttcta | taaaaacaga | aacaatgtta | agaatatgtt | tagttaaaat tttaaaaata | 1380 |
| tttaaaaaaa | cagtgaaaat | tcgaaaacgc | gaaatactca | ttctcatgga aacagaatcg | 1440 |
| gcctttagaa | aacgcaatgg | cataaaatgt | aaatattgtt | attcttcttt tgagttcccc | 1500 |
| tattatcatg | ctgtttgcca | tatttcctca | taactgaaca | ccccttttt taataatctt | 1560 |
| gaaactaaat | catatcttgt | tgccgatcgt | cttcaacgga | atatatacct ttgctttctg | 1620 |
| aaaatctttt | gttgaacaag | ggtgagaata | ttttaatctt | tagatttggt attagtttat | 1680 |
| ttatttattt | ttgtaaataa | ataatacaat | gattctaata | attcttattg aggaaacata | 1740 |
| ttagacaaaa | tttcattgaa | aatcatttat | aaaatttatg | ctaaaattat ttcttgaggt | 1800 |
| tttttttttt | aaaaaaaaaa | tcaagccaac | cacgtttctt | aaactttaaa aattaaaatt | 1860 |
| gaaaattatt | tccccaaaat | aaaaataaaa | ataaaaaata | ttttctcaaa ccaaacaaac | 1920 |
| cttcacgtct | ctttccatac | agtcatttct | gcaagttggg | tttggttttc tcttcttcgt | 1980 |
| tcgtttcgtt | gaaagcgac | ttttctctc | tgcaactctc | ccttttcttc cttcgtagat | 2040 |
| cgaaagggaa | tcttcttcc | | | | 2059 |

<210> SEQ ID NO 32
<211> LENGTH: 2367
<212> TYPE: DNA
<213> ORGANISM: Artificial Sequence
<220> FEATURE:
<223> OTHER INFORMATION: Synthetic polynucleotide

<400> SEQUENCE: 32

| | | | | |
|---|---|---|---|---|
| gacgttcaaa | ccatggaaaa | agtgtgtcac | gaatatcatt | aatgtgttgg acataatttt | 60 |
| aaaaaaatgc | aaaacatgaa | cacttaagca | taattgcaaa | ggttcaaatc ataatttttt | 120 |
| cgatgcctta | ggaacctttt | gctaggcact | gctagttttt | tttttgttgt ttttccttgt | 180 |
| gtttatattc | tgatgcataa | aaaaaaatct | ccaacttcat | atttttaga aaactaaaaa | 240 |
| atattcttgt | aaaaatgtcc | cctaaaagaa | tttaataaat | atttgttgtc ggtgtaaatg | 300 |
| tttgtacatt | ttgtacttat | tacaattatc | aagaaaatg | aatgttatac agatgttgga | 360 |
| ataataaata | aaataaataa | tataattagg | aatataaata | aaaatattaa ttatatttct | 420 |
| taatttctat | ataataaccct | taaataacaa | aataaaaaga | tgaaagtagc ctaaaatgaa | 480 |
| gaaaaaatga | ttaaaataat | ttaccctaac | aatagaaaca | cacacccaaa aataaaataa | 540 |
| aaaaagagta | tggggtccat | gttttgtcgg | ctcaagatag | taaaaatgga tagtgattta | 600 |
| aaatttgtat | tggatagaat | atattagtgt | atgtttgatt | tgaccatttt ctataaaaac | 660 |
| agaaacaatg | ttaagaatat | gtttagttaa | aattttaaaa | atatttaaaa aaacagtgaa | 720 |
| aattcgaaaa | cgcgaaatac | tcattctcat | ggaaacagaa | tcggccttta gaaaacgcaa | 780 |
| tggcataaaa | tgtaaatatt | gttattcttc | ttttgagttc | ccctattatc atgctgtttg | 840 |
| ccatatttcc | tcataactga | acaccccctt | ttttaataat | cttgaaacta atcatatct | 900 |
| tgttgccgat | cgtcttcaac | ggaatatata | cctttgcttt | ctgaaaatct tttgttgaac | 960 |
| aagggtgaga | atattttaat | ctttagatttt | ggtattagtt | tatttattta tttttgtaaa | 1020 |
| taaataatac | aatgattcta | ataattctta | ttgaggaaac | atattagaca aaatttcatt | 1080 |

```
gaaaatcatt tataaaattt atgctaaaat tatttcttga ggttttttt tttaaaaaaa    1140 aaatcaagcc aaccacgttt cttaaacttt aaaaattaaa attgaaaatt attttcccaa    1200
aataaaaata aaaataaaaa atattttctc aaaccaaaca aaccttcacg tctctttcca    1260
tacagtcatt tctgcaagtt gggtttggtt ttctcttctt cgttcgtttc gttgaaaagc    1320
gactttttct ctctgcaact ctccctttc ttccttcgta gatcgaaagg gaatcttctt    1380
ccatggcctc aagcggatt ctgaaggagc ttaaggacct ccagaaagac cctccaacct    1440
cttgcagcgc cggtacaatt ttcttcaccg aattcctttt ctttttaccc ccttttttgct    1500 ctctatctat cccaaaccct tattaagctt catatgttgc tcgatctatg agttttggaa    1560
tttacacgta tgtgggtcgt tgtgtttttt ttccctcctc gtttcctagg tttatttggg    1620
ttttgttata tgtgtttcta gatgccgatt tacgtacgtt aatgtaataa attgacaatc    1680
tttgaagaag catgatgagg tgtttgttct aagcttcata tcccaggttg tgacctcaaa    1740
agattatcgt caatatgatg ttttgtgaga cttttctggt tatccgaaga agcttttctt    1800
ggttaagagt gataaccaac gattcataag tttgttgttt aactttgttt gctattaatt    1860
ggtatcaaat atctttattt ttttaaaatc aattcctctc tgtgttcttt ctactgaagt    1920
tgaaatcctg cattcaaagt gtcgtgactg cttagaaatt agaatctctc tagtctctat    1980
tgccttcttt tatcagagat tttctctaag tctgtgtttt ggattgtga caactatcat    2040 ggattgaaga tagagagact attgtgatta tctctgtctt tggttgtaga atccattgga    2100
agataactct tactttaaga ttgtatatgg ctgacattat tatctttcta gatgtttatt    2160
atgtatctga gttgcatgaa catactcatc aaacaagcag atataactca taagttgtga    2220
gtctgtatat atttgaaaat tttgtttaaa ctgcattctt tagtctgtta cacattattc    2280
attattttcc gataccatat tggaaaccaa tgttaagttt gttattttct aatgattatt    2340
acatttcata ggtcctgtag cggaaga    2367
```

<210> SEQ ID NO 33
<211> LENGTH: 1382
<212> TYPE: DNA
<213> ORGANISM: Artificial Sequence
<220> FEATURE:
<223> OTHER INFORMATION: Synthetic polynucleotide

<400> SEQUENCE: 33

```
gacgttcaaa ccatggaaaa agtgtgtcac gaatatcatt aatgtgttgg acataatttt      60
aaaaaaatgc aaaacatgaa cacttaagca taattgcaaa ggttcaaatc ataatttttt     120
cgatgcctta ggaaccttt gctaggcact gctagttttt ttttgttgt ttttccttgt      180 gtttatattc tgatgcataa aaaaaatct ccaacttcat atttttaga aaactaaaaa       240 atattcttgt aaaaatgtcc cctaaaagaa tttaataaat atttgttgtc ggtgtaaatg     300
tttgtacatt ttgtacttat tacaattatc aagaaaatg aatgttatac agatgttgga     360
ataataaata aaataaataa tataattagg aatataaata aaaatattaa ttatatttct     420
taatttctat ataataaacct taaataacaa aataaaaaga tgaaagtagc ctaaaatgaa    480
gaaaaaatga ttaaaataat ttaccctaac aatagaaaca cacacccaaa aatataaataa    540 aaaaagagta tggggtccat gttttgtcgg ctcaagatag taaaaatgga tagtgattta    600
aaatttgtat tggatagaat atattagtgt atgtttgatt tgaccatttt ctataaaaac    660
agaaacaatg ttaagaatat gtttagttaa aatttaaaaa atatttaaaa aaacagtgaa    720
```

-continued

| | |
|---|---|
| aattcgaaaa cgcgaaatac tcattctcat ggaaacagaa tcggccttta gaaaacgcaa | 780 |
| tggcataaaa tgtaaatatt gttattcttc ttttgagttc ccctattatc atgctgtttg | 840 |
| ccatatttcc tcataactga acaacccctt ttttaataat cttgaaacta atcatatct | 900 |
| tgttgccgat cgtcttcaac ggaatatata cctttgcttt ctgaaaatct tttgttgaac | 960 |
| aagggtgaga atattttaat ctttagattt ggtattagtt tatttattta tttttgtaaa | 1020 |
| taaataatac aatgattcta ataattctta ttgaggaaac atattagaca aaatttcatt | 1080 |
| gaaaatcatt tataaaattt atgctaaaat tatttcttga ggttttttt tttaaaaaaa | 1140 |
| aaatcaagcc aaccacgttt cttaaacttt aaaaattaaa attgaaaatt attttcccaa | 1200 |
| aataaaaata aaaataaaaa atattttctc aaaccaaaca aaccttcacg tctctttcca | 1260 |
| tacagtcatt tctgcaagtt gggtttggtt ttctcttctt cgttcgtttc gttgaaaagc | 1320 |
| gacttttct ctctgcaact ctccctttc ttccttcgta gatcgaaagg gaatcttctt | 1380 |
| cc | 1382 |

<210> SEQ ID NO 34
<211> LENGTH: 2050
<212> TYPE: DNA
<213> ORGANISM: Artificial Sequence
<220> FEATURE:
<223> OTHER INFORMATION: Synthetic polynucleotide

<400> SEQUENCE: 34

| | |
|---|---|
| ttagaaggga acatcaaaga gtccacttca tatgtgaccc tcagaagctc aacattggga | 60 |
| gagtgaatgg tctccctaga ccctgtcatt ttcttagcat cattctctgt tctaaacatg | 120 |
| taaaatccaa catctccacc atcccctcca ataaactgaa cacatggaaa aggctgtttc | 180 |
| ttgccaggcc aatccgaatc tttcccaacc cggacgccaa acaagtgccc cggacgcagc | 240 |
| ctcttccacg gctcagttct atacaaagct gcagaagctt tgtatataga tttaataaaa | 300 |
| tttggagcaa tgccatccac tttcatcatg catgtcccag atccagggcc aagaccagga | 360 |
| ccagacccaa attgctcctg aaatctgtca acaaactct tcaaatgcaa atccattgtc | 420 |
| tccccaattc ctcagattct ttttctttct atgctcgcaa ttcactccag tgaaactaaa | 480 |
| tctgtccgct tcaacacttg aaattatgca ataactctga tctcacaaat tctcacaact | 540 |
| ctactccact tcaacaaccc aaattccgc tatgaagtag cactagactt aacaaagcaa | 600 |
| aatgccaaaa cgcatttggg tacatgagta cagcttatga atcagcacc cactcaactt | 660 |
| tgttcatgca acagaaaaca gataataaaa caaaaactga tcggaccata agatcaattg | 720 |
| tttcaaattt tcaatcagaa agcaaaagaa aaaagttca aagcttttgg ttcgtaccag | 780 |
| cccgcaaaac agtgaccgag ttgtgctcca aagacccaat tccgaaacgt tcattttcg | 840 |
| gacataaatg gaattgacgg gtaaagtcat atcatgcggg cattcgtatt tgtgacctgt | 900 |
| gagctcggaa ttcccatcag gaaattgaag ccattgaagt aatcaacgat cagaaaacga | 960 |
| tttgctaaaa tataatcaac ggtcaaaaac ttattgcaag agttttcttt tcctttatg | 1020 |
| aattgaattt gcaagagttt atttacgaac tatttaaact tattgtacca cagatattca | 1080 |
| tgtaagtatt cgaaaacat gtaaaagaa cttaacattt atatgaaaaa gtttatttct | 1140 |
| aaattttctt tgataataac aatatttca tataaatatt aaacaaatgt ttattcaata | 1200 |
| agtttttta attaatatca ctaaatttaa aattgattaa actgagtata aaaaatataa | 1260 |
| attttgttta tttagaaagg ggttttatat ttagttttaa aattaattta aactaagcta | 1320 |
| attcaaagtc gatttataaa atatatgaac tataattata attttaaagt tgatatcact | 1380 |

```
ttcaaattaa gatatatgtc ttatcctaat taaatgtact aaatctttaa tttagttttt      1440
ttttcaaata tatcttttaa tttgatttta aatttaattt aattatcatc taaacatttt      1500
ttaaaattat tttagacaac tctcattgta tcattatctg tatatttagt ttttttttaa      1560
ctgcgtatct ttattttttaa attaagtttt ttatctgtgt attagaaagc tgtctttttt     1620
acacaaaata aaaaaaaaat caaattaact ttcaattttc tttgacagca atcaaatcaa      1680
ataattattc gcccaaaaaa aatgaagctc gaaatacata ggtttaagtg aaggaagaag      1740
aggacgtcaa tctctgacac gagtacagag aacatgcgtc gtttgcagca gcagccaatg     1800
agaatccccc acctaatcac ccaaacgata aaaatccaat caatcttta attaataaaa      1860 aataaaaaat aaaaaaataaa aaaccatagt gcccatcacg cacgcacctt acttaccta    1920 ccaataccat cccctttta gggttagggt tgtgagtctt cctttaaagg ggcatcgaga      1980
ctcaatctct ttctctctct ttctttgccc tctctttctc tctctagaat tctcagattt     2040
gcggggcgag                                                             2050
```

<210> SEQ ID NO 35
<211> LENGTH: 2391
<212> TYPE: DNA
<213> ORGANISM: Artificial Sequence
<220> FEATURE:
<223> OTHER INFORMATION: Synthetic polynucleotide

<400> SEQUENCE: 35

```
aagcttttgg ttcgtaccag cccgcaaaac agtgaccgag ttgtgctcca aagacccaat       60
tccgaaacgt ttcattttcg gacataaatg gaattgacgg gtaaagtcat atcatgcggg      120
cattcgtatt tgtgacctgt gagctcggaa ttcccatcag gaaattgaag ccattgaagt      180
aatcaacgat cagaaaacga tttgctaaaa tataatcaac ggtcaaaaac ttattgcaag      240
agttttcttt tccttttatg aattgaattt gcaagagttt atttacgaac tatttaaact      300
tattgtacca cagatattca tgtaagtatt cgaaaaacat gtaaaagaa cttaacatttt       360 atatgaaaaa gtttatttct aaattttctt tgataataac aatatttca tataaatatt       420 aaacaaatgt ttattcaata agttttttta attaatatca ctaaatttaa aattgattaa      480
actgagtata aaaatataaa attttgttta tttagaaagg ggttttatat ttagtttaa      540 aattaattta aactaagcta attcaaagtc gatttataaa atatatgaac tataattata    600 atttaaagt tgatatcact ttcaaattaa gatatatgtc ttatcctaat taaatgtact      660
aaatctttaa tttagttttt ttttcaaata tatcttttaa tttgattta aatttaattt      720 aattatcatc taaacatttt ttaaaattat tttagacaac tctcattgta tcattatctg     780
tatatttagt ttttttttaa ctgcgtatct ttattttttaa attaagtttt ttatctgtgt    840
attagaaagc tgtctttttt acacaaaata aaaaaaaaat caaattaact ttcaattttc     900
tttgacagca atcaaatcaa ataattattc gcccaaaaaa aatgaagctc gaaatacata     960
ggtttaagtg aaggaagaag aggacgtcaa tctctgacac gagtacagag aacatgcgtc    1020
gtttgcagca gcagccaatg agaatccccc acctaatcac ccaaacgata aaaatccaat    1080
caatctttta attaataaaa aataaaaaat aaaaaaataaa aaaccatagt gcccatcacg   1140
cacgcacctt acttaccta ccaataccat cccctttta gggttagggt tgtgagtctt      1200
cctttaaagg ggcatcgaga ctcaatctct ttctctctct ttctttgccc tctctttctc    1260
tctctagaat tctcagattt gcggggcgag atgatgcagc agccaggacc cggcatggca    1320
```

-continued

```
cctcccacca tgggccagca gccgccgcaa cagtaccagc agcctccgcc gcagcagcag    1380
caaccctacg tcatgatgcc gccgcaggcc caggccccgc aggccatgtg gccccctcc     1440 gcccagcctc cgcctcagca gcagcccgcc agcgccgacg aggtccgaac cctctggatc    1500
ggggatctgc agtactggat ggacgagaac tatctctata cctgctttgc tcacaccggc    1560
gaggtataat aataattagt atcccttctc tttcctttat ttcaagttga tttgttttca    1620
ttagcctatt gaatagacct tttgttttct acgtgaattt tgatcacttt taggtttttt    1680
ttttaaatgt ttgtgctttt agtttgaata gggatttctg ctgtgttaat cgtggtttga    1740
atttggtatt gatttagacg tgcggctgtt ctgtcgttgt gatactgaag tgtcagtttt    1800
tggtggattg aaggtttaat ttttgtattg aattttggtg gtttgtattg ttagctgttt    1860
ttggctaaat tggttagggt tttctgcagc atgaaattag aacctttcta gattttgttt    1920
taaatgcccg tacttgttga tttatgctta ggtgtaagag tgttctgtta tgatactgag    1980
gtgtgggttt tgtagcattt taggttggat tttgtattca ttctttattt gtgttcgaca    2040
aagtcgaaga tggttctttg tccgttctag ttttgtattg agttagatgt tctgttgtga    2100
taataaatgt gttcgacaaa gttgaatctg gttttcggta tgtctgtttt aggttttta    2160 aacacgtgca attgttagtt tgaattgtgt attgagttag acgcatgaat gctcggttgt    2220
ggtaataaat gtgttctaca aaggtgaata tggttttctg tttgtctgtt ctatgttttt    2280
ttaaacatat gtacttgtta gtttaaaact tgtattgagc tagacatgca aatgttctgt    2340
cgtgatacta aatgtttgtt ctgttttatt gtaggttaca tcggttaaag t             2391
```

<210> SEQ ID NO 36
<211> LENGTH: 1284
<212> TYPE: DNA
<213> ORGANISM: Artificial Sequence
<220> FEATURE:
<223> OTHER INFORMATION: Synthetic polynucleotide

<400> SEQUENCE: 36

```
ttggttcgta ccagcccgca aaacagtgac cgagttgtgc tccaaagacc caattccgaa      60
acgtttcatt ttcggacata aatggaattg acgggtaaag tcatatcatg cgggcattcg     120
tatttgtgac ctgtgagctc ggaattccca tcaggaaatt gaagccattg aagtaatcaa     180
cgatcagaaa acgatttgct aaaatataat caacggtcaa aaacttattg caagagtttt     240
cttttccttt tatgaattga atttgcaaga gtttatttac gaactatttg aacttattgt     300
accacagata ttcatgtaag tattcgaaaa acatgtaaaa agaacttaac atttatatga     360
aaaagtttat ttctaaattt tctttgataa taacaatatt ttcatataaa tattaaacaa     420
atgtttattc aataagtttt tttaattaat atcactaaat ttaaaattga ttaaactgag     480
tataaaaaat ataaatttg tttatttaga aaggggtttt atatttagtt ttaaaattaa      540
tttaaactaa gctaattcaa agtcgattta taaaatatat gaactataat tataattta      600 aagttgatat cactttcaaa ttaagatata tgtcttatcc taattaaatg tactaaatct     660
ttaatttagt ttttttttca aatatatctt ttaatttgat tttaaattta atttaattat     720
catctaaaca ttttttaaaa ttattttaga caactctcat tgtatcatta tctgtatatt     780
tagttttttt ttaactgcgt atctttattt ttaaattaag ttttttatct gtgtattaga     840
aagctgtctt ttttacacaa aataaaaaaa aaatcaaatt aactttcaat tttctttgac     900
agcaatcaaa tcaaataatt attcgcccaa aaaaaatgaa gctcgaaata cataggttta     960
agtgaaggaa gaagaggacg tcaatctctg acacgagtac agagaacatg cgtcgtttgc    1020
```

```
agcagcagcc aatgagaatc ccccacctaa tcacccaaac gataaaaatc caatcaatct    1080
tttaattaat aaaaaataaa aaataaaaaa taaaaaacca tagtgcccat cacgcacgca    1140
ccttacttac cttaccaata ccatcccctt tttagggtta gggttgtgag tcttccttta    1200
aaggggcatc gagactcaat ctctttctct ctctttcttt gccctctctt tctctctcta    1260
gaattctcag atttgcgggg cgag                                           1284
```

<210> SEQ ID NO 37
<211> LENGTH: 2236
<212> TYPE: DNA
<213> ORGANISM: Artificial Sequence
<220> FEATURE:
<223> OTHER INFORMATION: Synthetic polynucleotide

<400> SEQUENCE: 37

```
aataataggc ttctctgttt aggcgaaaat ttatcatctt ttcttgttta ttgttttgag      60 tttaatttt atatattgtt aatataaata gttttacatg gttgattagc tataaattct     120
aaatgtgact ttttaaaata attattcaaa aatttaatat ttttaccata aattattaat    180 atttttttg ctagtgatat gccagttaat ataaatatag ttttatattt tttattaatt    240
agaaattcta aatgcgacgc ccttattgta gaaatatgaa tattctctgc ttttatagta    300
tgtgcatgta tgacacaact cttcaaatgg gaaattgag ttaaaatatt gttaggattt    360
tttataaaca aaggatttta ttaataataa aaatgcttaa attgaacatg aatacataag    420
agtccaaaca cagcattgtt tcaatcaaaa gcccaaggaa ttgaagaaag ccaattacaa    480
gccattaaag ccacatgaca attaaccccc aaacacgttg taatcccatg gaagctttca    540
atgataaaaa agaaatacgt acatgatcca cctttacgta gcatacattt gctttcaaag    600
ttgttcatgt ttcatgataa gttcatgtag gaacatgccc tgcttttaat caaataagca    660
tgactgacat caaaatgagg attgattgat tgtcgtcaat aacattgtta ggaactgtca    720
tgtcctcaca ttaatgaatt ctctattttt attttttttt aatttagtag cacgtaagat    780 tataaagtc acaaaaaact caagtgttat tattaggaga gtaaaaaatg atatacaaat    840
atcataaaaa taactaatta aaaaataatt actattatgt aaaatcatta aaaaaataaa    900
attactcgta agagatatat tacaaaaaat tattaattta acttatacag tatgaactta    960
attatgttca cctttattga tgaagtttat tcactgttat tgtcatttgt gtgataagag   1020
ggaagaagaa gagatgaatc aagttgagtc agaggcagca gatgaaacca ttcaagggt    1080 agtaacagac acaacacagg tgcaagaaga agcagagaaa accaaagag tagtgaggaa    1140 gcccacttac ttcaaggact ttgtctaaag ggtgaagtgt gtatttccat aacaaaatca    1200
tcaacaaaca aattctgtta ctaggattac tataaataca attgtaataa caagcaaag    1260 atatgaatga atgaaatttc catatttctt acttttcttc tttggagggt tctggtcctc    1320
gaaaccaaat tcttagttct cttaccaatt tgtctctttt tggttggtta ttcagtgtaa    1380
caaaataaaa aaaataagaa ttatgaatct aaataatggt atacatgaca aagagatata    1440
gctcacattg acaactaaaa attgaattac tgatcacttg cattttcatt tatcttttac    1500
accagcgaca accaaattga tcatacaaca tttgaaccaa cttttcatgt ttaattttct    1560
atgtgtaacc atatactgca tagaggacca tacatgtacc ttttgcatgg tgcatacacc    1620
tctaacttat attgtgaaaa caagtttagt ttctatttgc tagtgttgtt acacaatcaa    1680
atttgttctt atcattcttt ttttttgtgt gaaagttaca ttcttaaata agtattatgg    1740
```

```
aataagcttt catattactt aactttattt cttactcgtt atttcaaaag gtgaaaatta   1800
catttctacc cagacacaca ctaaatacag tacaaactcg aagcaaatga tttggattga   1860
tttaaatcaa ttttaggttc acaagggcaa ggggtggaat ataagaaga aagaaatgga    1920 taagggtgtc atttggtgtg gcatatatc caaccaaaaa gggacatttt gcgggtattt    1980
gtgagtgtgt gagagagaga gcgagcagtt tcagacacag agagaggggt ttgggattgg   2040
agggattgac gctgcgtctc ttcctcttct ctttcgatcc atccctcatt cctaatcctc   2100
caatccaacc acctcagcct cacactcaca tatacacatg tctctctcta tttcccttt    2160 cactttcact ttcatttcta gggttccgtt ctgatggctc tttcccttc agatctgaac    2220 gcgtatcgtc cctcct                                                   2236
```

<210> SEQ ID NO 38
<211> LENGTH: 2102
<212> TYPE: DNA
<213> ORGANISM: Artificial Sequence
<220> FEATURE:
<223> OTHER INFORMATION: Synthetic polynucleotide

<400> SEQUENCE: 38

```
aactgtcatg tcctcacatt aatgaattct ctattttat ttttttta tttagtagca      60 cgtaagatta taaagtcac aaaaaactca agtgttatta ttaggagagt aaaaaatgat    120
atacaaatat cataaaaata actaattaaa aaataattac tattatgtaa aatcattaaa   180
aaaataaaat tactcgtaag agatatatta caaaaaatta ttaatttaac ttatacagta   240
tgaacttaat tatgttcacc tttattgatg aagtttattc actgttattg tcatttgtgt   300
gataagaggg aagaagaaga gatgaatcaa gttgagtcag aggcagcaga tgaaaccatt   360
caaggggtag taacagacac aacacaggtg caagaagaag cagagaaaac caaagagta    420 gtgaggaagc ccacttactt caaggacttt gtctaaaggg tgaagtgtgt atttccataa   480
caaaatcatc aacaaacaaa ttctgttact aggattacta taaatacaat tgtaataaac   540
aagcaaagat atgaatgaat gaaatttcca tatttcttac ttttcttctt tggagggttc   600
tggtcctcga aaccaaattc ttagttctct taccaatttg tctcttttg gttggttatt    660 cagtgtaaca aaataaaaaa aataagaatt atgaatctaa ataatggtat acatgacaaa   720
gagatatagc tcacattgac aactaaaaat tgaattactg atcacttgca ttttcattta   780
tcttttacac cagcgacaac caaattgatc atacaacatt tgaaccaact tttcatgttt   840
aattttctat gtgtaaccat atactgcata gaggaccata catgtacctt ttgcatggtg   900
catacacctc taacttatat tgtgaaaaca agtttagttt ctatttgcta gtgttgttac   960
acaatcaaat ttgttcttat cattctttt ttttgtgtga agttacatt cttaaataag    1020 tattatggaa taagctttca tattacttaa ctttatttct tactcgttat ttcaaaaggt   1080
gaaaattaca tttctaccca gacacacact aaatacagta caaactcgaa gcaaatgatt   1140
tggattgatt taaatcaatt ttaggttcac aagggcaagg ggtggaatat aagaagaaa    1200 gaaatggata agggtgtcat ttggtgtggg catatatcca accaaaaagg gacattttgc   1260
gggtatttgt gagtgtgtga gagagagagc gagcagtttc agacacagag agagggttt    1320 gggattggag ggattgacgc tgcgtctctt cctcttctct ttcgatccat ccctcattcc   1380
taatcctcca atccaaccac ctcagcctca cactcacata tacacatgtc tctctctatt   1440
tcccttttca ctttcacttt catttctagg gttccgttct gatggctctt tcccttcag    1500 atctgaacgc gtatcgtccc tcctatggct tcaaagcgca tcctcaagga gctcaaggac   1560
```

| | |
|---|---|
| ttgcagaaag acccaccaac ttcttgcagc gctggtaccc cttttcttct ccattccact | 1620 |
| cccccaccac gattttttg tccgcactat ttgggatgtg ataaaaatct atttttttcc | 1680 |
| tgggtttctg tttgttctag ggttaaatga ataaattta ataagcgca aattaggctg | 1740 |
| tttctgccac attttgtaag ctatgtacgt gtgattctat gtgtgcactc ttactaacct | 1800 |
| tgctggggta aaataaaatt atacaagttc atgagaaaat aaatcatagg aaatatgata | 1860 |
| actgtctgta caaggtttta aattgtggtc ccgttgtgtt ccttgatgtc gcaggaaatt | 1920 |
| gtgtttaagt agatgttgca accgaaataa tggttgcgga cctttttaa aaccttgtgt | 1980 |
| gtgtttatgt tgtgagtttg agccatacat gtttatgtt gtgagtttga accatacatg | 2040 |
| ttttgtttgt ttgtagtatg tgcaaataca aatgtttatt ttgtaggtcc agtagctgag | 2100 |
| ga | 2102 |

<210> SEQ ID NO 39
<211> LENGTH: 1526
<212> TYPE: DNA
<213> ORGANISM: Artificial Sequence
<220> FEATURE:
<223> OTHER INFORMATION: Synthetic polynucleotide

<400> SEQUENCE: 39

| | |
|---|---|
| ggaactgtca tgtcctcaca ttaatgaatt ctctattttt attttttttt aatttagtag | 60 |
| cacgtaagat tataaaagtc acaaaaaact caagtgttat tattaggaga gtaaaaaatg | 120 |
| atatacaaat atcataaaaa taactaatta aaaataatt actattatgt aaaatcatta | 180 |
| aaaaaataaa attactcgta agagatatat tacaaaaaat tattaattta acttatacag | 240 |
| tatgaactta attatgttca cctttattga tgaagtttat tcactgttat tgtcatttgt | 300 |
| gtgataagag ggaagaagaa gagatgaatc aagttgagtc agaggcagca gatgaaacca | 360 |
| ttcaaggggt agtaacagac acaacacagg tgcaagaaga agcagagaaa accaaaagag | 420 |
| tagtgaggaa gcccacttac ttcaaggact ttgtctaaag ggtgaagtgt gtatttccat | 480 |
| aacaaaatca tcaacaaaca aattctgtta ctaggattac tataaataca attgtaataa | 540 |
| acaagcaaag atatgaatga atgaaatttc catatttctt acttttcttc tttggagggt | 600 |
| tctggtcctc gaaaccaaat tcttagttct cttaccaatt tgtctctttt tggttggtta | 660 |
| ttcagtgtaa caaaataaaa aaaataagaa ttatgaatct aaataatggt atacatgaca | 720 |
| aagagatata gctcacattg acaactaaaa attgaattac tgatcacttg cattttcatt | 780 |
| tatcttttac accagcgaca accaaattga tcatacaaca tttgaaccaa cttttcatgt | 840 |
| ttaattttct atgtgtaacc atatactgca tagaggacca tacatgtacc ttttgcatgg | 900 |
| tgcatacacc tctaacttat attgtgaaaa caagtttagt ttctatttgc tagtgttgtt | 960 |
| acacaatcaa atttgttctt atcattcttt ttttttgtgt gaaagttaca ttcttaaata | 1020 |
| agtattatgg aataagcttt catattactt aactttattt cttactcgtt atttcaaaag | 1080 |
| gtgaaaatta catttctacc cagacacaca ctaaatacag tacaaactcg aagcaaatga | 1140 |
| tttggattga tttaaatcaa ttttaggttc acaagggcaa ggggtggaat ataagaaga | 1200 |
| aagaaatgga taagggtgtc atttggtgtg ggcatatatc caaccaaaaa gggacatttt | 1260 |
| gcgggtattt gtgagtgtgt gagagagaga gcgagcagtt tcagacacag agagggggt | 1320 |
| ttgggattgg agggattgac gctgcgtctc ttcctcttct ctttcgatcc atccctcatt | 1380 |
| cctaatcctc caatccaacc acctcagcct cacactcaca tatacacatg tctctctcta | 1440 |

```
tttcccttttt cactttcact ttcatttcta gggttccgtt ctgatggctc tttccctttc    1500
agatctgaac gcgtatcgtc cctcct                                          1526
```

<210> SEQ ID NO 40
<211> LENGTH: 1522
<212> TYPE: DNA
<213> ORGANISM: Artificial Sequence
<220> FEATURE:
<223> OTHER INFORMATION: Synthetic polynucleotide

<400> SEQUENCE: 40

```
tggaattctg tggtatccgt ttatcagtta gttcaggtgc acacaaatgc gacaattagt      60
tggtaaaact gcaagagatt ttgcaaatat catacaaata ataacaataa atagtttgtc     120
gttttcatgc tgctggtttg atcttcgcag ttcacactga tcaaactaaa caacggtgtt     180
tggtaatatt caaccttctc tctttcaaac cttactacta acctcgtgcg ttgggtaaca     240
ttaggcttcc aacttatctg ttttctttgc cataacttgt tgccaaagag tgtttgttca     300
taataagtgt tggagatata agagtgttgg aaaagtttat ttgccataac ttgttgccat     360
aaagagttga agtaacctct tgataggaaa atggctcaag acaagctgtg aatagaagtc     420
agaaaacaag caaatgaagt agagtaagtg gaataaacaa agtccaatag tttagtgaac     480
ttataatcat gttgagaatg agaaggatcc accctcacaa aaaggttat tgcctaatta     540 atagtaggga ttgaagaagt atcaataatc aataagaggg acatttggat tgacacaaac     600
tattagtata aaaaaaaaat gtaaaactaa atggacaaca atctaagaaa gcgagtatgt     660
gttgtactcg gaaaacataa cataatgtga ttttgattgt ggaaactgaa aacaataaca     720
tttaagtttt atttatctct ttgcctaaca atttttttaa ttactttttt tatagttttt     780
atgatgaaga taattaatat ttttacaaa tattatattt ccttttac catctttgaa      840 gataattgct ttttttttcca atttagacaa atatttgagt atcaatgata ttcctttta      900 atccattatt gcaatttaaa agaccatcaa tgattacatt ttcaatcaaa tgactttatt     960
agtcttcact ttacatcgat ttaaatcaaa ctaataattt tgtatggact aaatctctga    1020
acatttttat atttacaaca tattttaaca tttattaaat aattagtatt taatactatt    1080
agtagaataa tgggagtagc aggagggagg cactgagaga atagagatgg catggaagta    1140
agcaatcaag tcaaaatcag agttggccaa ccccaaaggc tgtagtaggt aagcatggcc    1200
cattttagtt tttacattca tctctcattt tcacctcaac ggttcagatt caatctgact    1260
ccccgatctc agccgtggat tcaaatgcca cctcaggcac atgcaattcc aaatggatga    1320
acctaaccca caatctaatc ttgttactta ggggcttttc cgtcattaaa tgacaccacc    1380
tacccccttc tccctataaa tggcaactca atgcccccct tagaactcgc agcgcttgat    1440
ttgaggccag gcaagcccca ctcaaccacc acacctctcc tcgttcacgc tacccctttc    1500
tgctcttctt ctacctttca ag                                             1522
```

<210> SEQ ID NO 41
<211> LENGTH: 1015
<212> TYPE: DNA
<213> ORGANISM: Artificial Sequence
<220> FEATURE:
<223> OTHER INFORMATION: Synthetic polynucleotide

<400> SEQUENCE: 41

```
tccaccctca caaaaaaggt tattgcctaa ttaatagtag ggattgaaga agtatcaata      60
atcaataaga gggacatttg gattgacaca aactattagt ataaaaaaaa aatgtaaaac     120
```

```
taaatggaca acaatctaag aaagcgagta tgtgttgtac tcggaaaaca taacataatg      180
tgattttgat tgtggaaact gaaaacaata acatttaagt tttatttatc tctttgccta      240 acaattttt  taattacttt tttatagtt  tttatgatga agataattaa tattttttac      300
aaatattata ttttccttt  taccatcttt gaagataatt gctttttttt ccaatttaga      360
caaatatttg agtatcaatg atattccttt ttaatccatt attgcaattt aaaagaccat      420
caatgattac attttcaatc aaatgacttt attagtcttc actttacatc gatttaaatc      480
aaactaataa ttttgtatgg actaaatctc tgaacatttt tatatttaca acatattta      540 acatttatta aataattagt atttaatact attagtagaa aatgggagt  agcaggaggg      600 aggcactgag agaatagaga tggcatggaa gtaagcaatc aagtcaaaat cagagttggc      660
caaccccaaa ggctgtagta ggtaagcatg gcccattta  gttttacat  tcatctctca      720 ttttcacctc aacggttcag attcaatctg actccccgat ctcagccgtg gattcaaatg      780
ccacctcagg cacatgcaat tccaaatgga tgaacctaac ccacaatcta atcttgttac      840
ttagggcttt ttccgtcatt aaatgacacc acctaccccc ttctccctat aaatggcaac      900
tcaatgcccc ccttagaact cgcagcgctt gatttgaggc caggcaagcc ccactcaacc      960
accacacctc tcctcgttca cgctaccct  ttctgctctt cttctacctt tcaag          1015

<210> SEQ ID NO 42
<211> LENGTH: 1829
<212> TYPE: DNA
<213> ORGANISM: Artificial Sequence
<220> FEATURE:
<223> OTHER INFORMATION: Synthetic polynucleotide

<400> SEQUENCE: 42
gcttgacttg atcattgtct catccacgag atagaaacaa aatatataaa agggctcatt       60
atgcttattt agttcatcaa gaagctagga aaatgagtac gtagaatgaa catttaataa      120
tggacgtgag agaagttaat cgctgacagc catgtgccga ccatgttttt tataaatgaa      180
aagaaagaaa tgttcgtata taataattaa cggacacaag aaccttgtta ataattatca      240
ttatcttttt ttttttgttt ttattttccg aaaaacttgt ttctccaatc attgatgtgt      300
atttctattc tctctccatt tccaactcct gactgagaag tggatttcat atcaacatta      360
gcaattagta gaatactatc atctttcacg ctacaaaaca ttggtacttt ggtaggtaaa      420
gatttgcaaa cacgaataag taattaagaa aggttcatac acattcaatg attctggatt      480
cctaccttac gttatttgtt tcgaaatacc tagatgagag catcttgtta tttattacta      540
catattaatt ttccctgtgt accttgtcgt agtttaaatt tattatttt  tcaatcataa      600 ataaatataa gaaatatttt ttccttaata taattttatt ttatatttaa aaataaatca      660
taatttgaaa gagctacaaa tttataccac atgtgggaag tattgttggt ttctccaacc      720
atacttattg agaataactt gaatttatat tcaacgtatt aattgcttca cctttaacgt      780
gccaaaataa taataataaa aaacttaaaa ctactgtatt aatcgcgtgt ggttgaatgg      840
aggcaaattc tattctaaaa aagaaaagca ttaacaaaag gagaaaagaa aaactgttga      900
cacctgacag cagtaacagg gaactgggaa gtagcagtag gagtatttgc gtgttggttt      960
ccaactctgg aatccaccgt gccaaactgc gaatgcagga gaaatcgaca cgtgtccatt     1020
tgcaggcgcg agttgaacgt gacaatgcac caccgcccag catcgaacgc agccaaggac     1080
cacgtcgaaa ccacagtaat ccacgttcca gtgctgcgcg gaacatggtc ggtctttcta     1140
```

| | |
|---|---|
| ggagtggttg gaatcacgcc agctaggaca aaccccatca atcattggtc attatcaaac | 1200 |
| aaaacatttc aaaaattcaa catattacgc ctcgggaccc acctcccact acacctcacc | 1260 |
| ctcacttcta ttaactcgaa cacattcggg ttataaatcc gcaaccctcc ttctcactca | 1320 |
| ctcactcact cactcactca ctcgcaagca aaagaaaga atcccaggcg aggagaaaga | 1380 |
| tggaggggaa ggagcaggat gtgtcgttgg gagcgaacaa gttccccgag agacagccaa | 1440 |
| ttgggacggc ggcgcagagc caagacgacg gcaaggacta ccaggagccg gcgccggcgc | 1500 |
| cgctggttga cccgacggag tttacgtcat ggtcgtttta cagagcaggg atagcagagt | 1560 |
| ttgtggccac ttttctgttt ctctacatca ctgtcttaac cgttatggga gtcgccgggg | 1620 |
| ctaagtctaa gtgtagtacc gttgggattc aaggaatcgc ttgggccttc ggtggcatga | 1680 |
| tcttcgccct cgttactgc accgctggca tctcaggtcc gcttttttt tctttctttt | 1740 |
| cttaatttct caaaagctag aaaaaaaaaa ttaatgtaaa gttgaacaac gttgtttgtt | 1800 |
| tgtatgtgta gggggacaca taaacccgg | 1829 |

<210> SEQ ID NO 43
<211> LENGTH: 2447
<212> TYPE: DNA
<213> ORGANISM: Artificial Sequence
<220> FEATURE:
<223> OTHER INFORMATION: Synthetic polynucleotide

<400> SEQUENCE: 43

| | |
|---|---|
| tctatcgtgt ccaaataaaa tttctaaaaa aacaattaat gagacataga aaaccaaact | 60 |
| tgtatgggga agtgaactag ctgttaaaac aatgagtgga ctcgtgatcc ctcactcaaa | 120 |
| cagaaagcat aatgcgaatt gctaaaaggg gtccagaact gccttggcta tttttttacgt | 180 |
| gtgtttctta attaggagcc acgagacaaa gatataaagg ttagtgtagg accctgccac | 240 |
| ccaaaatctg cctggatatt atgcatgcgt ccctaacctt gttgcttgtg gcttttgcca | 300 |
| gagtagaatg acgaagaaaa ttttcaaaag attcctaatg tttttggctc acaactcaaa | 360 |
| aactcaaact gatcaagaac cgttcatttt attaacgtta tccttacaag tcactcaggc | 420 |
| taatcgagct ggtactaaac taatgcatat taggtaatgc aaataaataa taacgctccc | 480 |
| aagaatattc aaatggtttc ttttgctttt tgcttaacga cttttgtatc tctacgtatt | 540 |
| acttgagaaa aaaagctgct attattatcc aactaaacaa atgaaagcta cagttaagga | 600 |
| catggcctat taacaatatt acgtagactt gatcattgtc tcatccacga gatagaaaca | 660 |
| aaatatataa aagggctcat tatgcttatt tagttcatca agaagctagg aaaatgagta | 720 |
| cgtagaatga acatttaata atggacgtga gagaagttaa tcgctgacag ccatgtgccg | 780 |
| accatgtttt ttataaatga aaagaaagaa atgttcgtat ataataatta acggacacaa | 840 |
| gaaccttgtt aataattatc attatctttt ttttttttgtt tttattttcc gaaaaacttg | 900 |
| tttctccaat cattgatgtg tatttctatt ctctctccat ttccaactcc tgactgagaa | 960 |
| gtggatttca tatcaacatt agcaattagt agaatactat catctttcac gctacaaaac | 1020 |
| attggtactt tggtaggtaa agatttgcaa acacgaataa gtaattaaga aaggttcata | 1080 |
| cacattcaat gattctggat tcctacctta cgttatttgt ttcgaaatac ctagatgaga | 1140 |
| gcatcttgtt atttattact acatattaat tttccctgtg taccttgtcg tagtttaaat | 1200 |
| ttattatttt ttcaatcata aataaatata agaatatttt ttttcttaat ataatttat | 1260 |
| tttatattta aaaataaatc ataatttgaa agagctacaa atttataccca catgtgggaa | 1320 |
| gtattgttgg tttctccaac catacttatt gagaataact tgaatttata ttcaacgtat | 1380 |

| | | | | |
|---|---|---|---|---|
| taattgcttc | accctttaacg | tgccaaaata | ataataataa | aaaacttaaa | actactgtat | 1440 |
| taatcgcgtg | tggttgaatg | gaggcaaatt | ctattctaaa | aagaaaagc | attaacaaaa | 1500 |
| ggagaaaaga | aaaactgttg | acacctgaca | gcagtaacag | ggaactggga | agtagcagta | 1560 |
| ggagtatttg | cgtgttggtt | tccaactctg | gaatccaccg | tgccaaactg | cgaatgcagg | 1620 |
| agaaatcgac | acgtgtccat | ttgcaggcgc | gagttgaacg | tgacaatgca | ccaccgccca | 1680 |
| gcatcgaacg | cagccaagga | ccacgtcgaa | accacagtaa | tccacgttcc | agtgctgcgc | 1740 |
| ggaacatggt | cggtctttct | aggagtggtt | ggaatcacgc | cagctaggac | aaaccccatc | 1800 |
| aatcattggt | cattatcaaa | caaaacattt | caaaaattca | acatattacg | cctcgggacc | 1860 |
| cacctcccac | tacacctcac | cctcacttct | attaactcga | acacattcgg | gttataaatc | 1920 |
| cgcaaccctc | cttctcactc | actcactcac | tcactcactc | actcgcaagc | aaaaagaaag | 1980 |
| aatcccaggc | gaggagaaag | ctggagggga | aggagcaggc | tgtgtcgttg | ggagcgaaca | 2040 |
| agttccccga | gagacagcca | attgggacgg | cggcgcagag | ccaagacgac | ggcaaggact | 2100 |
| accaggagcc | ggcgccggcg | ccgctggttg | acccgacgga | gtttacgtcc | tggtcgtttt | 2160 |
| acagagcagg | gatagcagag | tttgtggcca | cttttctgtt | tctctacatc | actgtcttaa | 2220 |
| ccgttctggg | agtcgccggg | gctaagtcta | agtgtagtac | cgttgggatt | caaggaatcg | 2280 |
| cttgggcctt | cggtggcctg | atcttcgccc | tcgtttactg | caccgctagc | atctaaggtc | 2340 |
| cgcttttttt | ttctttcttt | tcttaatttc | tcaaaagcta | gaaaaaaaaa | attaatgtaa | 2400 |
| agttgaacaa | cgttgtttgt | ttgtatgtgt | aggggacac | ataaacc | | 2447 |

<210> SEQ ID NO 44
<211> LENGTH: 2988
<212> TYPE: DNA
<213> ORGANISM: Artificial Sequence
<220> FEATURE:
<223> OTHER INFORMATION: Synthetic polynucleotide

<400> SEQUENCE: 44

| | | | | | | |
|---|---|---|---|---|---|---|
| aagggcaccg | ctcgttgttg | atgagaacac | gaaatctcct | ctccacaatg | caacgtcaag | 60 |
| atgtcataga | caggtatgga | aaggaaaaat | aaataaataa | ataaatggat | tttatgctcc | 120 |
| acccagtttg | cccttcctga | atgctaacaa | aactcaacat | gttttttgaat | agggtaataa | 180 |
| tcggggttgg | ttttttgttg | ttctcccttg | ctgttcttta | tgttgtttcc | aagcgaattg | 240 |
| gactacttac | gttgcaaaga | aaggttactg | aggccataaa | agctggtatg | gtgggacagg | 300 |
| cagagctaag | gccccaagct | gttgcagatg | acgtgaatct | tcatcaagtc | agaggcaatc | 360 |
| gtgttcctaa | taatgcagag | gctccttttag | aacaaagaat | ccatgatgaa | ctatgatgca | 420 |
| tttctaagca | atactatcat | gttatgtgtg | tttataacac | aactcttcta | attcctttaa | 480 |
| aagtaacgaa | agtaaaaagt | attttgctat | cttgagagtt | cgaaaagcat | ttaatactac | 540 |
| cttttttgaga | attattggct | gatctgttat | aatgaattaa | aaattctttc | tgtagttgtt | 600 |
| tttgtctacg | ctacaggcct | ttcaacatga | gcaagctaat | aattgttgac | gagctgtctc | 660 |
| tggctgcttt | ttcattgtac | caatgcttgt | ctcctacaca | tcaactgtat | ttaagatctg | 720 |
| aagctgacat | gagattttac | aaagcattat | ataattacat | tggcgccaca | ataatttcga | 780 |
| gatatttatc | aaaataaata | aagttgcaaa | tgcaaatgga | gttcacatgc | aatgaatccc | 840 |
| ttgtcataaa | ctccaaaatc | atgattgcaa | cataaacaaa | tgttttagaa | aaattaaaat | 900 |
| ctgtggctta | cgccctcatg | cacatgtttt | gcgtgatgat | taacagttgt | tacagctccc | 960 |

```
tctttctgag tcgtggtaat ttgaggtaaa tttgcgtgat gaactagtaa gttttatttt    1020
ccagtgaagc aactgctaca ggcttgggtg ttggagaaat ttaccattga gttatgcaat    1080
agttacctgg attatcctta cttttttataa tagaaaaata atccttttaa taaactcgtt   1140
tagattctgt ttatacaaat ttggtagatt aaacaaatta tcacgtgaca caaatatttc    1200
tatgattgct taaaatagaa taaaaagaat ttagttgaaa ttgttttta tactgttgat     1260
tttgaataga ataatatggt aaaatggtca attcttattg gatatttatg taagaatatt   1320
ttgcattgaa attgtctaga atattttag acatataata tgatgggtaa ataatggtgt     1380
ccttcgaagt gtatgataaa agattcattt cttagactca tgtatagtaa aaaaaaaaaa   1440
ggagtgatta gcccttaaat aaatcttgat atcttgaaga attaatattt tactttgac     1500
tgaagaatgt gttggataaa tttctattta ttaatatgat atggcgtggt tgtaaagtaa    1560
atttctacta gaaatttgtg taaaaactga agtctttttg tgtaagaatg tgtaaatagt   1620
tgattaatt aatccatata gtaatgtgta tggacaaagt atagtatctg ggaccctgag    1680
attataatgt ttggtaaaat ttgggaggtg gaacgaggtc aggggacgac acatttggtc   1740
gggagaccgt gaaatttacg gtacgggaca acacaattgg gccctcaagc cccaattcag   1800
cccaatgggc tatcgaaaag aaagaaagaa agtttgtgcg ctgcggatat taataatttt   1860
gtgacgctcc accacatttc cccattccca aatttctcat tctcccattt cctctcagaa    1920
ccctcgatca ctcccacgcg ctcctatatc ctctccttca ccgtcgctct ctccaacgat    1980
cacaacaaca tcgtcatccc ctggtcggtt ttttctcta atttctctct tccttttttc    2040
gttatccgat ttgttctcac gcatcaataa ctaaatccgc gaatttctag cgtttttttt    2100
tttgttgaat ttagtggcgt cgaaatttct gagctggatt cgtatttgat ctgatcgttt   2160
aacttgaacg gtgctttttt tattttttgt ttaaaataaa ggaataaatc gtggcgattt    2220
cagatctgat ttcggtgctt cggttgagtt tttcccaaat tcatagctta ttatgatatt   2280
tttattgcgg atttcagttt acaacagctt gtgatgtgtg atgtgtttga tctgcgcaga   2340
aatcggttgt gatctgacat gtggattgat tccatttat ttattttatt ctaattttaa    2400
ttttatgagc atgttgattt aacttctttt atgtgataat tatgcgtgga aatttcaatt   2460
aaagcatata ttcttgtctt tttttttgtt tttggttgca tatattctta ttctttcatt   2520
agatttatt taatgatgtt tctatattag atttattaat gaataaatat gattttattt    2580
tgggactgaa gacacgacaa acgtaacacg gttttcttaa tttttattga tgtttacttg   2640
ttttggcact aatcactgtc tgcttctatc cccttgattt ggaagatacc gtgtttgtgg    2700
aagtattatt tacttattta gttggtcgca tattcctata atatttcatt gttatcaatc    2760
tacgaattta gtcttttttt tttggtaagc aatttgattt actttatggc atatttcaac   2820
ccaattatgt taacaagtta acaacccttt gttttttttc tttcccggag taacaattta    2880
aatgggaaaa aaaaaagatt aacaacatat tgtgcacaa ttacttggta ttgatgacca    2940
tggtggtgtg tgtctgcaac tgcaattcta taggcaaacg ccgcatct                2988
```

<210> SEQ ID NO 45
<211> LENGTH: 2988
<212> TYPE: DNA
<213> ORGANISM: Artificial Sequence
<220> FEATURE:
<223> OTHER INFORMATION: Synthetic polynucleotide

<400> SEQUENCE: 45

```
aagggcaccg ctcgttgttg atgagaacac gaaatctcct ctccacaatg caacgtcaag       60
```

```
atgtcataga caggtatgga aaggaaaaat aaataaataa ataaatggat tttatgctcc    120
acccagtttg cccttcctga ttgctaacaa aactcaactt gttttgaat agggtaataa    180 tcggggttgg ttttttgttg ttctcccttg ctgttcttta tgttgtttcc aagcgaattg    240
gactacttac gttgcaaaga aaggttactg aggccataaa agctggtatg gtgggacagg    300
cagagctaag gccccaagct gttgcagatg acgtgaatct tcatcaagtc agaggcaatc    360
gtgttcctaa taatgcagag gctcctttag aacaaagaat ccatgatgaa ctatgatgca    420
tttctaagca atactatcat gttatgtgtg tttataacac aactcttcta attcctttaa    480
aagtaacgaa agtaaaaagt attttgctat cttgagagtt cgaaaagcat ttaatactac    540 cttttgaga attattggct gatctgttat aatgaattaa aaattctttc tgtagttgtt    600
tttgtctacg ctacaggcct ttcaacaaga gcaagctaat aattgttgac gagctgtctc    660
tggctgcttt ttcattgtac caatgcttgt ctcctacaca tcaactgtat ttaagatctg    720
aagctgacat gagattttac aaagcattat ataattacat tggcgccaca ataatttcga    780
gatatttatc aaaataaata aagttgcaaa tgcaaatgga gttcacatgc aatgaatccc    840
ttgtcataaa ctccaaaatc atgattgcaa cataaacaaa tgttttagaa aaattaaaat    900
ctgtggctta cgccctcatg cacatgtttt gcgtgatgat taacagttgt tacagctccc    960
tctttctgag tcgtggtaat ttgaggtaaa tttgcgtgat gaactagtaa gttttatttt   1020
ccagtgaagc aactgctaca ggcttgggtg ttggagaaat ttaccattga gttatgcaat   1080
agttacctgg attatcctta ctttttataa tagaaaaata atcctttaa taaactcgtt   1140 tagattctgt ttatacaaat ttggtagatt aaacaaatta tcacgtgaca caaatatttc   1200
tatgattgct taaaatagaa taaaaagaat ttagttgaaa ttgtttttta tactgttgat   1260
tttgaataga ataatatggt aaaatggtca attcttattg gatatttatg taagaatatt   1320
ttgcattgaa attgtctaga atattttag acatataata tgatgggtaa ataatggtgt   1380
ccttcgaagt gtatgataaa agattcattt cttagactca tgtatagtaa aaaaaaaaaa   1440
ggagtgatta gcccttaaat aaatcttgat atcttgaaga attaatattt tactttgac    1500 tgaagaatgt gttggataaa tttctatta ttaatatgat atggcgtggt tgtaaagtaa   1560
atttctacta gaaatttgtg taaaaactga agtcttttg tgtaagaatg tgtaaatagt   1620
tgattaattt aatccatata gtaatgtgta tggacaaagt atagtatctg ggactcagag   1680
attataatgt ttggtaaaat ttgggaggtg gaacgaggtc aggggacgac acatttggtc   1740
gggagaccgt gaaatttacg gtacgggaca acacaattgg gccctcaagc cccaattcag   1800
cccattgggc tatcgaaaag aaagaaagaa agtttgtgcg ctgcggatat taataatttt   1860
gtgacgctcc accacatttc cccattccca aatttctcat tctcccattt cctctcagaa   1920
ccctcgatca ctcccacgcg ctcctatatc ctctccttca ccgtcgctct ctccaacgat   1980
cacaacaaca tcgtcatccc ctggtcggtt ttttctcta atttctctct tccttttttc   2040
gttatccgat ttgttctcac gcaacaataa ctaaatccgc gaatttctag cgtttttttt   2100
tttgttgaat ttagtggcgt cgaaatttct gagctggatt cgtatttgat ctgatcgttt   2160
aacttgaacg gtgctttttt tattttttgt ttaaaataaa ggaataaatc gtggcgattt   2220
cagatctgat ttcggtgctt cggttgagtt tttcccaaat tcatagctta ttatgatatt   2280
tttattgcgg atttcagttt acaacagctt gtgatgtgtg atgtgtttga tctgcgcaga   2340
aatcggttgt gatctgacat gtggattgat tccatttat ttattttatt ctaattttaa   2400
```

```
ttttatgagc atgttgattt aacttctttt atgtgataat tatgcgtgga aatttcaatt      2460
aaagcatata ttcttgtctt ttttttgtt tttggttgca tatattctta ttctttcatt      2520
agatttattt taatgatgtt tctatattag atttattaat gaataaatat gatttattt      2580 tgggactgaa gacacgacaa acgtaacacg gttttcttaa ttttattga tgtttacttg      2640 ttttggcact aatcactgtc tgcttctatc cccttgattt ggaagatacc gtgtttgtgg      2700
aagtattatt tacttattta gttggtcgca tattcctata atatttcatt gttatcaatc      2760
tacgaattta gtcttttttt tttggtaagc aatttgattt actttatggc atatttcaac      2820
ccaattatgt taacaagtta acaacccttt gttttttttc tttcccggag taacaattta      2880
aatgggaaaa aaaaaagatt aacaacatat ttgtgcacaa ttacttggta ttgatcacca      2940
aggtggtgtg tgtctgcaac tgcaattcta taggcaaacg ccggatct               2988
```

<210> SEQ ID NO 46
<211> LENGTH: 1353
<212> TYPE: DNA
<213> ORGANISM: Artificial Sequence
<220> FEATURE:
<223> OTHER INFORMATION: Synthetic polynucleotide

<400> SEQUENCE: 46

```
gacgagctgt ctctggctgc tttttcattg taccaatgct tgtctcctac acatcaactg       60
tatttaagat ctgaagctga catgagattt tacaaagcat tatataatta cattggcgcc      120
acaataattt cgagatattt atcaaaataa ataaagttgc aaatgcaaat ggagttcaca      180
tgcaatgaat cccttgtcat aaactccaaa atcatgattg caacataaac aaatgtttta      240
gaaaaattaa aatctgtggc ttacgccctc atgcacatgt tttgcgtgat gattaacagt      300
tgttacagct ccctctttct gagtcgtggt aatttgaggt aaatttgcgt gatgaactag      360
taagttttat tttccagtga agcaactgct acaggcttgg gtgttggaga aatttaccat      420
tgagttatgc aatagttacc tggattatcc ttacttttta taatagaaaa ataatccttt      480
taataaactc gtttagattc tgtttataca aatttggtag attaaacaaa ttatcacgtg      540
acacaaatat ttctatgatt gcttaaaata gaataaaaag aatttagttg aaattgtttt      600
ttatactgtt gattttgaat agaataatat ggtaaaatgg tcaattctta ttggatattt      660
atgtaagaat atttttgcatt gaaattgtct agaatatttt tagacatata atatgatggg      720
taaataatgg tgtccttcga agtgtatgat aaaagattca tttcttagac tcatgtatag      780 taaaaaaaa aaaggagtga ttagcccctta aataaatctt gatatcttga agaattaata      840
ttttactttt gactgaagaa tgtgttggat aaatttctat ttattaatat gatatggcgt      900
ggttgtaaag taaatttcta ctagaaattt gtgtaaaaac tgaagtcttt ttgtgtaaga      960
atgtgtaaat agttgattaa tttaatccat atagtaatgt gtatggacaa agtatagtat     1020
ctggggccct gagattataa tgtttggtaa aatttgggag gtggaacgag gtcaggggac     1080
gacacatttg gtcgggagac cgtgaaattt acggtacggg acaacacaat tgggccctca     1140
agccccaatt cagcccaatg ggctatcgaa agaaagaaa gaagtttgt gcgctgcgga      1200 tattaataat tttgtgacgc tccaccacat ttccccattc ccaaatttct cattctccca     1260
tttcctctca gaaccctcga tcactcccac gcgctcctat atcctctcct tcaccgtcgc     1320
tctctccaac gatcacaaca acatcgtcat ccc                                  1353
```

<210> SEQ ID NO 47
<211> LENGTH: 2000

<212> TYPE: DNA
<213> ORGANISM: Artificial Sequence
<220> FEATURE:
<223> OTHER INFORMATION: Synthetic polynucleotide

<400> SEQUENCE: 47

```
cttgaagcgt tggtgatgg tttgtttcaa actaagaaac cgatcaactt tagtaaccct      60
attcagcaat tgctcgaacc ccaagtatcc aacttcgagt tcttcattgg agtccgtgta     120
gtccacggta gagatcaggt agcagtattc tgccgcatca ttggaattaa aatcaataat    180
aattagataa tgtagttgtt taattaaatc aatagttaaa atttaatgag atttcaatca    240
tctaagattt ttaaccatta atgagattgg aatttaagaa ataattggga tgaagttaaa    300
attaaaaaat tctatttaca agacacaatt tgaaataggt tttaagaaaa ggtgtacaat    360
ccattattgt tattaattat tttcattgat tttttttttc tcaccatcta gttatagtct    420
atgtgataat ggcataagta ttattgagga ggcatccgtg aaatgaaata cttttcacac    480
ctctacttgt actcacacac cacaaaatat cactttacct tcttcataat ctttgccttt    540
tccattattt ttcatgtagt ttttattttat ttgtttttt ttcttctagg atcaaagata    600
tatctaaaga acgaaaaaat aagatatatc tggctattta tttgatttga caacgaataa    660
acttttactc tatcctttat tctttgggtt tacaagtatt tttatattc taagattttt     720
tactttaata tttattttta tttcaatcaa ctactttata aagtcattta ttttatgat    780
aaaattaagg taaataacat tttggctaaa ttagaaatta aagtagaata aattaaaaga    840
ttgaacaact taattatta ttattagtat tattattcaa cttaaatgcc cagatccctc     900
tatcttatac tttatcattt caggaattga ttgacttgac acaataatgc atgtgcctga    960
ccagctacgt ctaagatgtt aataagatag tactttttaa tgtaatattt tttattatta   1020
ttgattaagc tttttctaga tataaaataa tgcgggtttc agttttcaat tgataaatta    1080
atagttaata tttttataaa aattaaaata tacaaaaata aagtgataaa aattaataaa    1140
ttttctatcc tttttgagtt tttgctataa aaatctaagg agaagttccc tggttcggaa    1200
ctgacgtaga ccaattttgt aagaatcgac aatgacgggt cttttccgat ccaaatggtc    1260
cctccacagt cctagatca atccttgtcc acattcactt ggccccatct ccatgttttc    1320
tcacatcaac taattctcaa gcaaaaaaat aaaataggtt ctttgaagga atgatacagt    1380
gaccaattta atttttaaat atgtaaaaat tatgataaat taattctatt aaatttgtga    1440
atttatttta ttattaagtt ataatattta atgactaatt tgataatata ttatattttt    1500
aagattaatt tgatattaaa ggataaaatt tatgatcaat ttttttatta aattatatgt    1560
taaaattaat ttattgtatt ttttatatat ttggagatta aatttttttt tctgttcaca    1620
ctttgtcagc acttttgttg ttttttttttt caaaaagaga aaaagagaat ataaatttaa    1680
atttaaagca gaagagaacg aagcggcgtc gtttgttgcg gcctgaaaaa agtccacact   1740
cgtgaaagtc attggcataa tgacgagcat atccgtgagt gacctcggat ccgctccact    1800
aaccctagtc aactccaaac tcaaccatag ttactttact tcactcacac cccgccacgt    1860
gttccaatcg aacggtcact tctgcatcac gcgccactat aaatatctct ctctcgtcat    1920
ccgcaacccc aagcaaaacc ctaatccctc tttcttcctc ttcctcagta gtgcgatttt    1980
cgattctctt ctctgcaact                                                 2000
```

<210> SEQ ID NO 48
<211> LENGTH: 586
<212> TYPE: DNA

<213> ORGANISM: Artificial Sequence
<220> FEATURE:
<223> OTHER INFORMATION: Synthetic polynucleotide

<400> SEQUENCE: 48

```
taaaaattat gataaattaa ttctattaaa tttgtgaatt tatttattta ttaagttata      60
atatttaatg actaatttga taatatatta tatttttaag attaatttga tattaaagga     120
taaaatttat gatcaattt tttattaaat tatatgttaa aattaattta ttgtattttt      180
tatatatttg gagattaaat ttttttttct gttcacactt tgtcagcact tttgttgttt     240
ttttttttcaa aaagagaaaa agagaatata aatttaaatt taaagcagaa gagaacgaag    300
cggcgtcgtt tgttgcggcc tgaaaaaagt ccacactcgt gaaagtcatt ggcataatga    360
cgagcatatc cgtgagtgac ctcggatccg ctccactaac cctagtcaac tccaaactca    420
accatagtta ctttacttca ctcacacccc gccacgtgtt ccaatcgaac ggtcacttct    480
gcatcacgcg ccactataaa tacttagccc ctccctcatt gttaagggag caaaatctca    540
gagagatagt cctagagaga gaaagagagc aagtagccta gaagtg                   586
```

<210> SEQ ID NO 49
<211> LENGTH: 586
<212> TYPE: DNA
<213> ORGANISM: Artificial Sequence
<220> FEATURE:
<223> OTHER INFORMATION: Synthetic polynucleotide

<400> SEQUENCE: 49

```
taaaaattaa gataaattaa ttctattaaa tttgtgaatt tatttattta ttaagttata      60
atatttaatc actaatttga taatatatta tatttttaag attaatttga tattaaagga     120
taaaatttat gatcaattt tttattaaat tataagttaa aattaattta ttgtattttt      180
tatatatttg gagattaaat ttttttttct gttcacactt tgtcagcact tttgttgttt     240
ttttttttcaa aaagagaaaa agagaatata aatttaaatt taaagcagaa gagaacgaag    300
cggcgtcgtt tgttgcggcc tgaaattagt ccacactcgt gaaagtcatt ggcataatga    360
cgagcatatc cgtgagtgac ctctgatccg ctccactaac cctagtcaac tccaaactca    420
accatagtta ctttacttca ctcacacccc gccacgtgtt ccaatcgaac ggtcacttct    480
gcatcacgcg ccactataaa tacttagccc ctccctgatt gttaagggag caaaatctca    540
gagagatagt cctagagaga gaaagagagc aagtagccta gaagtg                   586
```

<210> SEQ ID NO 50
<211> LENGTH: 586
<212> TYPE: DNA
<213> ORGANISM: Artificial Sequence
<220> FEATURE:
<223> OTHER INFORMATION: Synthetic polynucleotide

<400> SEQUENCE: 50

```
taaaaattaa gataaattaa ttctattaaa tttgtgaatt tatttattta ttaagttata      60
atatttaatc actaatttga taatatatta tatttttaag attaatttga tattaaagga     120
taaaatttat gatcaattt tttattaaat tataagttaa aattaattta ttgtattttt      180
tatatatttg gagattaaat ttttttttct gttcacactt tgtcagcact tttgttgttt     240
ttttttttcaa aaagagaaaa agagaatata attttaaatt taaagcagaa gagaacgaag    300
cggcgtcgtt tgttgcggcc tgaaattagt ccacactcgt gaaagtcatt ggcataatga    360
cgagcatatc cgtgagtgac ctctgatccg ctccactaac cctagtcaac tccaaactca    420
```

```
accatagtta ctttacttca ctcacacccc gccacgtgtt ccaatcgaac ggtcacttct    480
gcatcacgcg ccactataaa tacttagccc ctccctgatt gttaagggag caaaatctca    540
gagagatagt cctagagaga gaaagagagc aagtagccta gaagtg                   586
```

<210> SEQ ID NO 51
<211> LENGTH: 2016
<212> TYPE: DNA
<213> ORGANISM: Artificial Sequence
<220> FEATURE:
<223> OTHER INFORMATION: Synthetic polynucleotide

<400> SEQUENCE: 51

```
gaacattaaa tcaagttaga atgaccccat aatccaaatt tatctttaaa aaagttatca     60
aatatatcta agaaatgtta gaaatatatt ttctaacata tttctttaac acactcaaat    120
ttaactaaaa tttattaaaa attataaaat taagagaaaa acattaaata taatataaac    180
tccacaaaat tgaattattt ttaataaatt ttaatcaata aaaataagtt taataattat    240
atactgacaa aagataaaat aattttgttg tatcatttaa ttataattta tcttagtaaa    300
ctaattatta taaaagttaa taaaattatt attatatatg tataggggt gggatgtaag    360 atgatatatc ctcaaaatgt gttagagaac gtgctaaata ttttattttt ttttaagttt    420
cccagcattt ctcgatccat atttaaaacc taaagtcatc cagataaact caagtcggat    480
cacgccgggc atgttatgct taccccctaat tataacaaat ttaagtcaaa tttgaattta    540
ctctgaattg ttatcaatgt taaaatctta cactactaat acataaaaat tagtattttg    600
ttatttactg aatgtatttt acacaatggt caaaacgttg tttttttttgt tttgaatgcg    660 gtcaaaacgg ttttttaaagc atcaaaatac atgccattgt caggtacgaa ggtttttttt    720 tttttttcc tttctatcga gggagggata ataagaatat aaaatctcgt taaataacga    780
ataaaataaa tgataagaat tatgttaatt gtcattttat acgcataatt attgagcaca    840
ccgttatctt ctagctgtaa catgctaaac tcgagaacaa aagaaaaaaa aaatgaagta    900
tatttagctg ttgtctattc atttgttagc cgttgtaatt ttttcacgtg tcattgtaat    960 tttttttatga aaaaaaacgc ccatgaaaga aggcacaagc cactgtggcc aattaatagc   1020
tgttaccatt ttaatacact gagttttcaa ctttgaatgg tcaaaagcta agggacaaga   1080
aaaccaggtt acacttgcta gattttttcta ttttttattta tttattttcc gaaaatacag   1140
aattattgaa gaaataaat aaatagttag aatgggttgg ttttcttctt tgactgtcac   1200
cagcgcatta tagcacacca cacaaaaaag caaagcagaa aacaactgtt acttacacac   1260
gccatgggta tgggtatggg tatgggtatg ggtatgtatg ccattatcat catcgatcta   1320
actctaactc tctctttctc ttccttctaa ccgccgcttc cgcatctcgc ttccttctct   1380
tccttctcta actatatata ttttctttttt ctctctgttt cttccttttt attttatgct   1440
tttttctccg atgtgactgg cgtttgtttg gtgtgttttt cgtgtgcgtc gaaccctctg   1500
cgttcgttaa ttttgttttg tgtttccgga tcgacttgtt tcgcgttcgg ttgcggggat   1560
cttcggttta ggtttgttta gggatttttt gtttttttgt ttttttttct gttgttcatg   1620 agttttcgt tggatttgtt gtgttctgtg agattgatgg gctttttttt taaaatttat   1680
attccttcaa tgttttttct tttttggcaa aatgaatatt tatttatggg cggaatgtat   1740
ttgcgatttt tgtctcttaa attcatgttc gaacggtggt gtgactttcc tgtttggttc   1800
tgtttttatg aagcctgttg actgcaattt tgcttctgaa aaattaaaaa ggaaatatgt   1860
```

-continued

| | |
|---|---|
| tactgtcatt tttctacgca tatctaatat atcttctttt tgttttttat ttatttattt | 1920 |
| taattatggt ggaattgttc attctggcag gtaaatgagt ggtaaatgag tggtttttga | 1980 |
| gcagaagcag ttaaaagaga aagggattca gcgaag | 2016 |

<210> SEQ ID NO 52
<211> LENGTH: 1417
<212> TYPE: DNA
<213> ORGANISM: Artificial Sequence
<220> FEATURE:
<223> OTHER INFORMATION: Synthetic polynucleotide

<400> SEQUENCE: 52

| | |
|---|---|
| gttatttact gaatgtattt tacacaatgg tcaaaacgtt gttttttttg ttttgaatgc | 60 |
| ggtcaaaacg ttttttaaag catcaaaata catgccattg tcaggtacga aggttttttt | 120 |
| ttttttttc ctttctatcg agggagggat aataagaata taaaatctcg ttaaataacg | 180 |
| aataaaataa atgataagaa ttatgttaat tgtcatttta tacgcataat tattgagcac | 240 |
| accgttatct tctagctgta acatgctaaa ctcgagaaca aaagaaaaaa aaaatgaagt | 300 |
| atatttagct gttgtctatt catttgttag ccgttgtaat ttttttcacgt gtcattgtaa | 360 |
| ttttttttatg aaaaaaaacg cccatgaaag aaggcacaag ccactgtggc caattaatag | 420 |
| ctgttaccat tttaatacac tgagttttca actttgaatg gtcaaaagct aagggacaag | 480 |
| aaaaccaggt tacacttgct agattttttct attttttattt atttatttttc cgaaaatatca | 540 |
| gaattattga agaaaataaa taaatagtta gaatgggttg gttttcttct ttgactgtca | 600 |
| ccagcgcatt atagcacacc acacaaaaaa gcaaagcaga aaacaactgt tacttacaca | 660 |
| cgccatgggt atgggtatgg gtatgggtat gggtatgtat gccattatca tcatcgatct | 720 |
| aactctaact ctctcttttct cttccttcta accgccgctt ccgcatctcg cttccttctc | 780 |
| ttccttctct aactatatat attttctttt tctctctgtt tcttccttttt tattttatgc | 840 |
| ttttttctcc gatgtgactg gcgtttgttt ggtgtgtttt tcgtgtgcgt cgaaccctct | 900 |
| gcgttcgtta attttgtttt gtgtttttcgg atcgacttgt ttcgcgttcg gttgcgggga | 960 |
| tcttcggttt aggtttgttt agggattttt tgttttttgt ttttttttc tgttgttcat | 1020 |
| gagttttttcg ttggatttgt tgtgttctgt gagattgatg ggctttttttt ttaaaattta | 1080 |
| tattccttca atgtttttc ttttttggca aaatgaatat ttatttatgg gcggaatgta | 1140 |
| tttgcgattt ttgtctctta aattcatgtt cgaacggtgg tgtgactttc ctgtttggtt | 1200 |
| ctgttttttat gaagcctgtt gactgcaatt ttgcttctga aaattaaaa aggaaatatg | 1260 |
| ttactgtcat ttttctacgc atatctaata tatcttctttt ttgttttttta tttatttatt | 1320 |
| ttaattatgg tggaattgtt cattctggca ggtaaatgag tggtaaatga gtggtttttg | 1380 |
| agcagaagca gttaaaagag aaagggattc agcgaag | 1417 |

<210> SEQ ID NO 53
<211> LENGTH: 1619
<212> TYPE: DNA
<213> ORGANISM: Artificial Sequence
<220> FEATURE:
<223> OTHER INFORMATION: Synthetic polynucleotide

<400> SEQUENCE: 53

| | |
|---|---|
| ctaattagct aatcacaaaa aaggttattg cctaattaat agtagggatt gaagaagtat | 60 |
| caataatcaa taagagggac atttggattg acacaaaacta ttagtataaa aaaaaaatgt | 120 |
| aaaactaaat ggacaacaat ctaagaaagc gagtatgtgt tgtactcgga aaacataaca | 180 |

```
taatgtgatt ttgattgtgg aaactgaaaa caataacatt taagttttat ttatctcttt    240
gcctaacaat ttttttaatt acttttttta tagtttttat gatgaagata attaatattt    300
tttacaaata ttatattttc cttttttacca tctttgaaga taattgcttt ttttttccaat  360 ttagacaaat atttgagtat caatgatatt ccttttttaat ccattattgc aatttaaaag   420
accatcaatg attacatttt caatcaaatg actttattag tcttcactttt acatcgattt   480 aaatcaaact aataattttg tatggactaa atctctgaac attttttatat ttacaacata   540 ttttaacatt tattaaataa ttagtattta atactattag tagaataatg ggagtagcag    600
gagggaggca ctgagagaat agagatggca tggaagtaag caatcaagtc aaaatcagag    660
ttggccaacc ccaaaggctg tagtaggtaa gcatggccca ttttagttttt tacattcatc    720 tctcattttc acctcaacgg ttcagattca atctgactcc ccgatctcag ccgtggattc    780
aaatgccacc tcaggcacat gcaattccaa atggatgaac ctaacccaca atctaatctt    840
gttacttagg ggcttttccg tcattaaatg acaccaccta cccccttctc cctataaatg    900
gcaactcaat tgccccccctt agaactcgca gcgcttgatt tgaggccagg caagccccac    960
tcaaccacca cacctctcct cgttcacgct acccctttct gctcttcttc tacctttcaa   1020
ggtactcttc tttccctctg ttgctgcaac cttctctttc tttaagattg cctcaatttc   1080
ggatcttgca cctctgggtt gctttgcttt gcttttttcct ctactgggtt gatttctgtt   1140
tccctaaacc ggtttagacg aatgtgaaca ctacttcttt tgtttaatta ctctggaata   1200
cgtgttaggc tttcagatct agttgaaatc gtattgcact tttaggggga gtttggattt   1260
ctaataagaa attgaccttt tgctgagaat tggttcggtg attagagggt ttccgtaaat   1320
ttttgaagtt ttacatgctt gtatctgttt attttttgttt ctcacatcta ttattgttag   1380
gtgaaggaaa ttatgtattg agagtctgtc tgatactaaa tataaacacc tcaataggggg  1440 ctctaacact gattttatca tttgctgctt gtgtgtatgg ttaaagaaag gcaattgtgt   1500
tttaattttc tgcaagcttt cgtttgctga attttatgca tatattttcc tcccttttgt   1560
gaacttcctt tttgtagttc taattccatt tttggtgtct gcagttttaa aagtataaa    1619
```

<210> SEQ ID NO 54
<211> LENGTH: 1614
<212> TYPE: DNA
<213> ORGANISM: Artificial Sequence
<220> FEATURE:
<223> OTHER INFORMATION: Synthetic polynucleotide

<400> SEQUENCE: 54

```
tccaccctca caaaaaaggt tattgcctaa ttaatagtag ggattgaaga agtatcaata     60
atcaataaga gggacatttg gattgacaca aactattagt ataaaaaaaa aatgtaaaac    120
taaatggaca acaatctaag aaagcgagta tgtgttgtac tcggaaaaca taacataatg    180
tgattttgat tgtggaaact gaaaacaata acaattaagt tttatttatc tctttgccta    240 acaattttttt taattacttt tttatagtt tttatgatga agataattaa tattttttac    300
aaatattata ttttccttttt taccatcttt gaagataatt gctttttttt ccaatttaga   360
caaatatttg agtatcaatg atattccttt ttaatccatt attgcaattt aaaagaccat    420
caatgattac attttcaatc aaatgacttt attagtcttc actttacatc gatttaaatc    480
aaactaataa ttttgtatgg actaaatctc tgaacatttt tatatttaca acatatttta    540
acatttatta ataattagt atttaatact attagtagaa taatgggagt agcaggaggg    600
```

| | |
|---|---|
| aggcactgag agaatagaga tggcatggaa gtaagcaatc aagtcaaaat cagagttggc | 660 |
| caacccccaaa ggctgtagta ggtaagcatg gcccatttta gttttacat tcatctctca | 720 |
| tttcacctc aacggttcag attcaatctg actccccgat ctcagccgtg gattcaaatg | 780 |
| ccacctcagg cacatgcaat tccaaatgga tgaacctaac ccacaatcta atcttgttac | 840 |
| ttaggggctt ttccgtcatt aaatgacacc acctaccccc ttctccctat aaatggcaac | 900 |
| tcaatccccc ccttagaact cgcagcgctt gatttgaggc caggcaagcc ccactcaacc | 960 |
| accacacctc tcctcgttca cgctaccct ttctgctctt cttctacctt tcaaggtact | 1020 |
| cttcttccc tctgttgctg caaccttctc tttctttaag attgcctcaa tttcggatct | 1080 |
| tgcacctctg ggttgctttg ctttgctttt tcctctactg ggttgatttc tgtttcccta | 1140 |
| aaccggttta gacgaatgtg aacactactt cttttgttta attactctgg aatacgtgtt | 1200 |
| aggctttcag atctagttga aatcgtattg cacttttagg gggagtttgg atttctaata | 1260 |
| agaaattgac cttttgctga gaattggttc ggtgattaga gggtttccgt aaatttttga | 1320 |
| agttttacat gcttgtatct gtttattttt gtttctcaca tctattattg ttaggtgaag | 1380 |
| gaaattatgt attgagagtc tgtctgatac taaatataaa cacctcaata ggggctctaa | 1440 |
| cactgattt atcatttgct gcttgtgtgt atggttaaag aaaggcaatt gtgttttaat | 1500 |
| tttctgcaag ctttcgtttg ctgaattta tgcatatatt ttcctccctt ttgtgaactt | 1560 |
| cctttttgta gttctaattc cattttggt gtctgcagtt ttaaaagtat aaag | 1614 |

<210> SEQ ID NO 55
<211> LENGTH: 2179
<212> TYPE: DNA
<213> ORGANISM: Artificial Sequence
<220> FEATURE:
<223> OTHER INFORMATION: Synthetic polynucleotide

<400> SEQUENCE: 55

| | |
|---|---|
| attaaaattc aaggaataaa aattataaat ttgagaaact agagtgatta aaattataat | 60 |
| ttaaccttta tattaaaaaa taattttat tatctaaaaa aatcaaaatt ttatactcct | 120 |
| gatatttgat tttatacat aaaaggccaa tactttatat tgtacatata ttttaatttt | 180 |
| aatataaaat taattcgatt caactttata ccaaacatat aatttaaata gcaacttcta | 240 |
| catttatgaa gatgtttaag taacaaactt tgaattgagt tccggatgcg caaatgatga | 300 |
| taggacaaaa gtatctggtc aaaacattca ggcaggcatg tcctattatc accgttttg | 360 |
| gctatttcat tgatttatta aattaaatat catgccaccc tccaaccatt gccacaagtt | 420 |
| tcgaacccca gaaagaaagt aaaaggctag tgagtggttt gaaaattgaa agccacgtgt | 480 |
| atgcgaacat tggcttccac ttcaaaaacg tgatgatgtg cccactgaat ccgatcctcc | 540 |
| tcgctccttt gtgatttctc attagaaaat agaatctaga aactatagga tagcgttaca | 600 |
| cacttacaaa atataagtat ttcactcaat ttttgacaag ttgttatttt tcggtaaat | 660 |
| tatgataatg acatttaat tttagtacat gaatgagtta atgttaaaaa taaggaat | 720 |
| aagaagttag cttttataat tttatgataa tattaataat aataataata atagtgattt | 780 |
| tttaagatat gaaaactaa atttatgttt tttttcccaa ataactgcta attagtatga | 840 |
| ataggatagg attagtacaa tctattgcag gaaagtatgt gttcatgttt tattagacaa | 900 |
| aaattaaaca aaatttaaa ataaaaaaca gaggaaatca tgccttggct tggtaactta | 960 |
| ctatcttctg gtccttcata tgataaacaa acagtgtttt tttcccctaa tcataagaat | 1020 |
| catataatta ttttaaatg tattaataac tatttttta tatctttaat ttgttgtgaa | 1080 |

```
gtcttttaat gatcactcat tattcatgaa agtatataca gttaatgaac tattaataat     1140
ataacttatt ctcatcggtt aacaagtatt tttcatgtat tatgagtagt gatattatat     1200
gtaaccactt cttatatcca ttgattttat ggatatttt aaaataaaat ttgaatttat      1260
attagtatta attaaaagta actactttaa tcatttttat ttgtcttgat tatttaatct     1320
tatggttttc atttgtgatg atgatcaaag atagtatgat agtatgattt tgttatattt     1380
gtgcaacact tagttatgtt taataatttt ttttaaaaaa atataaatat attgaaaagg     1440
tcatatgcaa gcggtagcct cacccaagaa taattaaaat agacccaaat tctctgaata     1500
aatagaccta aatactccat gaatgtgttt cattgtttgt tatttgatgt tcatcaaata     1560
tcaaatataa ttaaagctca tcatattctc gtacagtata gtattagtat tatatcctgc     1620
tcactaaacc aaacatctaa gaataacctt atttcattta gaaaaaaaaa aaaaaaaacc     1680
caagtaaaat tgaaaaaaga atcaaaacaa taaaaagaga gaaaagcgaa tggaatattc     1740
gcatatctgt tggcgtgaaa cagaaccac aaaaaaaaaa aaaaaaaaaa cggtacagcg      1800
tagtagtcct tggcaaagca tcacgagtca caaggcggtc ccgtaggagt cacgcacttc     1860
acttggccca tttacctgtc attgcggtct tttactcttc tcaataccttt attaaaaccc    1920 tatctcactc actcactcac accgttccat ttctcaacaa cttctgctac ttcctactcc     1980
aaccgcactt ctgctccgca attatcctgg gtatgcaatt aaccgccacg cactctcacg     2040
ttttttctct tcttcttatt tctttccatt ttcaactctt ctctgtttct tccgatctga     2100
tttttttctt ctttctttc tgattttct tttgttttgt tttcaaatga attgcatgga       2160
tcaggtaagt agctgatcg                                                  2179

<210> SEQ ID NO 56
<211> LENGTH: 2138
<212> TYPE: DNA
<213> ORGANISM: Artificial Sequence
<220> FEATURE:
<223> OTHER INFORMATION: Synthetic polynucleotide

<400> SEQUENCE: 56
aggattaatg cacaacctag acaaattcgt ttttcgagga tgatgcatgg gaacctacca      60
gttaacagcc agctagttgg tgtcccatta acttggatgg tctaatttaa atattggtgt    120
ggcatcttta ggatcacaga ttcacaaggc tggggcgttg gatctataat aagggatagt    180
gatggagttg ttggaagcag caacttggtg cataccaaga taatgtgaca caagttataa    240
gtaaagtgga agctttaggc ctccaacaac ccattactga accaaacttg ccaaagtctt    300
ttatttccgt aatttggaaa tatctatgta gttggtttct taatttaatt aaaggtggaa    360
tgaaaactct ccctcacacg tcacaacttt gtatgatagc tcaaggtttg tatcttctgg    420
ctcataaatt tcaaggttgt ctgcttcagc atgataaggg aacaaggaaa cacactgtac    480
atggcttagc gttctacgct ggtattcatc cggaagaagt ttggatagaa caagttccca    540
tccacttcgt atcgatctct tctattttt ttttggtaat caattttttt tccatactct     600
cgatatcatt tcattagaaa ttaatctcat ttgtgatgta tgattattat taacctaaaa    660
aattttatac gcgatgagaa tataatattt ttattaaata aattattctc acttatatga    720
atataatgat atttagaag ttttatcttt atctcaaccc tcttgattaa tgttagtgac     780
cattttatat attgttgttt cgtgattctt tattattcga acatgtgtgc ttggaatatt    840
tgaatcggtc ctaaaaaaag caattaccta tgccttattc ttgtaaataa attttaaagg    900
```

```
catatataaa gtgaatattc agtaaataat ttaatgattt ttcagaatat tatctaatta    960
taagttatct caaaaaaatc taatcataaa aaaataaaaa aaatgtgtat ttggataaca   1020
ttcaaaatca tgataaatca taataagttg aatcaaccct gattttgata aaaaaaatta   1080
tatgtttgga ttatcttcaa aattgataga atcaatttta atggaaaaaa aaactaggta   1140
gagttaaagc aaatagaagt aaattttact tcttccaaaa ttaattctac ttgaattta    1200
actaatttac tttcacatca attcactcat gcatatgttt attatttatt tcttaatttt   1260
aaaatataat taaatatgtc aaaataaaaa tataattaaa agtattgcta gatttattta   1320
atttaaata taatttattt aatttatcct cacacttata tctttactgg tgtgataaat    1380
cttattttct tatctatttt atccaatttc attgttttac aagaaatatt attctatttc   1440
aaaagttaac atattataca catattttct taatttgaat tatctctatt taattttaat   1500
ttttatatat aaaactaatt ataataaaaa gtgtacataa atattaaaac ccaattttga   1560
tcattatacc ttcaaaatta attttgatta aaagcattca ataatatat ttttttaaaaa   1620
tcacttattt ataaccttt atccgaataa aaatcacgtt atttcatgat taattctgtg    1680
aaattaattt tatgaggcta atcaaaacgc acacttaagc tcatttaata aaaataatag   1740
aatcacattg acgtgaggca gaaatcgcaa aaaagggtat agcgtaatcc atggcacagt   1800
atcacaggtc atacgccggt catgtaggtg tcacccaccc gacccaccta cttcacttac   1860
ctttacgtgc cattttgctc ttttttaccc ttctttcaac ccttttattaa aaccctatct  1920
cgctcgcact cacccacaca ccatccgttc tagtctcaac ttctgctctt ccaactccta   1980
caacgctttt ctctgcactc ctgggtaagc aaataaccac cacactctca cgcttttctt   2040
tccatttca actctaccgc gtttcgtttc tctcgatctg acatttttct tctttctgtt    2100
tctaaatgaa tggcatggat cagtgaaggt taagtgag                           2138
```

<210> SEQ ID NO 57
<211> LENGTH: 2239
<212> TYPE: DNA
<213> ORGANISM: Artificial Sequence
<220> FEATURE:
<223> OTHER INFORMATION: Synthetic polynucleotide

<400> SEQUENCE: 57

```
tagaatgacc ccataatcca aatttatctt taaaaaagtt atcaaatata tctaagaaat     60
gttagaaata tattttctaa catatttctt taacacactc aaatttaact aaaatttatt   120
aaaaattata aaattaagag aaaaacatta aatataatat aaactccaca aaattgaatt   180
attttaata aattttaatc aataaaaata agtttaataa ttatatactg acaaaagata    240
aaataatttt gttgtatcat ttaattataa tttatcttag taaactaatt attataaaag   300
ttaataaaat tattattata tatgtatagg gggtgggatg taagatgata tatcctcaaa   360
atgtgttaga gaacgtgcta aatatttat tttttttttaa gtttcccagc atttctcgat   420
ccatatttaa aacctaaagt catccagata aactcaagtc ggatcacgcc gggcatgtta   480
tgcttacccc taattataac aaatttaagt caaatttgaa tttactctga attgttatca   540
atgttaaaat cttacactac taatacataa aaattagtat tttgttattt actgaatgta   600
ttttacacaa tggtcaaaac gttgtttttt ttgttttgaa tgcggtcaaa acggttttta   660
aagcatcaaa atacatgcca ttgtcaggta cgaaggtttt tttttttttt ttcctttcta   720
tcgagggagg gataataaga atataaaatc tcgttaaata acgaataaaa taaatgataa   780
gaattatgtt aattgtcatt ttatacgcat aattattgag cacaccgtta tcttctagct   840
```

```
gtaacatgct aaactcgaga acaaaagaaa aaaaaaatga agtatattta gctgttgtct    900
attcatttgt tagccgttgt aattttttca cgtgtcattg taattttttt atgaaaaaaa    960
acgcccatga aagaaggcac aagccactgt ggccaattaa tagctgttac cattttaata   1020
cactgagttt tcaactttga atggtcaaaa gctaagggac aagaaaacca ggttacactt   1080
gctagatttt tctattttta tttatttatt ttccgaaaat acagaattat tgaagaaaat   1140
aaataaatag ttagaatggg ttggttttct tctttgactg tcaccagcgc attatagcac   1200
accacacaaa aaagcaaagc agaaaacaac tgttacttac acacgccatg ggtatgggta   1260
tgggtatggg tatgggtatg tatgccatta tcatcatcga tctaactcta actctctctt   1320
tctcttcctt ctaaccgccg cttccgcatc tcgcttcctt ctcttccttc tctaactata   1380
tatattttct ttttctctct gtttcttcct ttttattttc tgcttttttc tccgctgtga   1440
ctggcgtttg tttggtgtgt ttttcgtgtg cgtcgaaccc tctgcgttcg ttaattttgt   1500
tttgtgtttt cggatcgact tgtttcgcgt tcggttgcgg ggatcttcgg tttaggtttg   1560
tttagggatt ttttgttttt tgttttttt ttctgttgtt catgagtttt tcgttggatt    1620
tgttgtgttc tgtgagattg atgggctttt tttttaaaat ttatattcct tcaatgtttt   1680
ttcttttttg gcaaaatgaa tatttattta tgggcggaat gtatttgcga tttttgtctc   1740
ttaaattcat gttcgaacgg tggtgtgact ttcctgtttg gttctgtttt tatgaagcct   1800
gttgactgca attttgcttc tgaaaaatta aaaaggaaat atgttactgt cattttctca   1860
cgcatatcta atatatcttc tttttgtttt ttatttattt attttaatta tggtggaatt   1920
gttcattctg gcaggtaact gagtggtaac tgagtggttt ttgagcagaa gcagttaaaa   1980
gagaaaggga ttcagcgaag ctgacatcgg ttggtgtggc accaacttcg ggtttgagag   2040
aagccagtgg gcctggagca gcaggtgttg atagattgcc agaggagctg aacgatctga   2100
aaattagggc tgatagagta tgtaatttgt aaccccgctc tttgatattt tcgttttttt   2160
catgttagtt ttattttctc tatgtccatg ttgttggtta cttacagttt gcttcatttt   2220
gtagtaaata gaagctaga                                               2239
```